United States Patent
Cooper et al.

(10) Patent No.: US 6,432,959 B1
(45) Date of Patent: Aug. 13, 2002

(54) INHIBITORS OF FARNESYL-PROTEIN TRANSFERASE

(75) Inventors: Alan B. Cooper, West Caldwell; Ronald J. Doll, Maplewood, both of NJ (US); Johan A. Ferreira, Bensalem, PA (US); Ashit Ganguly, Upper Montclair, NJ (US); Viyyoor M. Girijavallabhan, Parsippany, NJ (US); Arthur G. Taveras, Denville, NJ (US); Jianping Chao, Summit, NJ (US); John J. Baldwin, Gwynedd Valley, PA (US); Chia-Yu Huang, Plainsboro; Ge Li, Lawrenceville, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/469,465

(22) Filed: Dec. 22, 1999

Related U.S. Application Data

(60) Provisional application No. 60/113,405, filed on Dec. 23, 1998.

(51) Int. Cl.[7] ................... A61K 31/496; C07D 401/14; C07D 403/12; C07D 411/14; A61P 35/00
(52) U.S. Cl. .................... 514/253.09; 514/254.02; 514/254.05; 544/364; 544/367; 544/370
(58) Field of Search ................. 514/254.05, 253.09, 514/254.02; 544/370, 364, 637

(56) References Cited

U.S. PATENT DOCUMENTS

| | | | | |
|---|---|---|---|---|
| 5,439,918 A | | 8/1995 | deSolms et al. | 514/307 |
| 5,491,164 A | | 2/1996 | deSolms et al. | 514/423 |
| 5,534,537 A | | 7/1996 | Ciccarone et al. | 514/397 |
| 5,696,121 A | * | 12/1997 | Bishop | 514/254 |
| 5,719,148 A | | 2/1998 | Bishop et al. | 514/228.2 |
| 5,801,175 A | * | 9/1998 | Afonso | 514/254 |
| 5,874,442 A | | 2/1999 | Doll et al. | 514/290 |
| 5,880,128 A | * | 3/1999 | Doll | 514/255 |
| 5,968,938 A | * | 10/1999 | Bell | |

FOREIGN PATENT DOCUMENTS

| | | | |
|---|---|---|---|
| WO | WO 94/13646 | | 6/1994 |
| WO | WO 95/00497 | | 1/1995 |
| WO | WO 97/18813 | | 5/1997 |
| WO | WO 98/37079 | * | 8/1998 |
| WO | WO 98/54966 | | 12/1998 |
| WO | 98/57960 | * | 12/1998 |
| WO | 2000039119 | * | 7/2000 |

OTHER PUBLICATIONS

Khosravi–Far R et al. Cell Growth & Differentiation. 3, 461–9, Jul. 1992.*
J.G. Breitenbucher et al., "Generation of a Piperazine–2–carboxamide Library: A Practical Application of the Phenol–Sulfide React and Release Linker," *Tetrahedron Letters*, vol. 39, pp. 1295–1298 (1998).
International Search Report for PCT/US99/27958 (Apr. 17, 2000).

* cited by examiner

*Primary Examiner*—Evelyn Mei Huang
(74) *Attorney, Agent, or Firm*—Robert L. Bernstein

(57) ABSTRACT

Novel compounds and pharmaceutical compositions are disclosed which are inhibitors of the enzyme, farnesyl protein transferase. Also disclosed is a method of inhibiting Ras function and therefore inhibiting the abnormal growth of cells. The method comprises administering the novel aminooxyamide compound to a biological system. In particular, the method inhibits the abnormal growth of cells in a mammals such as a human.

6 Claims, No Drawings

INHIBITORS OF FARNESYL-PROTEIN TRANSFERASE

REFERENCE TO RELATED APPLICATIONS

This application claims the benefit of U.S. Provisional Application Serial No. 60/113,405 filed Dec. 23, 1998.

BACKGROUND

Patent application WO 95/00497 published Jan. 5, 1995 under the Patent Cooperation Treaty (PCT) describes compounds which inhibit the enzyme, farnesyl-protein transferase (FTase) and the farnesylation of the oncogene protein Ras. Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anti-cancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be additional compounds useful for the inhibition of farnesyl protein transferase. Such a contribution is provided by this invention.

SUMMARY OF THE INVENTION

Inhibition of farnesyl protein transferase by compounds of this invention has not been reported previously. Thus, this invention provides a method for inhibiting farnesyl protein transferase using compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Compounds of the present invention are represented by Formula 1.0:

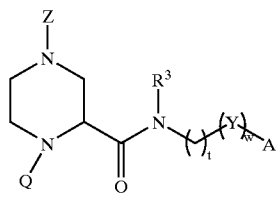

(1.0)

or a pharmaceutically acceptable salt or solvate thereof, wherein Q is:

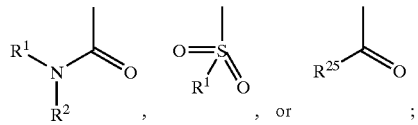

Z represents hydrogen, alkyl, aryl, arylalkyl, cycloalkyl, cycloalkylalkyl,

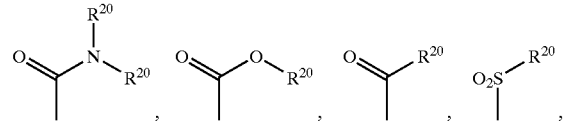

heteroaryl, heteroarylalkyl, heterocycloalkyl, heterocycloalkylalkyl, cycloalkenyl, cycloalkenylalkyl, or —$CY^3Y^4$ wherein $Y^3$ and $Y^4$ independently represent alkyl and aryl or $Y^3$ and $Y^4$, together with the attached carbon atom (—C), can form a cycloalkyl or a cycloalkenyl ring;

wherein $R^1$, $R^2$, $R^3$, $R^{20}$, $R^{22}$, $R^{30}$ and $R^{32}$ independently represent hydrogen, alkyl, aryl, arylalkyl, cycloalkyl, cycloalkylalkyl, heteroaryl, heteroarylalkyl, heterocycloalkyl or heterocycloalkylalkyl;

$R^{25}$ can represent hydrogen, alkyl, cycloalkyl, cycloalkylalkyl, heterocycloalkyl, heterocycloalkylalkyl or —$OR^{40}$ wherein $R^{40}$ can represent alkyl, aryl, arylalkyl, cycloalkyl, cycloalkylalkyl, heteroaryl, heteroarylalkyl, heterocycloalkyl or heterocycloalkylalkyl;

Y represents aryl, heteroaryl, heterocycloalkyl or cycloalkyl, t is zero, 1, 2 or 3;

w is zero or 1; and

A is nothing, hydrogen, alkyl, aryl, arylalkyl, cycloalkyl, cycloalkylalkyl, heterocycloalkyl, heterocycloalkylalkyl, cyano, heteroaryl or heteroarylalkyl.

In another embodiment, the present invention is directed toward a pharmaceutical composition for inhibiting the abnormal growth of cells comprising an effective amount of compound (1.0) in combination with a pharmaceutically acceptable carrier.

In another embodiment, the present invention is directed toward a method for inhibiting the abnormal growth of cells, including transformed cells, comprising administering an effective amount of compound (1.0) to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs, and (4) benign or malignant cells that are activated by mechanisms other than the Ras protein. Without wishing to be bound by theory, it is believed that these compounds may function either through the inhibition of G-protein function, such as ras p21, by blocking G-protein isoprenylation, thus making them useful in the treatment of proliferative diseases such as tumor growth and cancer, or through inhibition of ras farnesyl protein transferase, thus making them useful for their antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells, prostate tumor cells, breast tumor cells or colon tumors cells. Also, the inhibition of the abnormal growth of cells by the treatment with compound (1.0) may be by inhibiting ras farnesyl protein transferase. The inhibition may be of tumor cells wherein the Ras protein is activated as a result of oncogenic mutation in genes other than the Ras gene. Alternatively, compounds (1.0) may inhibit tumor cells activated by a protein other than the Ras protein.

This invention also provides a method for inhibiting tumor growth by administering an effective amount of compound (1.0) to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, melanoma, prostate carcinoma and breast carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the N-substituted urea compounds (1.0) described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the N-substituted urea compounds (1.0).

In another embodiment, the present invention is directed toward a method for inhibiting ras farnesyl protein transferase and the farnesylation of the oncogene protein Ras by administering an effective amount of compound (1.0) to mammals, especially humans. The administration of the compounds of this invention to patients, to inhibit farnesyl protein transferase, is useful in the treatment of the cancers described above.

DETAILED DESCRIPTION OF THE INVENTION

As used herein, the following terms are used as defined below unless otherwise indicated:

BOC—represents tert-butoxycarbonyl;

BOC-ON—represents [2-(tert-butoxycarbonyloxyimino)-2-phenylacetonitrile];

C—represents carbon;

CBZ—represents benzyloxycarbonyl;

$ClCO_2Et$—ethyl chloroformate;

$CPh_3$—represents triphenylmethyl;

cycloalkyl-represents a saturated carbocyclic ring, branched or unbranched, of from 3 to 20 carbon atoms, preferably 3 to 7 carbon atoms;

DBU—represents 1,8-diazabicyclo[5.4.0]undec-7-ene;

DCC—represents dicyclohexylcarbodiimide;

DCM—represents dichloromethane;

DIC—represents diisopropylcarbodiimide;

DIPEA—diiosopropyl ethylamine

DMAP—represents 4-dimethylaminopyridine;

DMF—represents N,N-dimethylformamide;

EDC (also DEC)—represents 1-(3-dimethylaminopropyl)-3-ethylcarbodiimide hydrochloride or 1-ethyl-3-(3-dimethylaminopropyl) carbodiimide hydrochloride;

EtOAc—ethyl acetate;

EtOH—ethanol;

$Et_3N$—triethylamine;

FMOC—represents 9-fluorenylmethyoxycarbonyl;

FMOC-Cl—represents 9-fluoroenylmethyl chloroformate;

HATU—represents [O-(7-azabenzotriazol-1-yl)-1,1,3,3-tetramethyluronium hexafluorophosphate];

HOAc or AcOH—acetic acid;

HOBT—hydroxybenzotriazole;

Lutidine—2,6-lutidine;

MCPBA—represents m-chloroperbenzoic acid;

Me—methyl;

MeOH—methanol;

$NaBH^5CN$—sodium cyano borohydride

Ph—represents phenyl;

TBAF—represents tetrabutylammonium fluoride;

TFA—represents trifluoroacetic acid;

TFAA—trifluoroacetic anhydride;

THF—represents tetrahydrofuran;

$M^+$-represents the molecular ion of the molecule in the mass spectrum;

$MH^+$-represents the molecular ion plus hydrogen of the molecule in the mass spectrum;

Bu-represents butyl;

Et—represents ethyl;

Me—represents methyl;

Ph—represents phenyl;

benzotriazol-1-yloxy represents

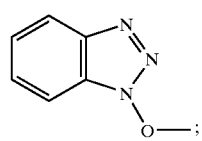

1-methyl-tetrazol-5-ylthio represents

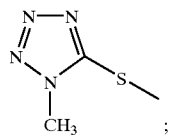

alkyl-(including the alkyl portions of alkoxy, alkylamino and dialkylamino)-represents straight and branched carbon chains and contains from one to twenty carbon atoms, preferably one to ten carbon atoms, also preferably one to six carbon atoms; for example methyl, ethyl, propyl, iso-propyl, n-butyl, t-butyl, n-pentyl, isopentyl, hexyl, isononyl and the like; wherein said alkyl group may be optionally and independently substituted with one, two, three or more of the following: halo, alkyl, aryl, cycloalkyl, cyano (—CN), —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$—$NR^{12}COR^{10}$, —$COR^{10}$, —$OCOR^{10}$, —$OCO_2R^{10}$ or —$COOR^{10}$, wherein $R^{10}$ and $R^{12}$ can independently represent hydrogen, alkyl, alkoxy, aryl, arylalkyl, heteroaryl, heteroarylalkyl, cycloalkyl, cycloalkylalkyl, heterocycloalkyl or heterocycloalkylalkyl;

alkenyl-represents straight and branched carbon chains having at least one carbon to carbon double bond and containing from 2 to 12 carbon atoms, preferably from 2 to 6 carbon atoms and most preferably from 3 to 6 carbon atoms; wherein said alkenyl group may be optionally and independently substituted with one, two, three or more of the following: halo, alkyl, aryl, alkoxy, amino, alkylamino, cyano (—CN), —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

alkoxy-an alkyl moiety of one to 20 carbon atoms covalently bonded to an adjacent structural element through an oxygen atom, for example, methoxy, ethoxy, propoxy, butoxy, pentoxy, hexoxy and the like; wherein said alkoxy group may be optionally and independently substituted with one, two, three or more of the following: halo, alkyl, aryl, cycloalkyl, cyano (—CN), —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

aryl (including the aryl portion of arylalkyl)—represents a carbocyclic group of 6 to 15 carbon atoms containing one or two aromatic rings (e.g., aryl is phenyl); wherein optionally, said aryl group can be fused with one other aryl, cycloalkyl, heteroaryl or heterocycloalkyl ring provided that when the moiety "Z" in compound (1.0) is aryl, the fused aryl is a bicyclic ring (e.g napthalene) which is not a tricyclic or greater fused ring system; and wherein any of the available substitutable carbon and nitrogen atoms in said aromatic rings and/or said fused rings may be optionally and independently substituted with one, two, three or more of the following: halo, alkyl, aryl, cycloalkyl, cyano (—CN), —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

arylalkyl—represents an alkyl group, as defined above, wherein one or more hydrogen atoms of the alkyl moiety have been substituted with one or more aryl groups, as defined above (e.g. arylalkyl is benzyl or phenylethyl); wherein optionally, said arylalkyl group can be fused with one other aryl, cycloalkyl, heteroaryl or heterocycloalkyl ring provided that when the moiety "Z" in compound (1.0) is arylalkyl, the fused arylalkyl is a bicyclic ring (e.g napthalenyl) which is not a tricyclic or greater fused ring system; wherein said arylalkyl group may be optionally and independently substituted with one, two, three or more of the following: halo, alkyl, aryl, cycloalkyl, cyano (—CN), —$CF_3$, oxy (=O), —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

cycloalkyl-represents saturated carbocyclic rings branched or unbranched of from 3 to 20 carbon atoms, preferably 3 to 7 carbon atoms (e.g. cycloalkyl is cyclopropyl, cyclobutyl, cyclopentyl, cyclohexyl and the like); wherein said cycloalkyl ring optionally can be fused with one other cycloalkyl, cycloalkenyl or heterocycloalkyl ring to form a bicyclic ring which is not a tricyclic or greater fused ring system; wherein any of the available substitutable carbon and nitrogen atoms in said cycloalkyl ring and/or said fused ring may be optionally and independently substituted with one, two, three or more of the following: halo, alkyl, aryl, cycloalkyl, cyano (—CN), —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

cycloalkylalkyl—represents an alkyl group, as defined above, wherein one or more hydrogen atoms of the alkyl moiety have been substituted with one or more cycloalkyl rings as defined above; wherein said cycloalkylalkyl group may be optionally and independently substituted with one, two, three or more of the following: halo, alkyl, aryl, cycloalkyl, cyano (—CN), —$CF_3$, oxy (=O), —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

cycloalkenyl—represents a carbocyclic ring having one or two unsaturated bonds (i.e. carbon to carbon double bonds) and containing from 3 to 20 carbon atoms, preferably 3 to 7 carbon atoms wherein said one or two unsaturated bonds do not impart aromatic character to the cycloalkenyl ring; wherein said cycloalkenyl ring optionally can be fused with one other cycloalkyl, cycloalkenyl or heterocycloalkyl ring to form a bicyclic ring (e.g. norbornenyl) which is not a tricyclic or greater fused ring system; wherein any of the available substitutable carbon and nitrogen atoms in said cycloalkenyl ring and/or said fused ring may be optionally and independently substituted with one, two, three or more of the following: halo, alkyl, aryl, cycloalkyl, cyano (—CN), —CF$_3$, oxy (=O), —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove;

cycloalkenylalkyl—represents an alkyl group, as defined above, wherein one or more hydrogen atoms of the alkyl moiety have been substituted with one or more cycloalkenyl rings as defined above; wherein said cycloalkenylalkyl group optionally can be fused with one other cycloalkyl, cycloalkenyl or heterocycloalkyl ring to form a bicyclic ring (e.g. norbornylmethyl); wherein any of the available substitutable carbon and nitrogen atoms in said cycloalkenylalkyl group and/or said fused ring may be optionally and independently substituted with one, two, three or more of the following: halo, alkyl, aryl, cycloalkyl, cyano (—CN), —CF$_3$, oxy (=O), —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ areas defined hereinabove;

halo-represents fluoro, chloro, bromo and iodo;

heteroalkyl-represents straight and branched carbon chains containing from one to twenty carbon atoms, preferably one to six carbon atoms interrupted by 1 to 3 heteroatoms selected from —O—, —S— and —N—; wherein any of the available substitutable carbon and nitrogen atoms in said heteroalkyl chain may be optionally and independently substituted with one, two, three or more of the following: halo, alkyl, aryl, cycloalkyl, cyano (—CN), —CF$_3$, oxy (=O), —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove;

heteroaryl-represents cyclic groups having at least one heteroatom selected from O, S and N, said heteroatom(s) interrupting a carbocyclic ring structure and having a sufficient number of delocalized pi electrons to provide aromatic character, with the aromatic heterocyclic groups containing from 2 to 14 carbon atoms (e.g. heteroaryl is imidazoyl); wherein said heteroaryl group optionally can be fused with one aryl, cycloalkyl, heteroaryl or heterocycloalkyl ring to form a bicyclic ring which is not a tricyclic or greater fused ring system; and wherein any of the available substitutable carbon or nitrogen atoms in said heteroaryl group and/or said fused ring may be optionally and independently substituted with one, two, three or more of the following: halo, alkyl, aryl, arylalkyl, cycloalkyl, cyano (—CN), —CF$_3$, oxy (=O), —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove. Representative heteroaryl groups can include, for example, furanyl, imidazoyl, pyrimidinyl, triazolyl, 2-, 3- or 4-pyridyl or 2-, 3- or 4-pyridyl N-oxide wherein pyridyl N-oxide can be represented as:

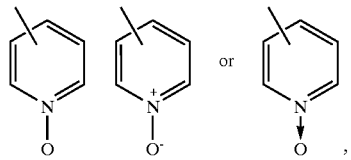

heteroarylalkyl—represents an alkyl group, as defined above, wherein one or more hydrogen atoms have been replaced by one or more heteroaryl groups; wherein said heteroaryl group optionally can be fused with one aryl, cycloalkyl, heteroaryl or heterocycloalkyl ring to form a bicyclic ring which is not a tricyclic or greater fused ring system; and wherein any of the available substitutable carbon or nitrogen atoms in said heteroaryl group and/or said fused ring may be optionally and independently substituted with one, two, three or more of the following: wherein said heteroarylalkyl group may be optionally and independently substituted with one, two, three or more of the following: halo, alkyl, aryl, cycloalkyl, cyano (—CN), —CF$_3$, oxy (=O), —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —CH$_2$NR$^{12}$COR$^{10}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove;

heterocycloalkyl-represents a saturated, branched or unbranched carbocylic ring containing from 3 to 15 carbon atoms, preferably from 4 to 6 carbon atoms, which carbocyclic ring is interrupted by 1 to 3 heteroatoms selected from —O—, —S— and —N—, wherein optionally, said ring may contain one or two unsaturated bonds which do not impart aromatic character to the ring; wherein said heterocycloalkyl group optionally can be fused with one aryl, cycloalkyl, heteroaryl or heterocycloalkyl ring to form a bicyclic ring which is not a tricyclic or greater fused ring system; and wherein any of the available substitutable carbon or nitrogen atoms in said heterocycloalkyl group and/or said fused ring may be optionally and independently and wherein any of the available substitutable carbon and nitrogen atoms in the ring may be optionally and independently substituted with one, two, three or more of the following: halo, alkyl, aryl, cycloalkyl, cyano (—CN), —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove. Representative heterocycloalkyl groups can include 2- or 3-tetrahydrofuranyl, 2- or 3-tetrahydrothienyl, 1-, 2-, 3- or 4-piperidinyl, 2- or 3-pyrrolidinyl, 1-, 2- or 3-piperizinyl, 2- or 4-dioxanyl, morpholinyl,

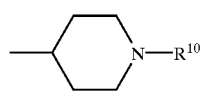

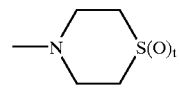

or
wherein $R^{10}$ is defined hereinbefore and t is 0, 1 or 2.

heterocycloalkalkyl—represents an alkyl group, as defined above, wherein one or more hydrogen atoms have been replaced by one or more heterocycloalkyl groups; wherein optionally, said ring may contain one or two unsaturated bonds which do not impart aromatic character to the ring; and wherein said heterocycloalkylalkyl group may be optionally and independently substituted with one, two, three or more of the following: halo, alkyl, aryl, cycloalkyl, cyano (—CN), —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove.

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purpopses of the invention.

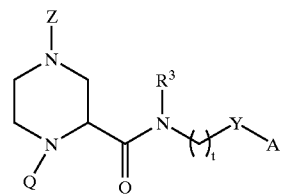

(1.0)

Compounds of the present invention can be prepared according to the following Schemes.

Library Preparation. A library of compounds is prepared by parallel synthesis. A generic structure of these compounds is shown in FIG. 1. The "A" group on the side chain histamine along with "Z" group on N-4 of the piperazine are varied in the library. Every member of the library contains methyl sulfonate at position N-1 of the piperazine core (FIG. 1).

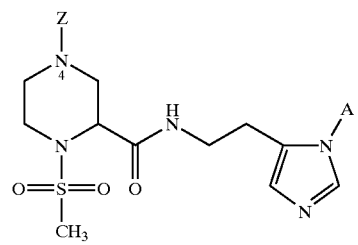

FIG. 1

SCHEME A

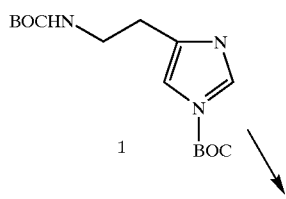

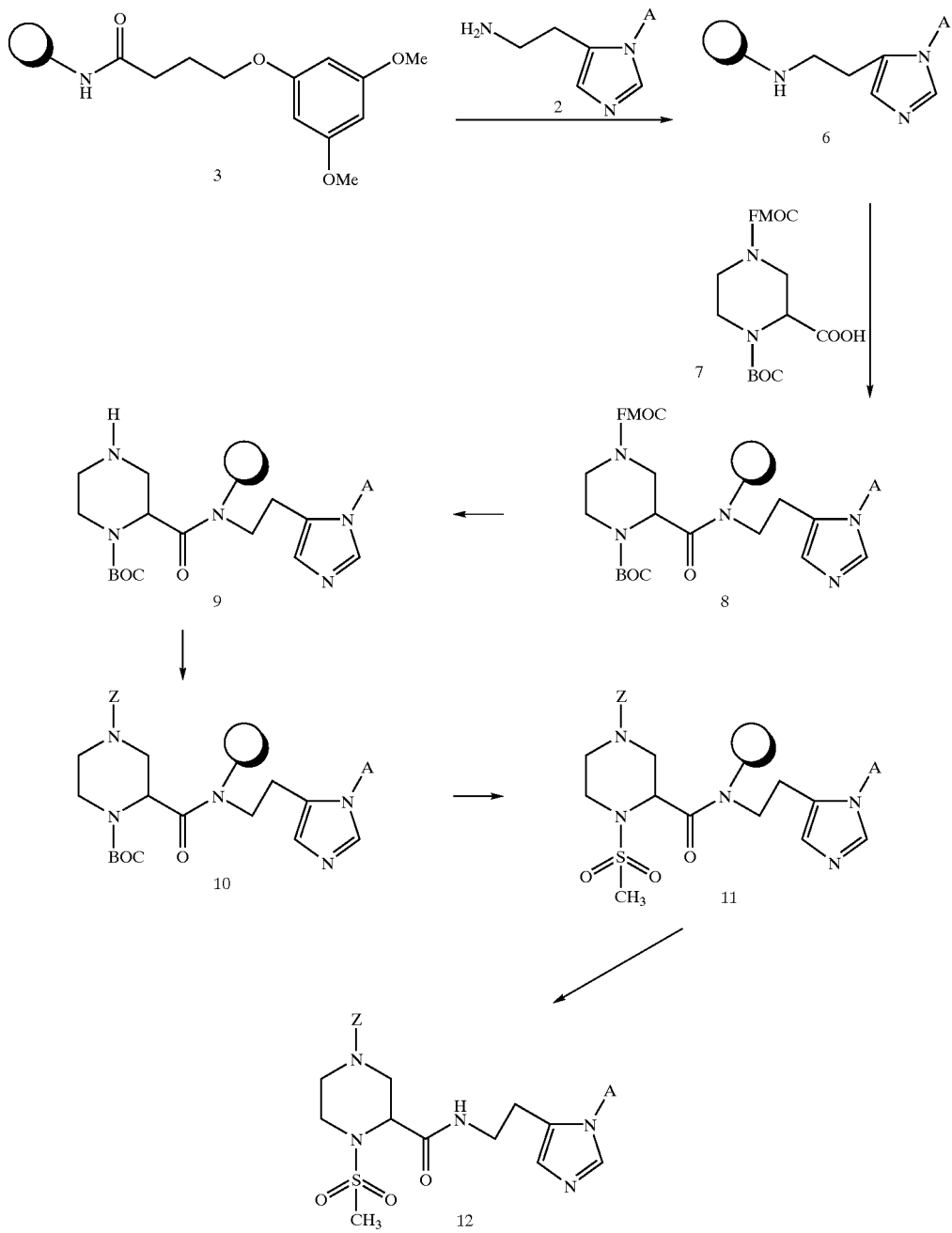

Referring to Scheme A, the side chain amines 2 were prepared by treating bis-Boc histamine 1 with the corresponding triflate, and subsequent removal of the Boc group. Library was prepared on TentaGel® (trademark of Rapp Inc., Germany) resin 3 functionalized with 4-(4-formyl-3-methoxyphenoxy)butyric acid 4 (shown in Scheme 1) to give functionalized resin 5. TentaGel resin is a composite of low-cross-linked polystrrene and polyethylene glycol, which has been terminally amino functionalized. Synthesis was initiated in Merrifield shaker vessels with reductive amination of the side chain amines 2 using the aldehyde of the acid cleavable linker of the functionalized resin 5 to give 6. This was followed by coupling N-4-Fmoc N-1-Boc piperazine carboxylic acid 7 with 6 to give 8. Removal of the Fmoc group of 8 gives 9. Resin 9 was dried and loaded into Robbins FlexChem block (96 wells) and subsequent reactions were performed in the block. Resin 9 was reductively alkylated with a number of corresponding aldehydes with NaBH$_3$CN in 2% HOAc in DMF or acylated with corresponding acid chlorides with lutidine in CH$_2$Cl$_2$ or sulfonyl chlorides with lutidine in CH$_2$Cl$_2$, or treated with isocyanates and DIPEA in CH$_2$Cl$_2$. Treatment of resin 10 with 10% HCl/MeOH followed by methanesulfonyl chloride gives resin 11. The product 12 is cleaved from resin 1 using trifluoroacetic acid.

Scheme 1
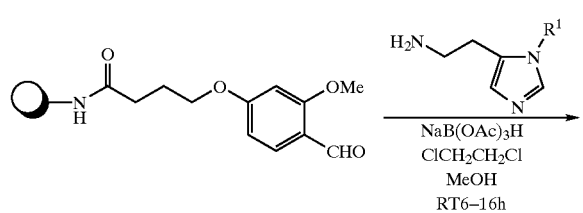
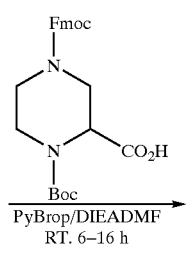
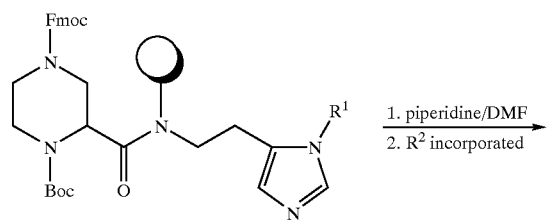
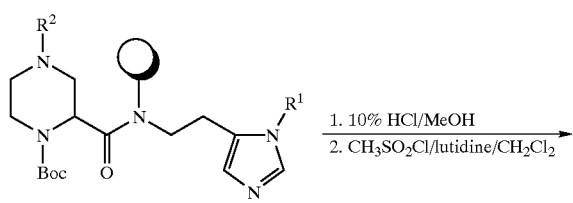
when R²      Reaction Conditions are:
= COR₃      R₃COCl, lutidine, CH₂Cl₂
= SO₂R₃      R₃SO₂Cl, lutidine, CH₂Cl₂
= CH₂R₃      R₃CHO, 2% HOAc/DMF, NaBH₃CN
= CONHR₃      R₃NCO, DIEA, CH₂Cl₂
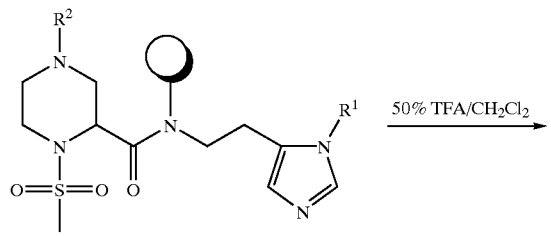
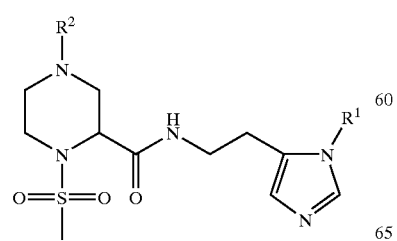
Scheme 2
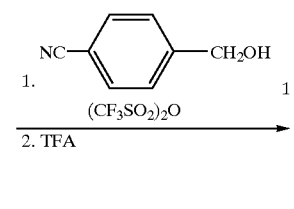
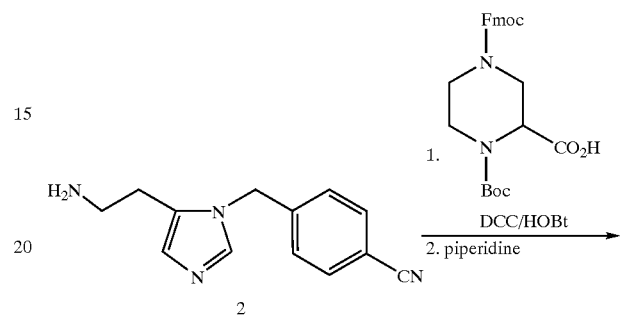
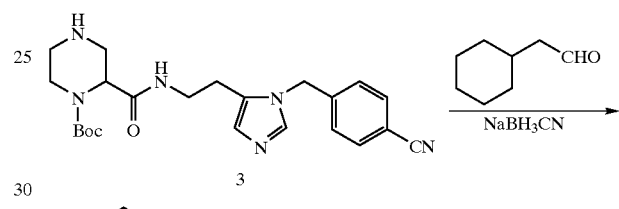
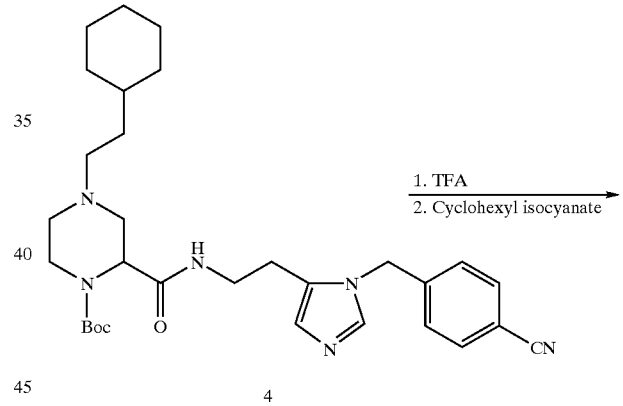
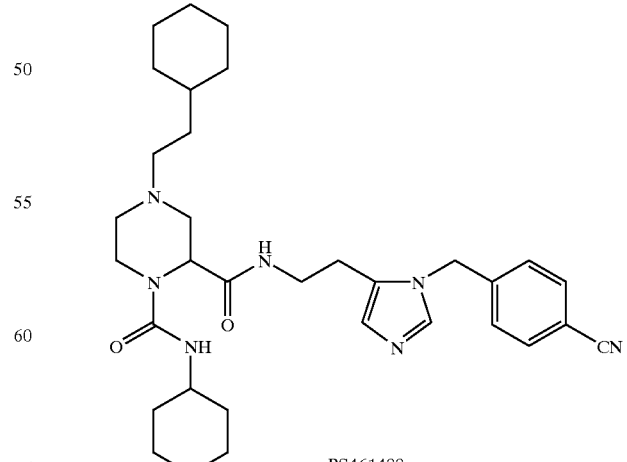
PS461400

Preparation Procedure for PS 461400 (Scheme 2)

1. Preparation of compound 2. To a stirred solution of triflic anhydride (1.9 mL, 11.3 mmole) in $CH_2Cl_2$ (35 mL) under Ar at −75° C. was added a solution of 4-cyanobenzyl alcohol (1)(1.37 g, 10.3 mmole) and diisopropylethylamine (1.97 mL, 11.3 mmole) in $CH_2Cl_2$ (12 mL) dropwise. Stirring at −78° C. was continued for 20 min. and a solution of N-Bis-Boc-histamine (3.2 g, 10.3 mmole) in $CH_2Cl_2$ (35 mL) was added. The reaction was allowed to warm to room temperature slowly and stirred overnight. The reaction mixture was washed with sat. $Na_2CO_3$ solution (30 mL). The organic phase was dried ($Na_2SO_4$) and solvent removed in vacuo. The residue was purified by column chromatography with 5 % MeOH in $CH_2Cl_2$ to give 1.38 g product in 41% yield. MS: m/z 327 ($MH^+$). This compound was treated with 25% trifluoroacetic acid in $CH_2Cl_2$ (20 mL) for 1 h. Solvent was removed in vacuo. The residue was dissolved in 5% HCl (15 mL) and washed with $CH_2Cl_2$ (10 mL×2). The aqueous layer was basified with NaOH to PH=9 and extracted with ethyl acetate (30 mL×4). The combined organic phase was dried ($Na_2SO_4$) and solvent removed in vacuo to give 600 mg desired amine 2 in 66% yield. MS: m/z 227 ($MH^+$).

2. Preparation of compound 3. To a stirred solution of the amine (2) (600 mg, 2.65 mmole) and N-4-Fmoc—N-1-Boc-piperazine carboxylic acid (1 g, 2.21 mmole) in $CH_2Cl_2$ (20 mL) was added DCC (547 mg, 2.65 mmole) and HOBt (358 mg, 2.65 mmole). The reaction was stirred overnight. The reaction mixture was filtered. The filtrate was washed with water (20 mL). The organic phase was dried ($Na_2SO_4$) and solvent removed in vacuo. The residue was purified by flash column chromatography with 5% MeOH in $CH_2Cl_2$ to give the amide. The amide was treated with 20% piperidine in $CHCl_3$ (10 mL) for 2 h. Solvent was removed in vacuo. The residue was purified by column chromatography with 5–10% MeOH in $CH_2Cl_2$ to give 713 mg desired amine in 74% yield. MS: m/z 439 ($MH^+$).

3. Preparation of compound 4. Amine 3 (40 mg, 0.09 mmole) was dissolved in MeOH (3 mL), cyclohexylacetaldehyde (23 µL, 0.18 mmole) and sodium cyanoborohydride (182 µL 1.0 M solution in THF, 0.18 mmole) was added. The reaction was stirred overnight. Solvent was removed in vacuo and the residue was purified by flash column chromatography with 3–5% MeOH in $CH_2Cl_2$ to give 22 mg of desired product in 44% yield. MS: m/z 549 ($MH^+$).

4. Preparation of PS461400. To a stirred solution of compound 4 (22 mg, 0.04 mmole) in $CH_2Cl_2$ (2 mL) was added trifluoroacetic acid (0.5 mL). The mixture was stirred for 1 h and solvent was removed in vacuo. The residue was pumped on a high vacuum line for 2 h and dissolved in $CH_2Cl_2$ (2 mL). To this solution was added diisopropylethyl amine (35 µL, 0.2 mmole) and the cyclohexyl isocyanate (28.5 µL, 0.2 mmole). The reaction was stirred overnight, dissolved in water (10 mL) and extracted with $CH_2Cl_2$ (15 mL×2). The organic layer was dried ($Na_2SO_4$) and solvent was removed in vacuo. The residue was purified by flash column chromatography with 4% MeOH in $CH_2Cl_2$ to give 11 mg desired product in 48% yield. MS: m/z 574 ($MH^+$).

Using substantially the same reaction scheme of the above example, with appropriate alcohol 1, the following compounds were prepared:

| | | | | |
|---|---|---|---|---|
| PS287238 | PS812520 | PS465781 | PS159773 | PS372802 |
| PS793961 | PS478500 | PS783003 | PS593455 | PS320451 |
| PS477090 | PS516972 | PS410892 | PS241936 | PS409643 |
| PS725556 | PS769295 | PS075114 | PS990951 | PS192638 |
| PS354164 | PS395570 | PS956973 | PS859989 | PS467023 |

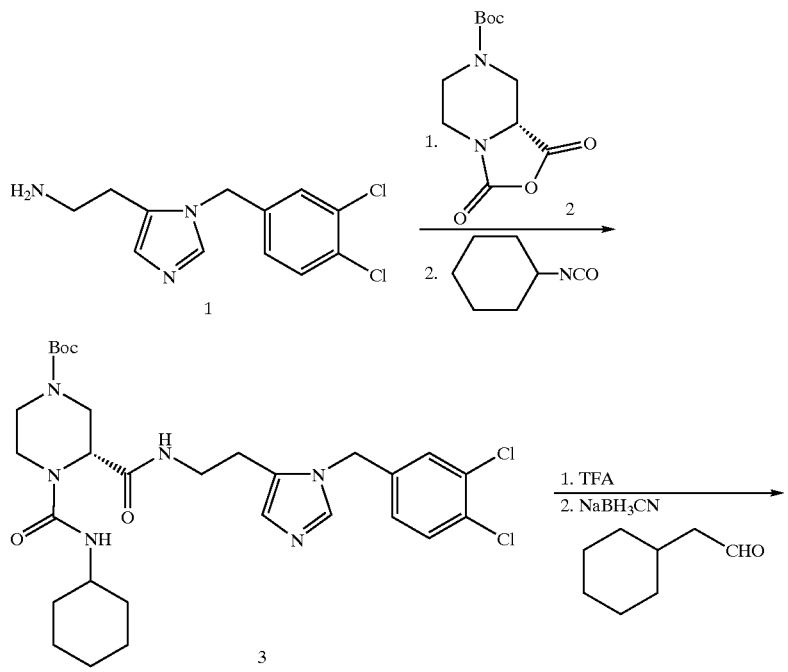

Scheme 3

Preparation Procedure for PS 321542 (Scheme 3)

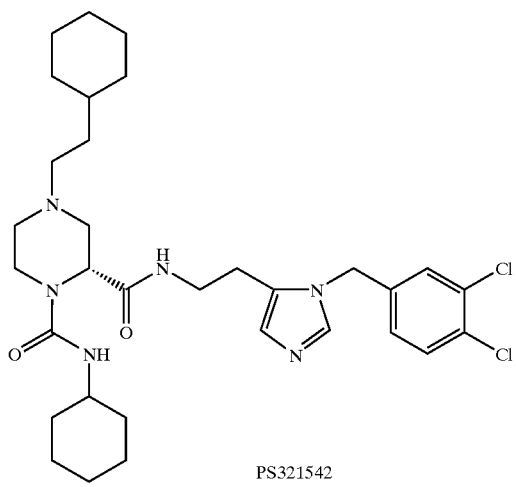

PS321542

1. Preparation of compound 3. To a stirred solution of the anhydride 1 (100 mg, 0.39 mmole) in CH$_2$Cl$_2$ (4 mL) was added a solution of the amine i (105 mg, 0.39 mmole) in a mixture of MeOH/CH$_2$Cl$_2$(0.5 mL/2 mL). The reaction was stirred for 1 h. The reaction was cooled to 0° C. and cyclohexyl isocyanate (111 μL, 0.78 mmole) was added. The reaction was stirred overnight. The reaction was partitioned between CH$_2$Cl$_2$ (40 mL) and sat. NaCl solution (20 mL). The organic layer was dried (Na$_2$SO$_4$) and solvent removed in vacuo to give 200 mg desired product in 85% yield. MS: m/z 607 (MH$^+$).

2. Preparation of compound PS321542. To a stirred solution of compound 3 (137 mg, 0.226 mmole) in CH$_2$Cl$_2$ (3 mL) was added trifluoroacetic acid (1 mL). The mixture was stirred for 1 h and solvent was removed in vacuo. The residue partitioned between 1 N NaOH (20 mL) and CH$_2$Cl$_2$ (20 mL). The aqueous layer was extracted with CH$_2$Cl$_2$ and EtOAc. The combined organic phase was dried (Na$_2$SO$_4$) and solvent was removed in vacuo. The amine was dissolved in MeOH (3 mL). To this solution was added cyclohexyl acetaldehyde (57 mg, 0.45 mmole) and sodium cyanoborohydride (1.0 M solution in THF, 452 μL, 0.45 mmole). The reaction was stirred overnight. Solvent was removed in vacuo and the residue partitioned between 1 N NaOH (20 mL) and CH$_2$Cl$_2$ (20 mL). The organic layer was dried (Na$_2$SO$_4$) and evaporated. The residue was purified by flash column chromatography with 4% MeOH in CH$_2$Cl$_2$ to give 52 mg product in 37% yield. MS: m/z 617 (M$^+$).

Using substantially the same reaction scheme of the above example, with racemic anhydride 2 when appropriate, the following compounds were prepared:

| PS815156 | PS288326 | PS130057 | PS064691 | PS028348 |
| PS813558 | PS319448 | PS420083 | PS259236 | PS437810 |
| PS381385 | PS201633 | | | |

Scheme 4

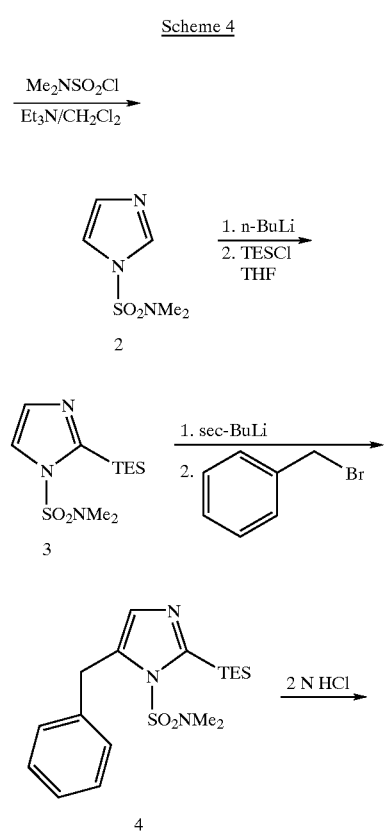

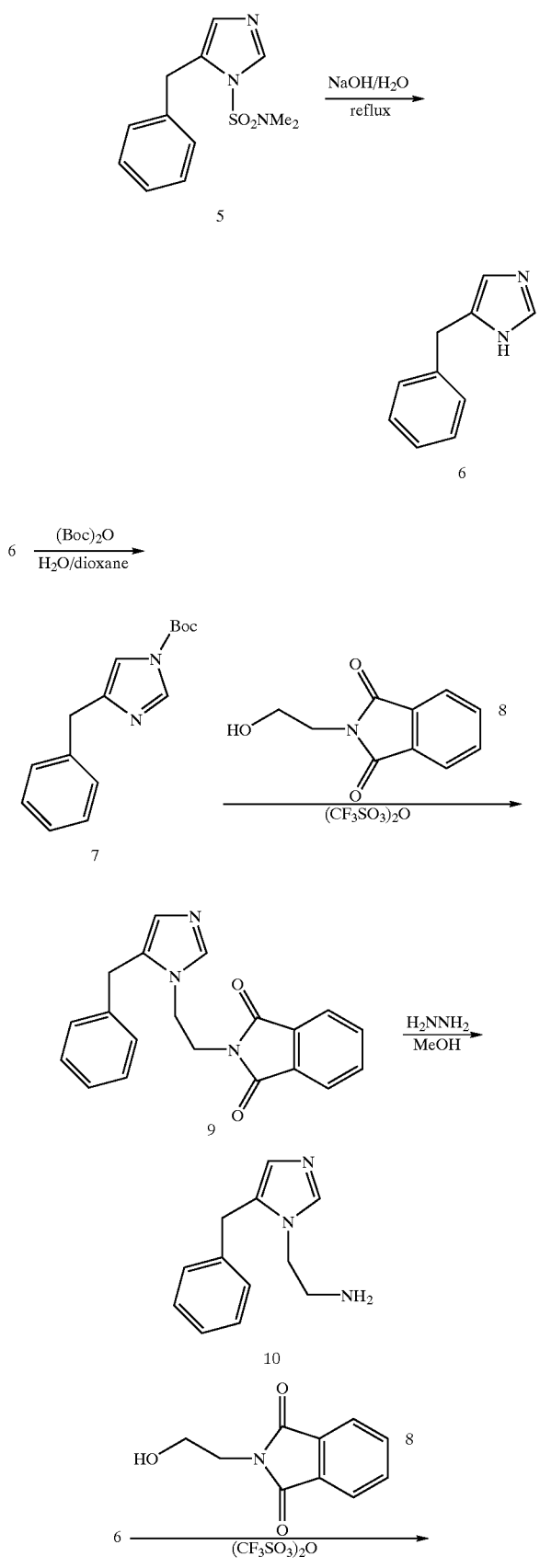
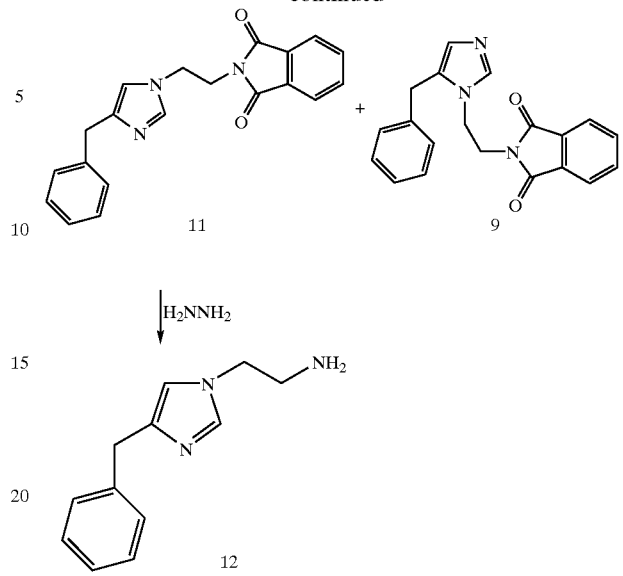

Preparation Procedure for 1-(2-Aminoethyl)-5-benzylimidazole (10) and 1-(2-Aminoethyl)-4-benzylimidazole (12) (Scheme 4)

1. Preparation of compound 2. To a stirred solution of imidazole (5g, 73.4 mmole) in $CH_2Cl_2$ (30 mL) at 0° C. was added triethylamine (15.4 mL, 110 mmole) and dimethylsulfamoyl chloride (8.3 mL, 77.1 mmole) dropwise. The reaction was allowed to warm to room temperature slowly and stirred overnight. The reaction was quenched with water (30 mL) and extracted with $CH_2Cl_2$ (30 mL×2). The organic phase was dried ($Na_2SO_4$) and solvent removed in vacuo to give compound 2 in 89% yield. MS: m/z 176 ($MH^+$).

2. Preparation of compound 5. To a stirred solution of compound 2 (1.0 g, 5.72 mmole) in THF (20 mL) at −78° C. under Ar was added n-BuLi in hexane (2.5 M solution, 2.44 mL, 6.12 mmole). The reaction mixture was stirred at at −78° C. for 30 min., and chlorotriethylsilane (1.92 mL, 11.44 mmole) was added. The reaction was stirred at room temperature for 5 h, then solvent and excess chlorosilane was removed under reduced pressure by gentle heating to give intermediate 3. THF (20 mL) was added to intermediate 3 and the solution was cooled to −78° C. Sec-butyllithium in cyclohexane (1.3 M solution, 8.8 mL, 11.44 mmole) was added and the mixture stirred at −78° C. for 30 min., then benzyl bromide (2.04 mL, 17.16 mmole) was added. Stirring was continued at −78° C. for 30 min., and at room temperature overnight. Solvent was removed in vacuo to give intermediate 4. Intermediate 4 was stirred with 2 N HCl (50 mL) for 3 h and the mixture was washed with ether (20 mL×2). The aqueous phase was basified with NaOH (40% w/w) to pH=11, then extracted with ether (50 mL×3). Combined organic phase was dried ($Na_2SO_4$) and solvent removed in vacuo. The residue was purified by flash column chromatography with 35% hexane in EtOAc to give 560 mg compound 5 in 37% yield. MS: m/z 266 ($MH^+$).

3. Preparation of compound 6. Compound 5 (560 mg, 2.11 mmole) was refluxed in 4% NaOH (w/w, 100 mL) overnight. Solvent was removed in vacuo. The residue was triturated with THF, filtered and dried ($Na_2SO_4$). Solvent was removed under reduced pressure to give 240 mg 4(5)-benzylimidazole (6) in 72% yield. MS: m/z 159 ($MH^+$).

4. Preparation of 1-(2-Aminoethyl)-5-benzylimidazole (10). To a stirred solution of compound 6 (230 mg, 1.45 mmole) in $H_2O$/dioxane (1:1, 20 mL) was added sodium carbonate (31 mg, 0.29 mmole) and di-t-butyl-dicarbonate (400 mg, 1.74 mmole). The mixture was stirred overnight, then extracted with $CH_2Cl_2$ (40 mL×2). Combined organic layer was washed with water (20 mL), dried ($Na_2SO_4$) and solvent was removed in vacuo to give 305 mg compound 7 in 82% yield. MS: m/z 259 ($MH^+$). To a stirred solution of triflic anhydride (219 µL, 1.3 mmole) in $CH_2Cl_2$ (5 mL) under Ar at −78° C. was added a solution of compound 8 (249 mg, 1.3 mmole) and DIEA in $CH_2Cl_2$ (5 mL). Stirring at −78° C. was continued for 20 min., a solution of compound 7 in $CH_2Cl_2$ (5 mL) was added dropwise. The reaction was allowed to gradually warm to room temperature overnight. To the reaction was added sat. $NaHCO_3$ (10 mL). The mixture was extracted with $CH_2Cl_2$ (20 mL×2). Organic layer was washed with water (10 mL), dried ($Na_2SO_4$) and solvent removed in vacuo. The residue was purified by column chromatography with 1-5 % MeOH in $CH_2Cl_2$ to give 60 mg compound 9. MS: m/z 332 ($MH^+$). Compound 9 was dissolved in MeOH (2 mL) and hydrazine (10 µL) was added. The reaction was stirred overnight and solvent was removed in vacuo. The residue was dissolved in 0.1 N HCl (10 mL) and washed with EtOAc (10 mL). The aqueous phase was basified with NaOH until pH=11, and extracted with EtOAc (20 mL×3). Combined organic layer was dried ($Na_2SO_4$) and solvent removed in vacuo to give the title compound 10. MS: m/z 202 ($MH^+$).

5. Preparation of 1-(2-Aminoethyl)-4-benzylimidazole (12). To a stirred solution of triflic anhydride (245 µL, 1.46 mmole) in $CH_2Cl_2$ (5 mL) under Ar at −78° C. was added a solution of compound 8 (278 µg, 1.46 mmole) and DIEA in $CH_2Cl_2$ (5 mL). Stirring at −78° C. was continued for 20 min., a solution of compound 6 in $CH_2Cl_2$ (5 mL) was added dropwise. The reaction was allowed to gradually warm to room temperature overnight. To the reaction was added sat. $NaHCO_3$ (10 mL). The mixture was extracted with $CH_2Cl_2$ (20 mL×2). Organic layer was washed with water (10 mL), dried ($Na_2SO_4$) and solvent removed in vacuo. The residue was purified by column chromatography with 1–5% MeOH in $CH_2Cl_2$ to give 112 mg compound 11. MS: m/z 332 ($MH^+$). Compound 11 was dissolved in MeOH (2 mL) and hydrazine (10 µL) was added. The reaction was stirred overnight and solvent was removed in vacuo. The residue was dissolved in 0.1 N HCl (10 mL) and washed with EtOAc (10 mL). The aqueous phase was basified with NaOH until pH=11, and extracted with EtOAc (20 mL×3). Combined organic layer was dried ($Na_2SO_4$) and solvent removed in vacuo to give the title compound 12. MS: m/z 202 ($MH^+$).

Compound 10 was used to prepare PS319448 using procedure described in scheme 2. Compound 12 was used to prepare PS204446 using procedure described in scheme 2.

Reagents and reaction conditions for protecting and deprotecting compounds is well known, as described, for example, in T. W. Greene and P. Wuts, Protective Groups in Organic Synthesis, 2nd Ed., Wiley Interscience, N.Y. 1991, 473 pages.

Compounds of the present invention and preparative starting materials therof, are exemplified by the following examples, which should not be construed as limiting the scope of the disclosure. Alternative mechanistic pathways and analogous structures within the scope of the invention may be apparent to those skilled in the art, such as by the methods described in WO95/10516.

Compounds of formula (1.0) can be isolated from the reaction mixture using conventional procedures, such as, for example, extraction of the reaction mixture from water with organic solvents, evaporation of the organic solvents, followed by chromatography on silica gel or other suitable chromatographic media. Alternatively, compounds (1.0) can be dissolved in a water-miscible solvent, such as methanol, the methanol solution is added to water to precipitate the compound, and the precipitate is isolated by filtration or centrifugation.

Compounds of the present invention and preparative starting materials thereof, are exemplified by the following examples, which should not be construed as limiting the scope of the disclosure.

EXAMPLE 1

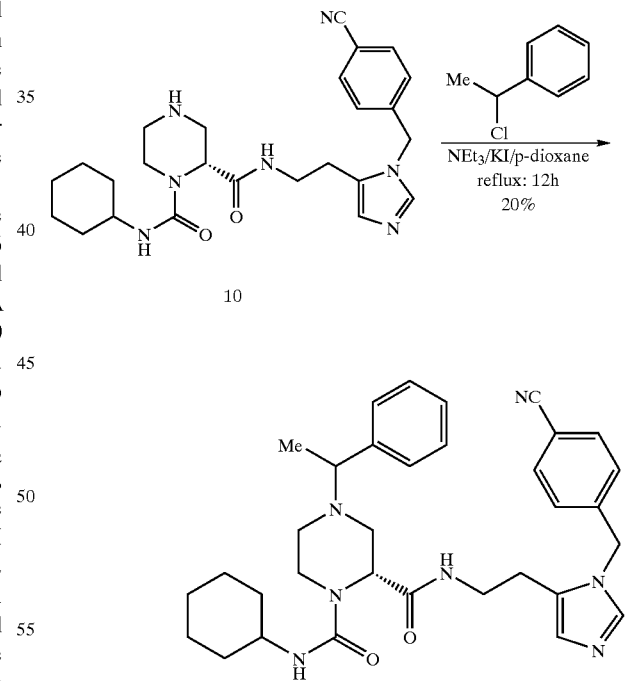

A solution of 10 (50 mg, 0.108 mmol, 1.0 eq.), 1-chloro-1-phenylethane (170 µl, 1.29 mmol, 12.0 eq.), and triethylamine (180 µl, 1.29 mmol, 12.0 eq.) in anhydrous p-dioxane (10 ml) is gently refluxed at 105 ° C. under a nitrogen atmosphere for 12 h. The solution is cooled to room temperature and the volatiles are removed under vacuum at 30 ° C. The residue is taken up in distilled water (10 ml) and extracted with dichloromethane (5×5 ml). The combined organic extracts are washed with brine (5 ml), dried over NA$_2$SO$_4$, filtered, and concentrated under vacuum at 30 ° C. N2-[2-[1-[(4-cyanophenyl)methyl]-1H-imidazol-5-yl]ethyl]-N1-cyclohexyl-4-(1-phenylethyl)-1,2(R)-piperazinedicarboxamide (12 mg, 0.021 mmol, 20%) is obtained as a light-yellow semi-solid after preparative scale thin layer chromatography (CH$_3$CN: 2 N NH$_3$/MeOH=90: 10 v/v as eluent) over silica gel.

HR-MS (FAB):

Calculated for C$_{33}$H$_{42}$N$_7$O$_2$ ([M+H]$^+$): 568.3400. Found: 568.3407.

EXAMPLE 2

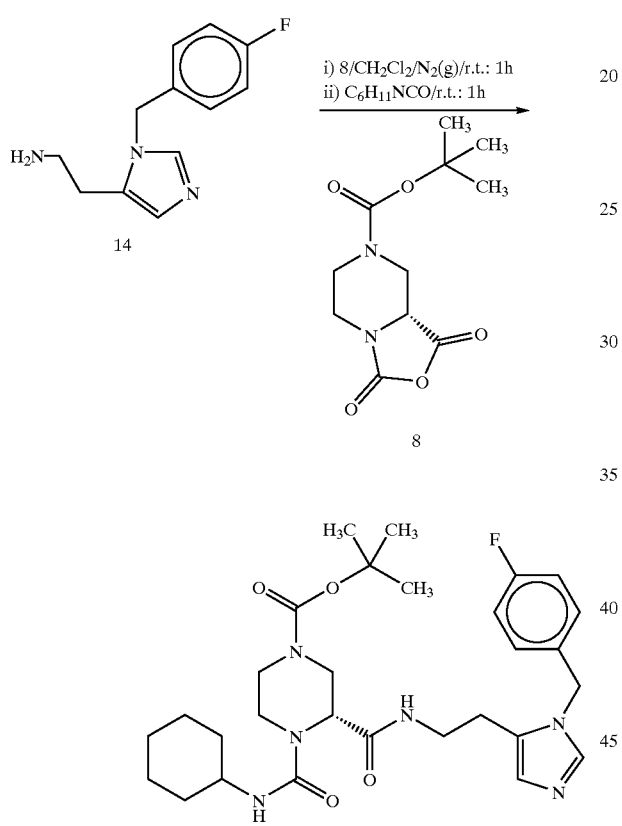

A solution of 14 (500 mg, 2.28 mmol, 1.0 eq.) in anhydrous dichloromethane (5 ml) was added dropwise over a period of 5 minutes to a stirred solution of anhydride 8 (701 mg, 2.74 mmol, 1.2 eq.) in anhydrous dichloromethane (10 ml) at room temperature. A stream of nitrogen was bubbled through the solution to expel evolved carbon dioxide. The colorless solution was stirred for one hour amid nitrogen bubbling. Bubbling was terminated and cyclohexyl isocyanate (594 ml, 4.56 mmol, 2.0 eq.) was added dropwise over a period of 5 minutes. The light-yellow solution was stirred at room temperature for one hour. The volatiles were removed under vacuum at 30° C. The resulting viscous oil was partitioned between dichloromethane (25 ml) and 1 N aqueous NaOH solution (25 ml). The aqueous layer was extracted with dichloromethane (3×10 ml). The combined organic extracts were washed with brine (5 ml), dried over Na$_2$SO$_4$, filtered, and concentrated under vacuum at 30° C. Preparative scale thin layer chromatography (CH$_2$Cl$_2$: 2 N NH$_3$/MeOH=90: 10 v/v) over silica gel afforded 1,1-dimethylethyl-1-[(cyclohexylamino)carbonyl]-2(R)-[[[2-[1-(4-fluorophenyl)methyl]-1H-imidazol-5-yl]ethyl]amino]carbonyl]-4-piperazinecarboxylate (190 mg, 0.34 mmol, 15%) as an off-white foam.

Melting Point: 72° C. (decomposition).

MS (FAB+): m/e 557 ([M+H]$^+$).

HR-MS (FAB):

Calculated for C$_{29}$H$_{42}$FN$_6$O$_4$ ([M+H]$^{+)}$: 557.3252. Found: 557.3240.

EXAMPLE 3

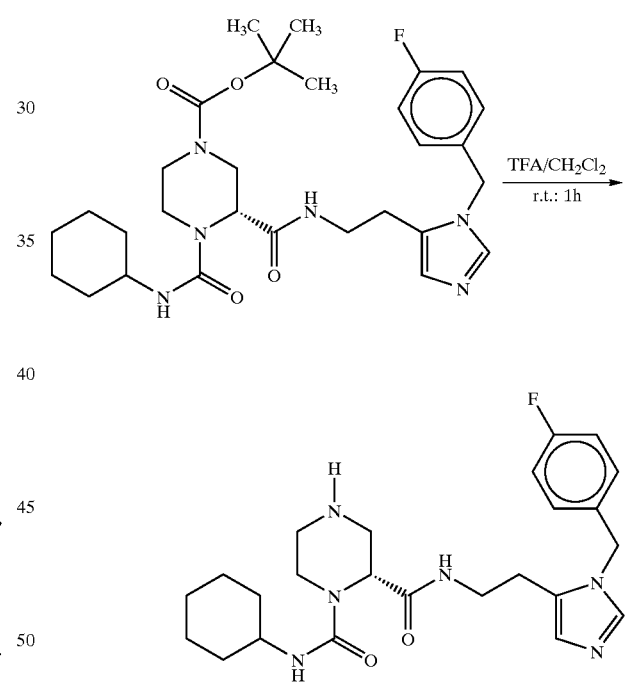

The title compound of Example 2 (190 mg, 0.34 mmol, 1.0 eq.) was dissolved in a mixture of anhydrous dichloromethane (10 ml) and trifluoroacetic acid (10 ml). The resulting yellow solution was stirred at ambient temperature under a nitrogen atmosphere for one hour. The volatiles were evaporated under vacuum at 30° C. and the remaining viscous oil was directly flash chromatographed (CH$_2$Cl$_2$: 2 N NH$_3$/MeOH=90: 10 v/v) over silica gel to give N2-[2-[1-[(4-fluorophenyl)methyl]-1H-imidazol-5-yl]ethyl]-N1-cyclohexyl-1,2(R)-piperazinecarboxamide (121 mg, 0.27 mmol, 78%) as an off-white solid.

EXAMPLE 4

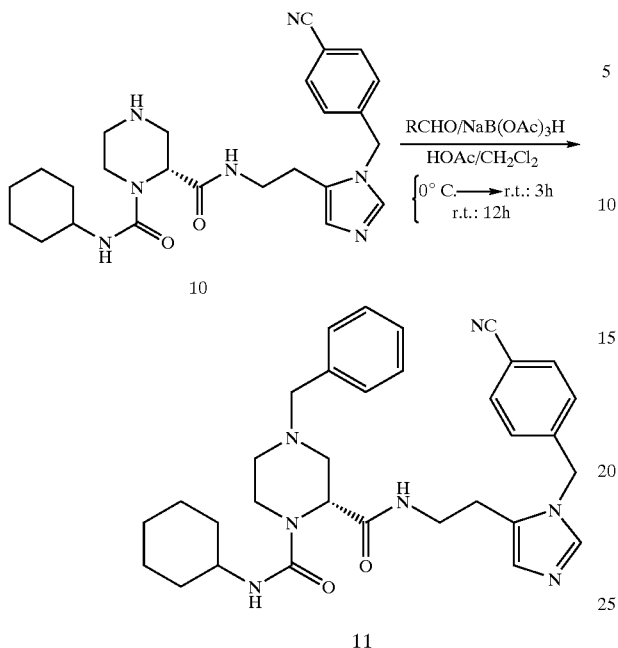

Sodium triacetoxyborohydride (75 mg, 0.336 mmol, 3.1 eq.) is added portionwise (3×25 mg) to a stirred solution of 10 (50 mg, 0.108 mmol, 1.0 eq.) and benzoic aldehyde (R=phenyl) (0.336 mmol, 3.1 eq.) in a mixture of glacial acetic acid (0.5 ml) and anhydrous dichloromethane (10 ml) at 0° C. under a nitrogen atmosphere. The mixture is slowly (3 h) warmed to room temperature and stirred for another 12 h. The volatiles are removed under vacuum at 30° C. The residue is taken up in 1 N aqueous NaOH solution (10 ml) and extracted with dichloromethane (5×5 ml). The combined organic extracts are washed with brine (5 ml), dried over $Na_2SO_4$, filtered, and concentrated under vacuum at 25° C. The product is obtained after preparative scale thin layer chromatography (using either $CH_2Cl_2$: 2 N $NH_3$/MeOH=90: 10 v/v or $CH_3CN$: 2 N $NH_3$/MeOH=90: 10 v/v as eluent) over silica gel.

In Examples 5–28 by following essentially the same procedure as described in Example 4, except that the corresponding aldehyde is substituted for benzoic aldehyde, the title compound is obtained.

EXAMPLE 5

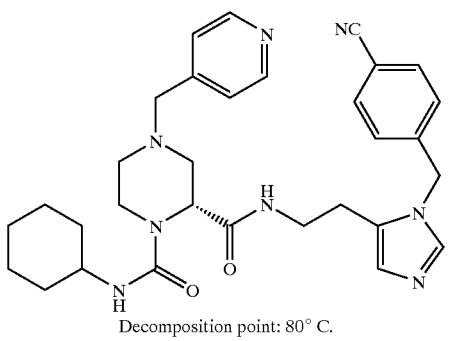

Decomposition point: 80° C.

EXAMPLE 6

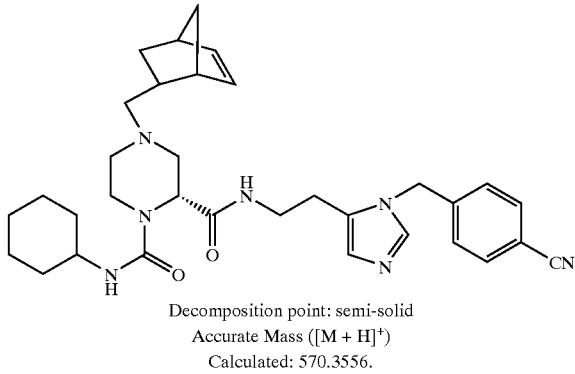

Decomposition point: semi-solid
Accurate Mass ($[M + H]^+$)
Calculated: 570.3556.
Found: 570.3570.

EXAMPLE 7

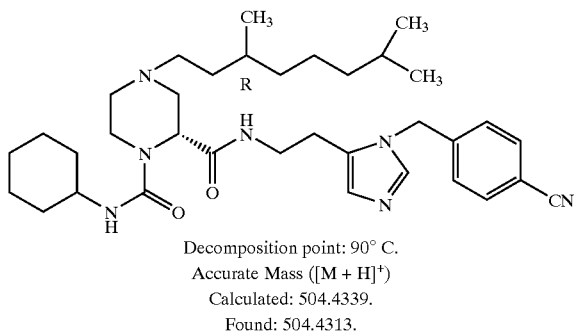

Decomposition point: 90° C.
Accurate Mass ($[M + H]^+$)
Calculated: 504.4339.
Found: 504.4313.

EXAMPLE 8

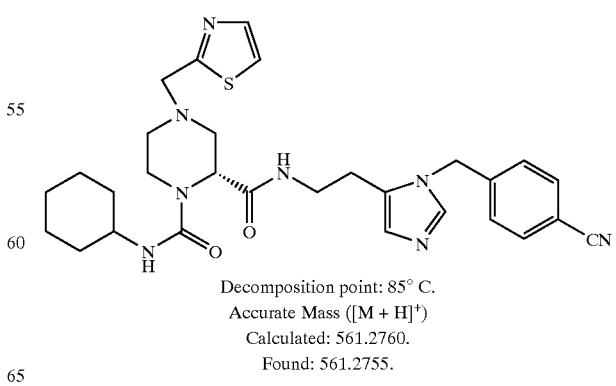

Decomposition point: 85° C.
Accurate Mass ($[M + H]^+$)
Calculated: 561.2760.
Found: 561.2755.

EXAMPLE 9

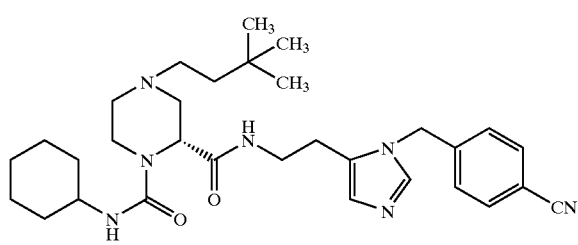

Decomposition point: 65° C.
Accurate Mass ([M + H]$^+$)
Calculated: 548.3713.
Found: 548.3712.

EXAMPLE 10

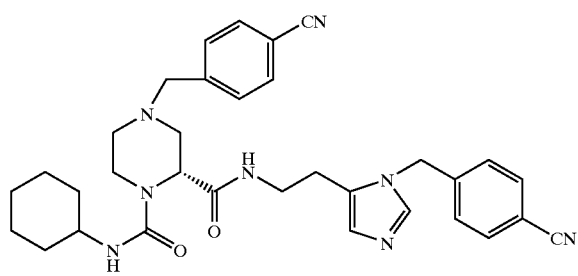

Decomposition point: 155° C.
Accurate Mass ([M + H]$^+$)
Calculated: 579.3196.
Found: 579.3200.

EXAMPLE 11

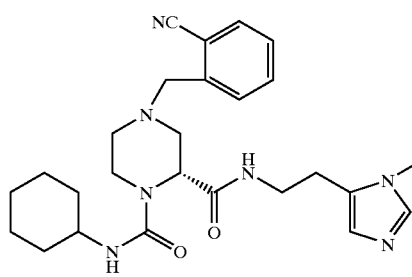

Decomposition point: 95° C.
Accurate Mass ([M + H]$^+$)
Calculated: 579.3196.
Found: 579.3189.

EXAMPLE 12

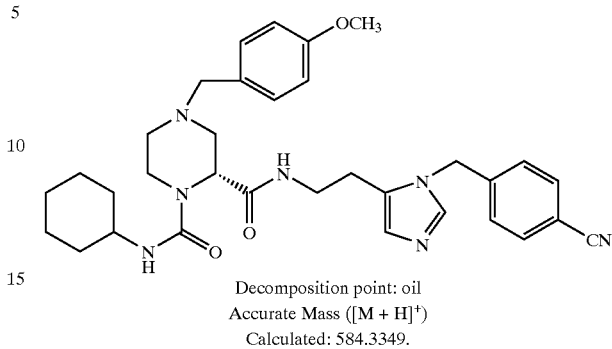

Decomposition point: oil
Accurate Mass ([M + H]$^+$)
Calculated: 584.3349.
Found: 584.3352.

EXAMPLE 13

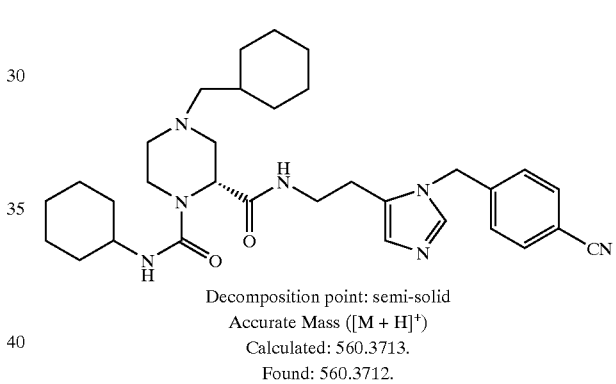

Decomposition point: semi-solid
Accurate Mass ([M + H]$^+$)
Calculated: 560.3713.
Found: 560.3712.

EXAMPLE 14

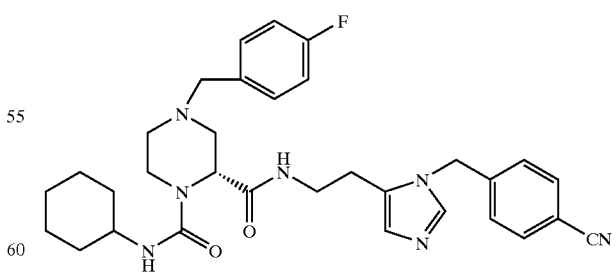

Decomposition point: semi-solid
Accurate Mass ([M + H]$^+$)
Calculated: 572.3149.
Found: 572.3145.

EXAMPLE 15

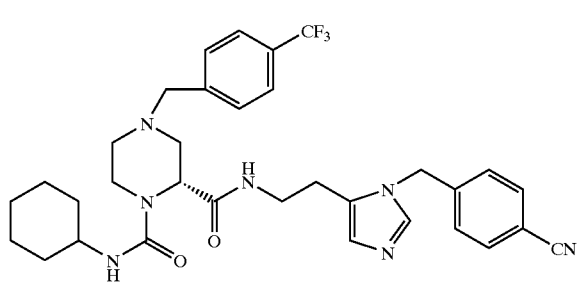

Decomposition point: 165° C.
Accurate Mass ([M + H]+)
Calculated: 622.3117.
Found: 622.3134.

EXAMPLE 16

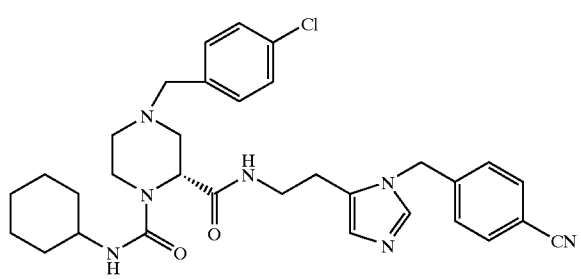

Decomposition point: 180° C.
Accurate Mass ([M + H]+)
Calculated: 588.2854.
Found: 588.2850.

EXAMPLE 17

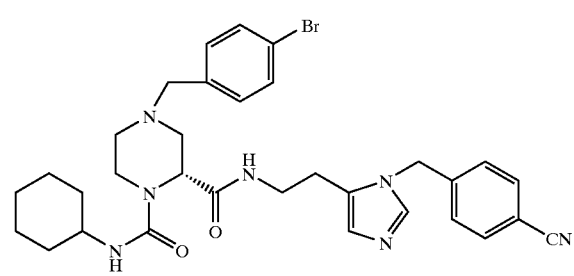

Decomposition point: semi-solid
Accurate Mass ([M + H]+)
Calculated: 632.2349.
Found: 632.2334.

EXAMPLE 18

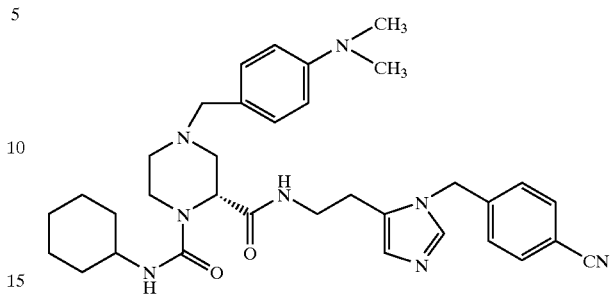

Decomposition point: oil
Accurate Mass ([M + H]+)
Calculated: 597.3665.
Found: 597.3653.

EXAMPLE 19

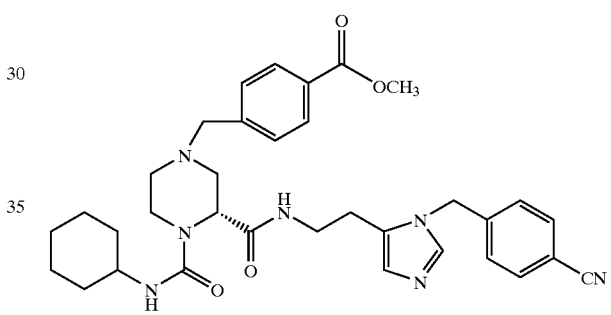

Decomposition point: 205° C.
Accurate Mass ([M + H]+)
Calculated: 612.3298.
Found: 612.3308.

EXAMPLE 20

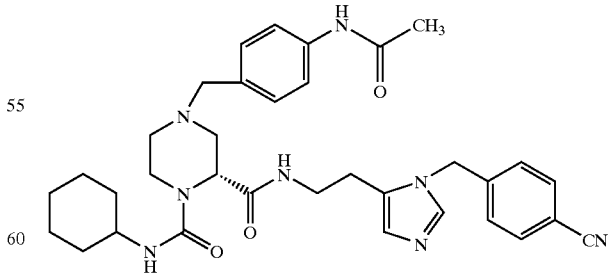

Decomposition point: 120° C.
Accurate Mass ([M + H]+)
Calculated: 611.3458.
Found: 611.3474.

EXAMPLE 21

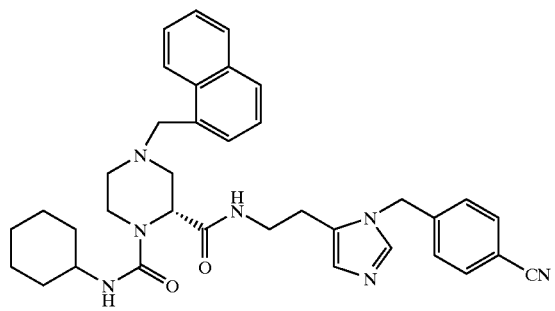

Decomposition point: 100° C.
Accurate Mass ([M + H]⁺)
Calculated: 611.3400.
Found: 611.3424.

EXAMPLE 22

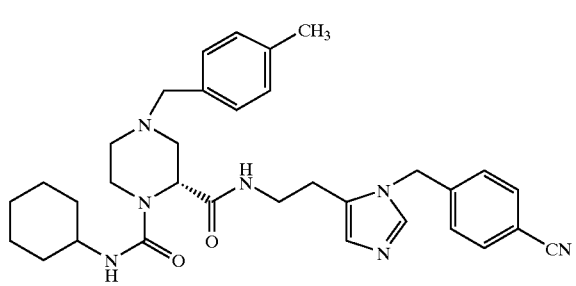

Decomposition point: 185° C.
Accurate Mass ([M + H]⁺)
Calculated: 568.3400.
Found: 568.3410.

EXAMPLE 23

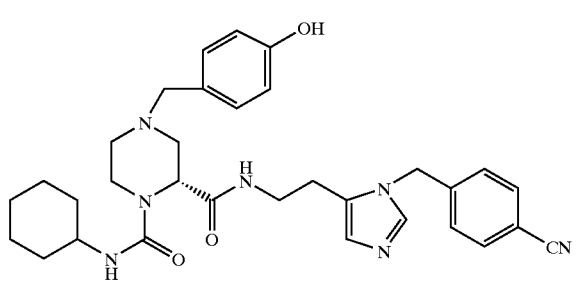

Decomposition point: semi-solid
Accurate Mass ([M + H]⁺)
Calculated: 570.3193.
Found: 570.3194.

EXAMPLE 24

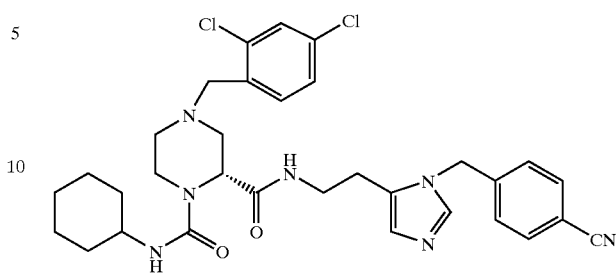

Decomposition point: 185° C.
Accurate Mass ([M + H]⁺)
Calculated: 622.2464.
Found: 622.2452.

EXAMPLE 25

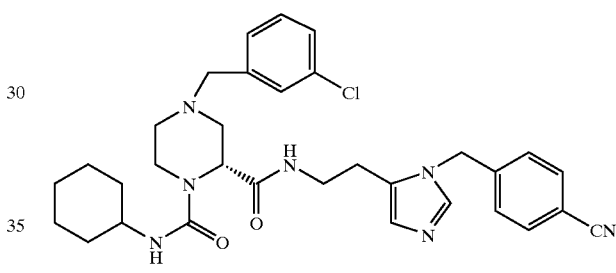

Decomposition point: 130° C.
Accurate Mass ([M + H]⁺)
Calculated: 588.2854.
Found: 588.2857.

EXAMPLE 26

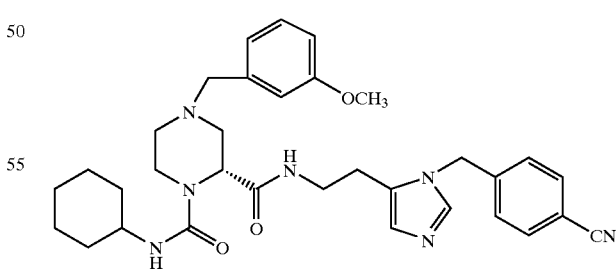

Decomposition point: 160° C.
Accurate Mass ([M + H]⁺)
Calculated: 584.3349.
Found: 584.3347.

EXAMPLE 27

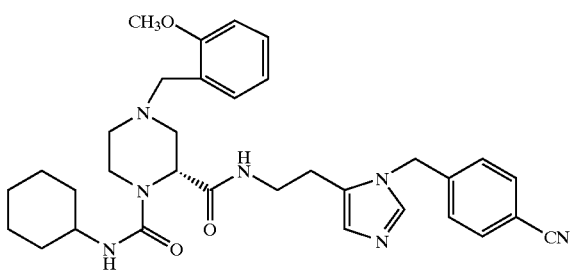

Decomposition point: 130° C.
Accurate Mass ([M + H]$^+$)
Calculated: 584.3349.
Found: 584.3356.

EXAMPLE 28

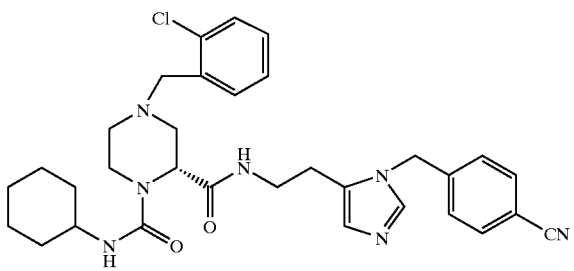

Decomposition point: 110° C.
Accurate Mass ([M + H]$^+$)
Calculated: 588.2854.
Found: 588.2844.

By using the title compounds of Example 3 and by following essentially the same procedure as described in Example 4, the following compounds are prepared.

EXAMPLE 28A

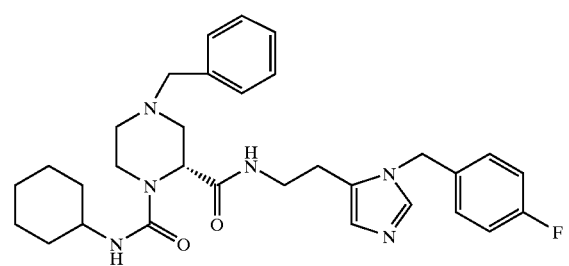

Decomposition point: 155° C.
Accurate Mass ([M + H]$^+$)
Calculated: 547.3197
Found: 547.3192

EXAMPLE 28B

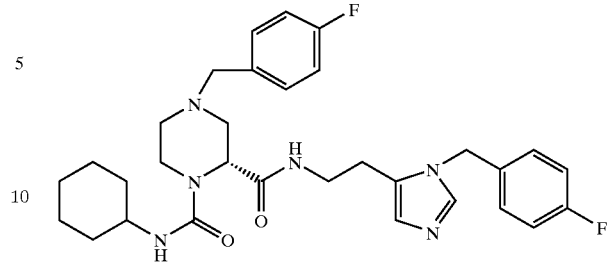

Decomposition point: 165° C.
Accurate Mass ([M + H]$^+$)
Calculated: 565.3103
Found: 565.3106

EXAMPLE 28C

N4-phenylmethyl-N2-[2-[1-[(4-chlorophenyl)methyl]-1H-imidazol-5-yl]ethyl]-N1-cyclohexyl-1,2(R)-piperazinedicarboxamide

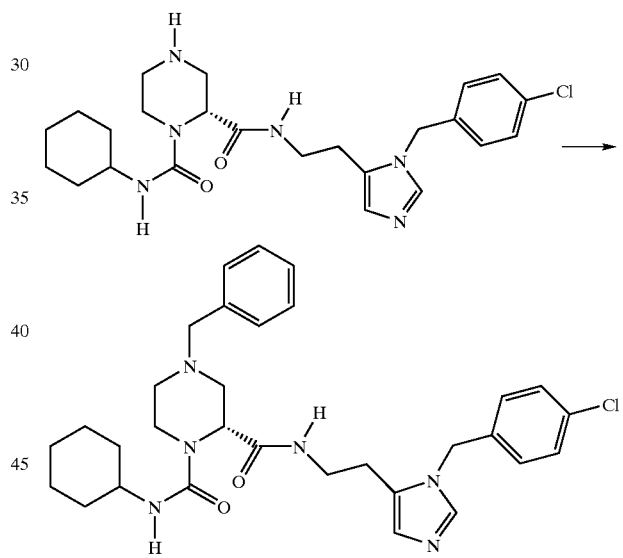

To the title compound from Preparative Example 12 (75 mg, 0.16 mmol) and benzaldehyde (0.05 mL, 0.5 mmol) dissolved in glacial acetic acid (0.5 mL) and anhydrous dichloromethane (10 ml) at 0° C., is added sodium triacetoxyborohydride (102 mg, 0.5 mmol) and the resulting mixture is warmed to room temperature and stirred for an additional 12 hours. The reaction mixture is concentrated in vacuo, diluted with dichloromethane and washed with 1 N NaOH (aq). The organic phase is dried over anhydrous MgSO$_4$, filtered, concentrated in vacuo, and purified by preparative plate chromatography (silica gel) using 7% MeOH (saturated with ammonia 2M)—CH$_3$CN as eluent to afford the title compound as a white solid (60 mg, MH$^+$= 563, mp=116.2° C.).

EXAMPLE 28D

N4-phenylmethyl-N2-[2-[1-(phenylethyl)-1H-imidazol-5-yl]ethyl]-N1-cyclohexyl-1,2(R)-piperazinedicarboxamide

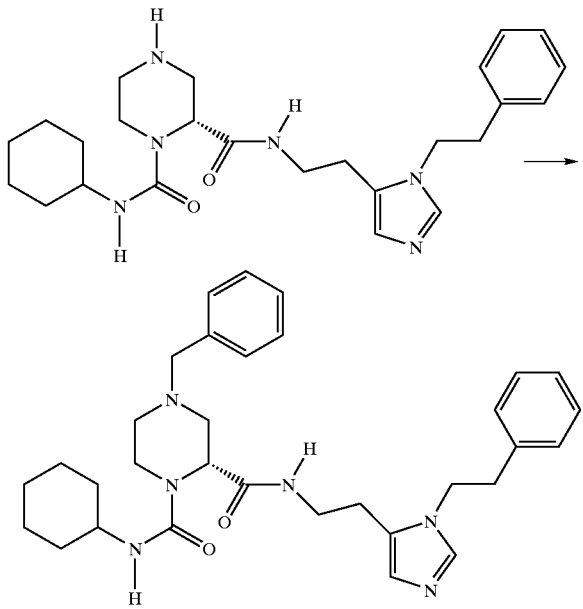

To the title compound from Preparative Example 12A (75 mg, 0.17 mmol) and benzaldehyde (0.05 mL, 0.5 mmol) dissolved in glacial acetic acid (0.5 mL) and anhydrous dichloromethane (10 ml) at 0° C. is added sodium triacetoxyborohydride (108 mg, 0.5 mmol) and the resulting mixture is warmed to room temperature and stirred for an additional 12 h. The reaction mixture is concentrated in vacuo, diluted with dichloromethane and washed with 1 N NaOH (aq). The organic phase is dried over anhydrous MgSO$_4$, filtered, concentrated in vacuo, and purified by preparative plate chromatography (silica gel) using 7% MeOH (saturated with ammonia 2M)—CH$_3$CN as eluent to afford the title compound as a white solid (61 mg, MH$^+$= 543, mp=64.4° C.).

EXAMPLE 28E

N-[2-[1-[(4-cyanophenyl)methyl]-1H-imidazol-5-yl]ethyl]-1-(1-oxopropyl)-4-phenyl(methyl)-2(R)-piperazinedicarboxamide

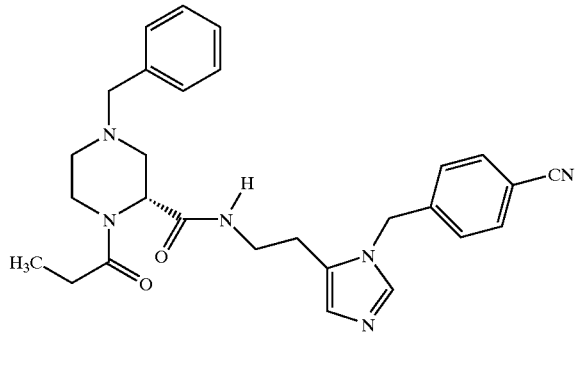

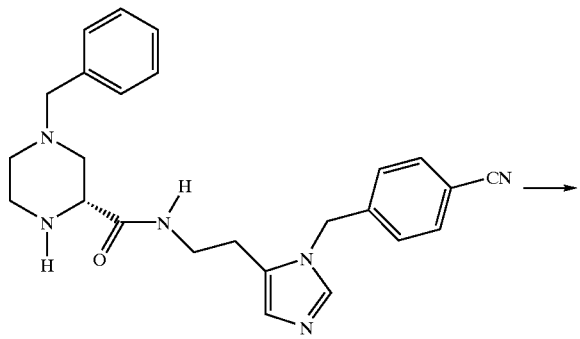

To a solution of the title compound from Preparative Example 11 (50 mg, 0.12 mmol, 1.0 eq) and triethylamine (33 mL, 0.24 mmol) in anhydrous dichloromethane (2 ml) is added propionyl chloride (15.2 mL, 0.18 mmol). The resulting mixture is stirred at room temperature under N$_2$ for 48 hrs and then quenched with saturated NaHCO$_3$(aq) solution. The mixture is extracted with dichloromethane and dried over anhydrous Na$_2$SO$_4$. The organic phase is filtered, concentrated in vacuo, and the residue purified by preparative plate chromatography (silica gel) using 6% methanol-dichloromethane saturated with ammonium hydroxide to afford the title compound as an off-white solid (38.1 mg, mp=88.2–168.6° C., MH+=485).

EXAMPLE 28F

N-[2-[1-[(4-cyanophenyl)methyl]-1H-imidazol-5-yl]ethyl]-1-(1-oxobutyl)-4-phenyl(methyl)-2(R)-piperazinedicarboxamide

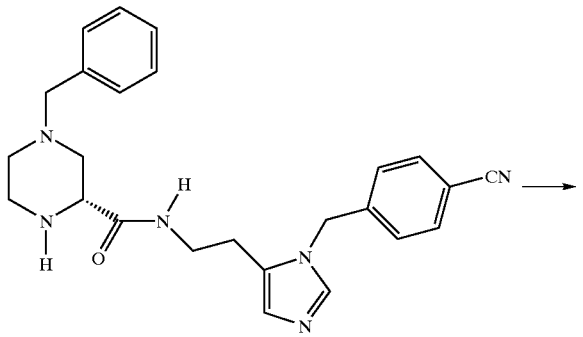

In a similar manner as is described in Example 28E, but using butyryl chloride instead of propionyl chloride, the title compound is prepared as an off-white solid (34.3 mg, mp=82.32–142.5° C., MH+=499).

EXAMPLE 28G 1-benzoyl-N-[2-[1-[(4-cyanophenyl)methyl]-1H-imidazol-5-yl]ethyl]-4-phenylmethyl-2(R)-piperazinedicarboxamide

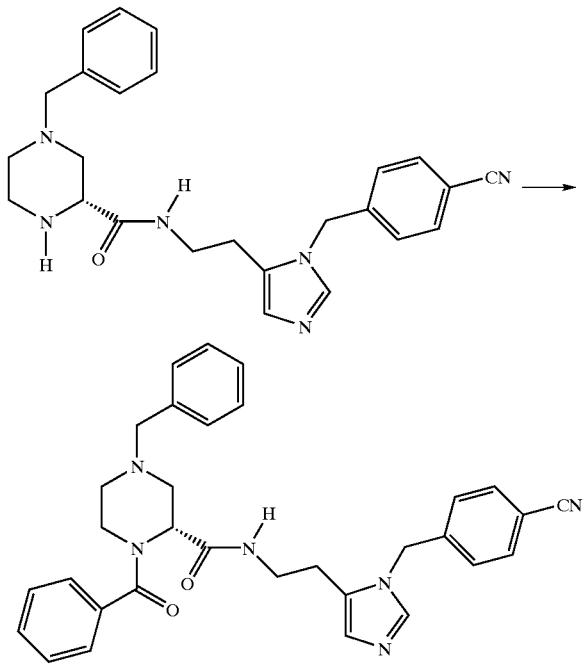

In a similar manner as is described in Example 28E, but using benzoyl chloride instead of propionyl chloride, the title compound is prepared as an off-white solid (33.2 mg, mp=115.3–170.3° C., MH+=533).

EXAMPLE 28H

1-Acetyl-N-[2-[1-[(4-cyanophenyl)methyl]-1H-imidazol-5-yl]ethyl]-4-(phenylmethyl)-2(R)-piperazinedicarboxamide

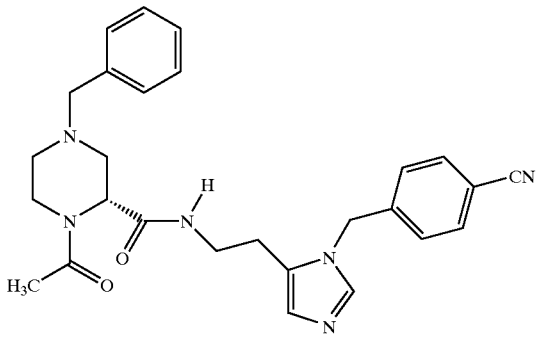

In a similar manner as is described in Example 28E, but using acetyl chloride instead of propionyl chloride, the title compound is prepared as an off-white solid (44.0 mg, mp=93.0–174.9° C., MH+=471).

EXAMPLE 28I

N-[2-[1-[(4-cyanophenyl)methyl]-1H-imidazol-5-yl]ethyl]-1-phenylacetyl-4-(phenylmethyl)-2(R)-piperazinedicarboxamide

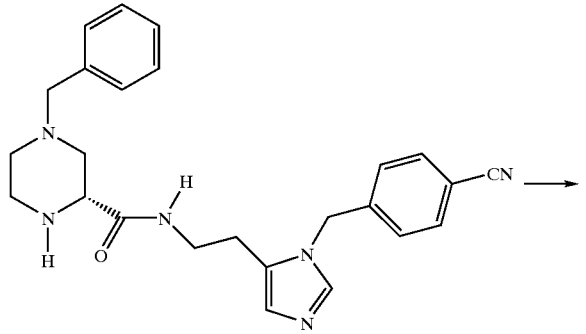

In a similar manner as is described in Example 28, but using phenylacetyl chloride instead of propionyl chloride, the title compound was prepared as an off-white solid (57.7 mg, 45%, mp=85.6–96.7° C., MH+=547).

EXAMPLE 28J

N-[2-[1-[(4-cyanophenyl)methyl]-1H-imidazol-5-yl]ethyl]-1-(methylsulfonyl)-4-(phenylmethyl)-2(R)-piperazinecarboxamide

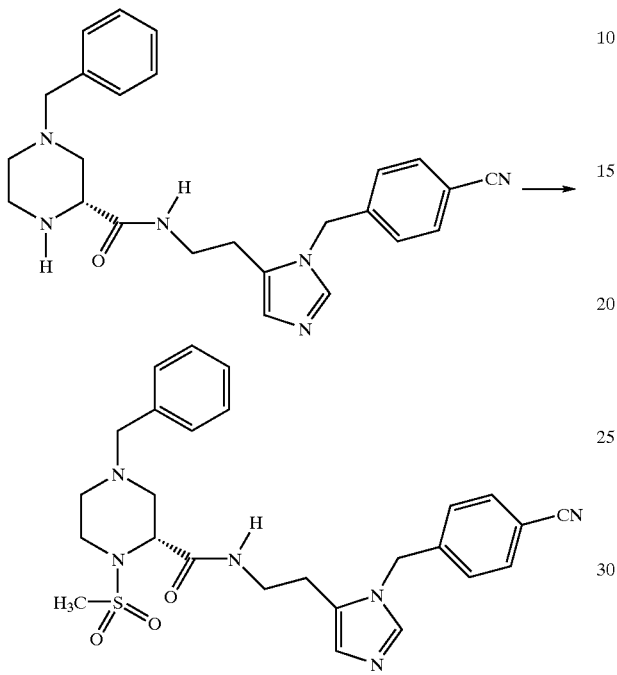

In a similar manner as described in Example 28E, but using methanesulfonyl chloride instead of propionyl chloride, the title compound is prepared as an off-white solid (52.4 mg, mp=96.5–161.7° C., MH+=507).

EXAMPLE 28K

N-[2-[1-[(4-cyanophenyl)methyl]-1H-imidazol-5-yl]ethyl]-1-(ethylsulfonyl)-4-(phenylmethyl)-2(R)-piperazinecarboxamide

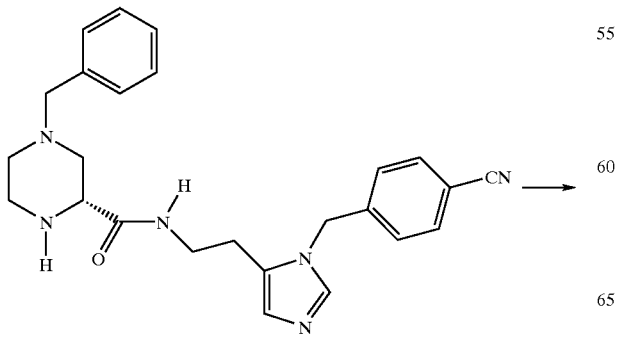

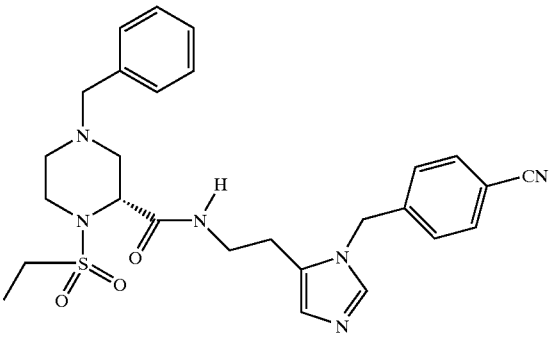

In a similar manner as is described in Example 28E, but using ethanesulfonyl chloride instead of propionyl chloride, the title compound is prepared as an off-white solid (40.4 mg, mp=97.3–150.2° C., MH+=521).

EXAMPLE 28L

N-[2-[1-[(4-cyanophenyl)methyl]-1H-imidazol-5-yl]ethyl]-1-(phenylsulfonyl)-4-(phenylmethyl)-2(R)-piperazinecarboxamide

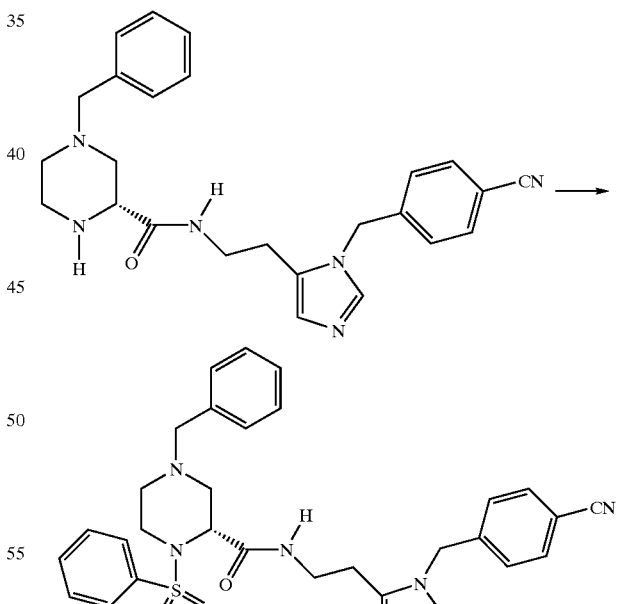

In a similar manner as is described in Example 28E, but using benzenesulfonyl chloride instead of propionyl chloride, the title compound is prepared as an off-white solid (50 mg, 75%, mp=105.7–166.5° C., MH+=569).

EXAMPLE 28M

N-[2-[1-[(4-cyanophenyl)methyl]-1H-imidazol-5-yl]ethyl]-1-[(phenylmethyl)sulfonyl]-4-(phenylmethyl)-2(R)-piperazinecarboxamide

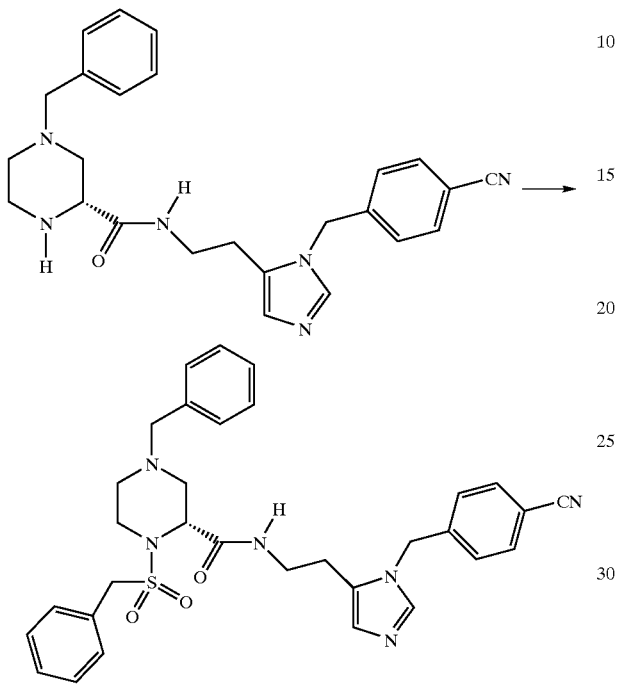

In a similar manner as is described in Example 28E, but using benzylsulfonyl chloride instead of propionyl chloride, the title compound is prepared as an off-white solid (26.8 mg, mp=118.1–180.5° C., MH+=583).

EXAMPLE 28N

N2-[2-[1-[(4-cyanophenyl)methyl]-1H-imidazol-5-yl]ethyl]-N1-phenyl-4-(phenylmethyl)-1,2(R)-piperazinecarboxamide

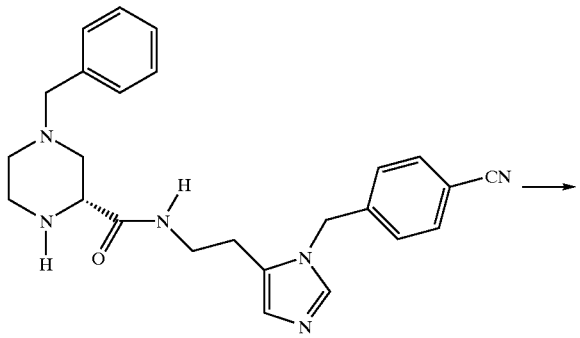

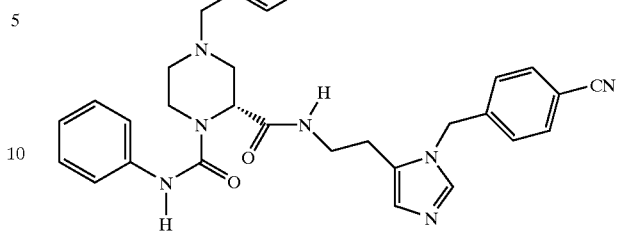

In a similar manner as is described in Preparative Example 12, but using the title compound from Preparative Example 11 and phenylisocyanate instead of cyclohexylisocyanate, the title compound is prepared as an off-white solid (28.8 mg, mp=128.0–139.2° C., MH+=548).

EXAMPLE 28O

N2-[2-[1-[(4-cyanophenyl)methyl]-1H-imidazol-5-yl]ethyl]-N1-(1,1-dimethylethyl)-4-(phenylmethyl)-1,2(R)-piperazinedicarboxamide

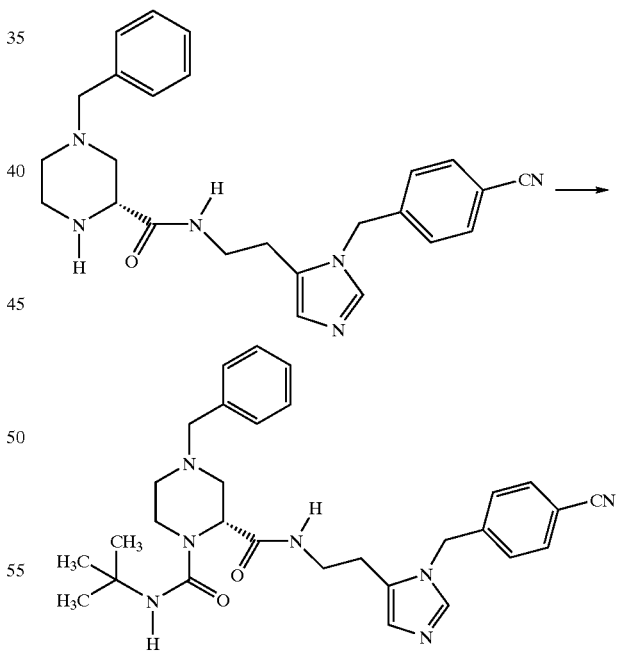

In a similar manner as is described in Preparative Example 12, but using the title compound from Preparative 11 and t-butylisocyanate instead of cyclohexylisocyanate, the title compound is prepared as an off-white solid (66.8 mg, mp=97.8° C., MH+=528).

EXAMPLE 28P

N-[2-[1-[(4-cyanophenyl)methyl]-1H-imidazol-5-yl]ethyl]-4-(phenylmethyl)-1-(4-pyridinylacetyl)-2(R)-piperazinecarboxamide N1-oxide

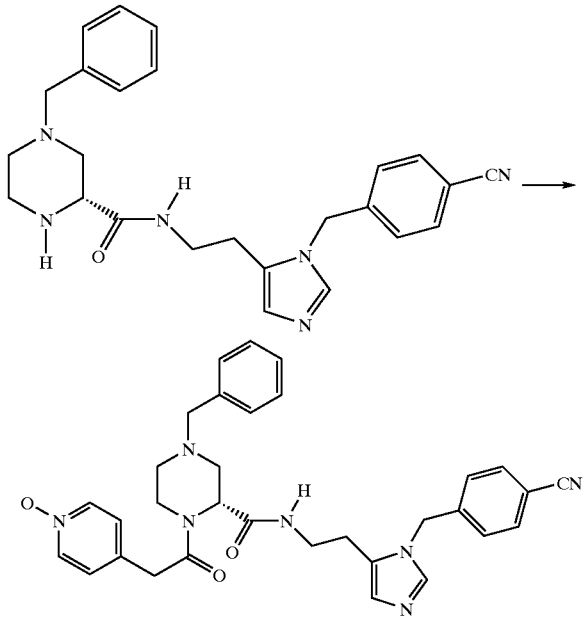

To the title compound from Preparative Example 11 (100 mg, 0.23 mmol) are added HOBt (47 mg, 0.35 mmol), DEC (67 mg, 0.35 mmol), pyridylacetic acid N-oxide (53 mg, 0.35 mmol), NMM (39 mL, 0.35 mmol) and anhydrous DMF (10 mL). The mixture is stirred at room temperature under $N_2$ overnight. The mixture is concentrated in vacuo, diluted with $CH_2Cl_2$ and washed with a saturated aqueous solution of $NaHCO_3$. The organic phase is dried over anhydrous $MgSO_4$, filtered and concentrated in vacuo. The residue is purified by preparative plate chromatography (silica gel) using 6% MeOH-98% $CH_2Cl_2$ saturated with aqueous ammonium hydroxide to give the title compound as an off-white solid (54 mg, MH+=564).

EXAMPLE 28Q

1-[[1-(aminocarbonyl)-4-piperidinyl]acetyl]-N-[2-[1-[(4-cyanophenyl)methyl]-1H-imidazol-5-yl]ethyl]-4-(phenylmethyl)-2(R)-piperazinecarboxamide

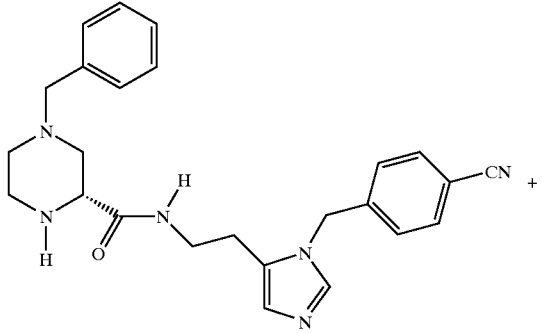

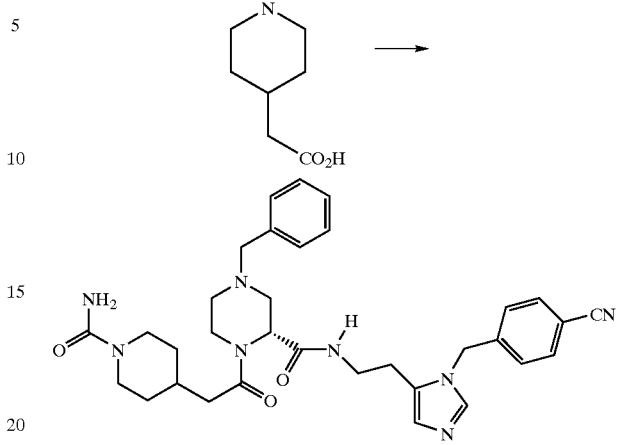

In a similar manner as is described in Example 28P, but using the title compound from Preparative Example 11 and the piperidylacetic acid from Preparative Example instead of pyridylacetic acid N-oxide, the title compound is prepared as an off-white solid (76 mg, 55%, mp=118.5° C., MH+=597).

EXAMPLE 28R

N2-[2-[1-[(4-Cyanophenyl)methyl]-1H-imidazol-5-yl]ethyl]-N1-cyclohexyl-4-(phenylsulfonyl)-1,2(R)-piperazinedicarboxamide

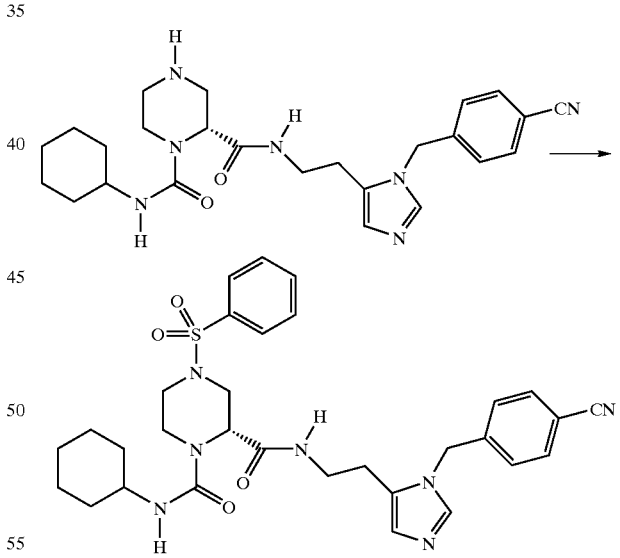

To a solution of the title compound from Prepartive Example 8 and 9 (50 mg, 0.12 mmol, 1.0 eq) and triethylamine (0.05 mL, 0.36 mmol) in anhydrous dichloromethane (3 ml) is added benzenesulfonyl chloride (0.02 mL, 0.12 mmol). The resulting mixture is stirred at room temperature under $N_2$ for 72 hrs, then diluted with additional dichloromethane, washed with aqueous sodium hydroxide (1 M) and dried over anhydrous MgSO4. The organic phase is filtered, concentrated in vacuo, and the residue purified by preparative plate chromatography (silica gel) using 10% methanol (saturated with ammonia)-90% acetonitrile, and repurified using 5% methanol-dichloromethane saturated with aqueous ammonium hydroxide to afford the title compound as an orange solid (5 mg, mp=143.6° C., MH+=604).

EXAMPLE 28S

N1-cyclohexyl-N2-[3-(1H-imidazol-1-yl)propyl]-N2,4-bis(phenylmethyl)-1,2(R)-piperazinedicarboxamide

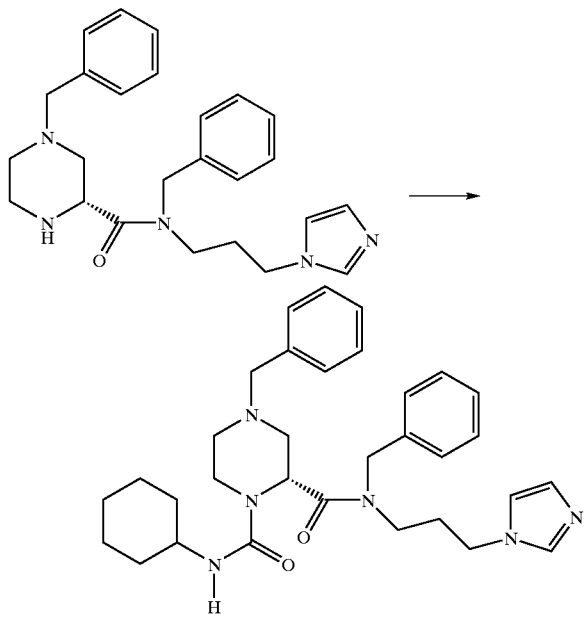

To a solution of the title compound from Example 28Y (0.13 g, 0.3 mmol) dissolved in anhydrous dichloromethane (3 ml) is added cyclohexylisocyanate (0.054 mL, 0.43 mmol) and the resulting solution is stirred at room temperature overnight, then concentrated in vacuo. The residue is purified by preparative plate chromatography (silica gel) using 5% MeOH—CH$_2$Cl$_2$ saturated with aqueous ammonium hydroxide to give the title compound as a white solid (164 mg, mp=89.1° C., MH+=543).

EXAMPLE 28T

N1-(1,1-dimethylethyl)-N2-[3-(1H-imidazol-1-yl)propyl]-N2,4-bis(phenylmethyl)-1,2(R)-piperazinedicarboxamide

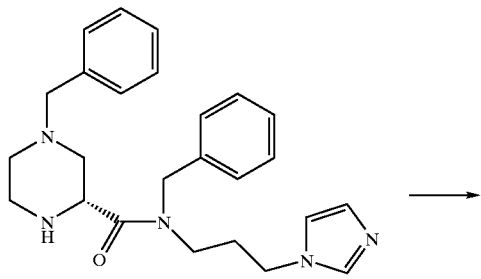

-continued

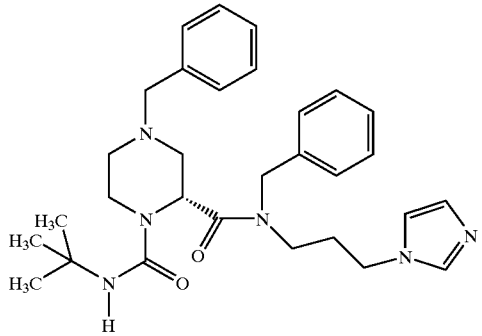

To a solution of the title compound from Example 28Y (0.13 g, 0.3 mmol) dissolved in anhydrous dichloromethane (3 ml) is added t-butylisocyanate (0.05 mL, 0.43 mmol) and the resulting solution is stirred at room temperature overnight, then concentrated in vacuo. The residue is purified by preparative plate chromatography (silica gel) using 5% MeOH—CH$_2$Cl$_2$ saturated with aqueous ammonium hydroxide to give the title compound as a white solid (131 mg, mp=57.8° C., MH+=517).

EXAMPLE 28U 1,1-dimethyl 1-[(cyclohexylamino)carbonyl]-2(R)-[[[2-(2-methyl-1H-benzimidazol-1-yl)ethyl]amino]carbonyl]-4-piperazinecarboxylate

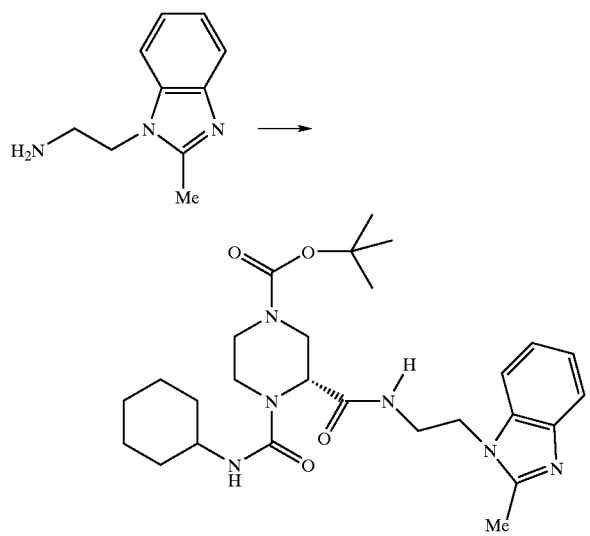

A solution of the title compound from Preparative Example 14 (0.9 g, 5.14 mmol) and the anhydride from Preparative Example (1.38 g, 1.05 eq) dissolved in anhydrous dichloromethane (10 ml) are stirred at room temperature overnight. Additional anhydride (0.105 g) is added and after 1 hr cyclohexylisocyanate (0.98 mL, 7.71 mmol) is added to the reaction mixture which is stirred for an additional 1.5 hrs. Concentration in vacuo and purification by flash column chromatography (silica gel) using 1–3% MeOH—CH$_2$Cl$_2$ saturated with ammonium hydroxide as eluent affords the title compound as a white solid (1.82 g, mp=126.9–128.9° C., MH+=513).

EXAMPLE 28V 4-(1,1-dimethylethyl), 1-(phenylmethyl)-2(R)-[[[2-(2,4-dimethyl-1H-imidazol-1-yl)ethyl]amino]carbonyl]-1,4-piperazinedicarboxylate and 4-(1,1-dimethylethyl), 1-(phenylmethyl)-2(R)-[[[2-(2,5-dimethyl-1H-imidazol-1-yl)ethyl]amino]carbonyl]-1,4-piperazinedicarboxylate

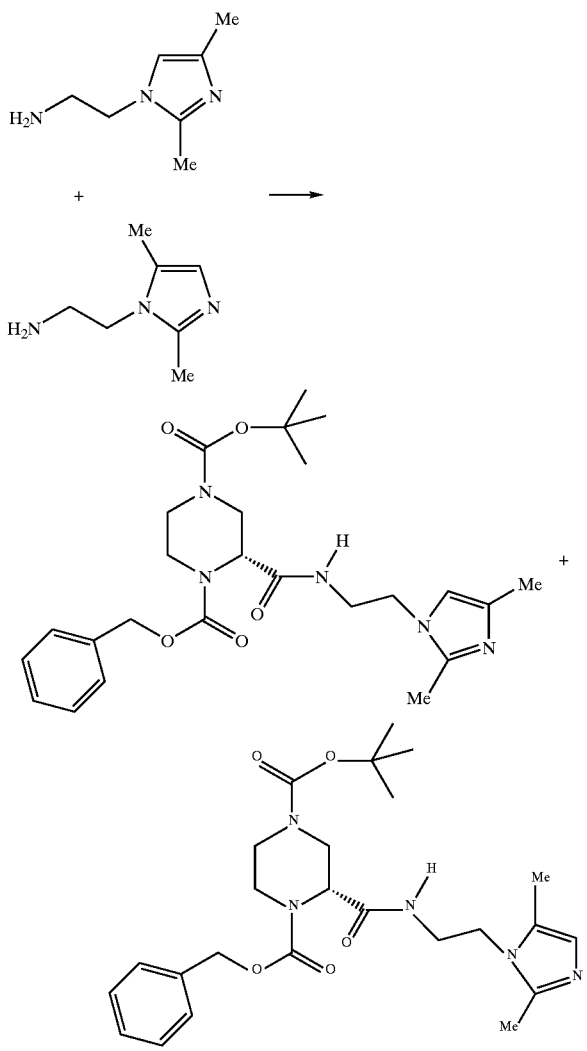

A solution of the title compound from Preparative Example 15 (2.12 g, 15.2 mmol), triethylamine (30.4 mmol) and the anhydride from Preparative Example (3.89 g, 15.2 mmol) dissolved in anhydrous dichloromethane (30 ml) is stirred at room for 30 min. Benzyloxycarbonylsuccinamide (4.17 g, 16.7 mmol) is added and the resulting mixture is stirred at room temperature overnight. Concentration in vacuo and purification by flash column chromatography (silica gel) using 2% MeOH—CH$_2$Cl$_2$ saturated with ammonium hydroxide as eluent affords the title compound as a (2.57 g). The regioisomers are separated by HPLC (Chiracel AD column) using 5% isopropanol-95% hexane-0.2% diethylamine to give the 2,4-dimethyl isomer (mp=64.2° C., MH+=486) and the 2,5-dimethyl isomer (mp=71.5° C., MH+=486).

EXAMPLE 28W

N1-cyclohexyl-N2-[2-(2-methyl-1H-benzimidazol-1-yl)ethyl]-4-(phenylmethyl)-1,2(R)-piperazinedicarboxylate

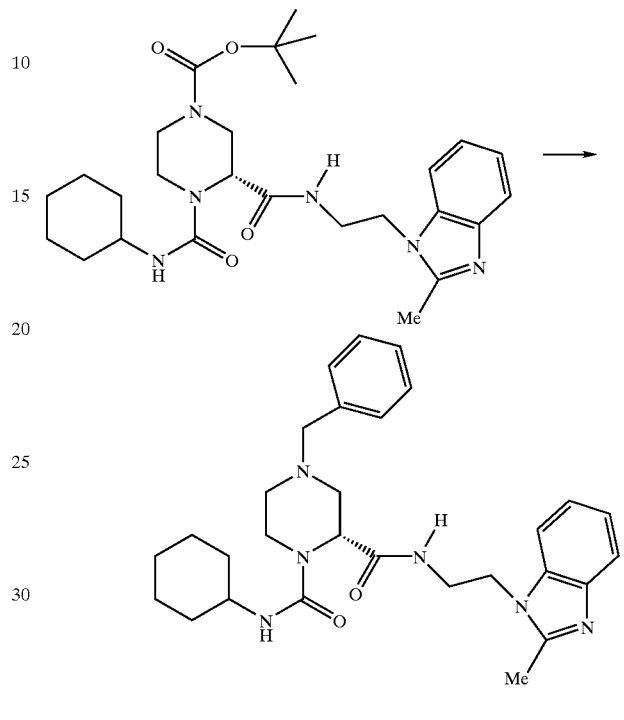

A solution of the title compound from Example 28U (101) (0.49 g, 0.89 mmol) dissolved in anhydrous dichloromethane (10 ml) and trifluoroacetic acid (2 ml) are stirred at room temperature for 3 hrs. The resulting solution is concentrated in vacuo, then the residue is combined with anhydrous dichloromethane (10 ml), benzaldehyde (0.28 mL, 2.68 mmol), glacial acetic acid (1 mL) and sodium triacetoxyborohydride (0.76 g, 3.6 mmol) and stirred at room temperature for 48 h. The reaction mixture is concentrated in vacuo, diluted with dichloromethane and washed with 1 N NaOH (aq). The organic phase is dried over anhydrous MgSO$_4$, filtered, concentrated in vacuo, and purified by flash column chromatography (silica gel) using 1–3% MeOH—CH$_2$Cl$_2$ saturated with ammonium hydroxide as eluent to afford the title compound as a white solid (0.40 g, mp=192.9–194.9° C., MH+=503).

EXAMPLE 28X

Bis(1,1-dimethylethyl) 2(R)-[[[2-(phenylmethoxy)ethyl]amino]carbonyl]-1,4-piperazinedicarboxylate

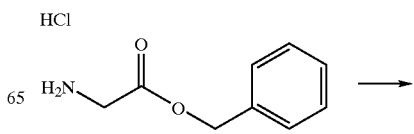

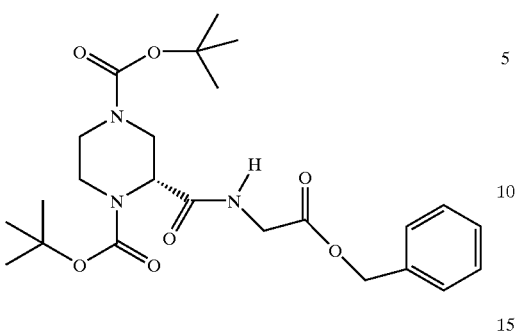

A solution of benzyl 2-aminoacetate hydrochloride (1.3 g, 7.8 mmol), triethylamine (3.26 mL, 23.4 mmol) and the anhydride from Preparative Example (2 g, 7.8 mmol) dissolved in anhydrous dichloromethane (40 ml) are stirred at room temperature overnight. The reaction mixture is diluted with dichloromethane and washed with 1 N NaOH (aq) and brine. The organic phase is dried over anhydrous MgSO$_4$, filtered and concentrated in vacuo to afford the title compound as a white solid (1.03 g, MH+=478 (35%), 322 (100%)).

EXAMPLE 28Y

N2-[3-(1H-imidazol-1-yl)propyl]N2,4-bis(phenylmethyl)-1,2(R)-piperazinecarboxamide and N2-[3-(1H-imidazol-1-yl)propyl]N1,2,4-tris(phenylmethyl)-1,2(R)-piperazinecarboxamide

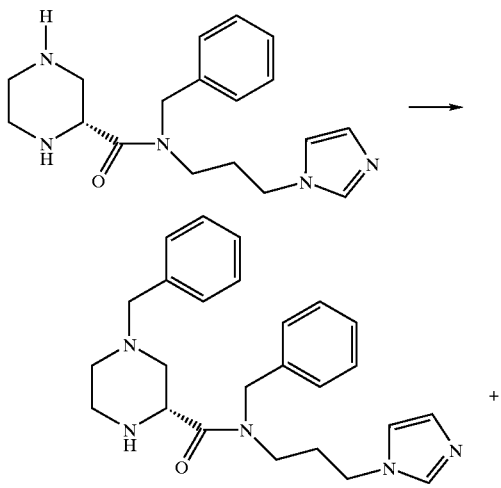

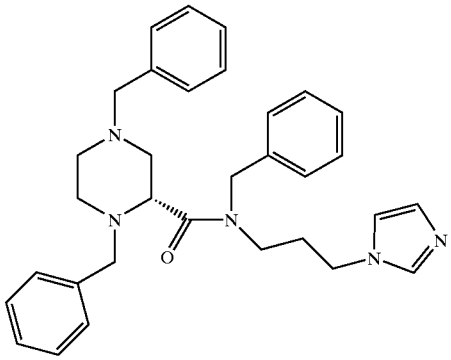

To the title compound from Preparative Example 17 (381 mg, 1.16 mmol) and benzaldehyde (0.12 mL, 1.16 mmol) dissolved in glacial acetic acid (1 mL) and anhydrous dichloromethane (15 ml) at 0° C. are added sodium triacetoxyborohydride (740 mg, 3.5 mmol) and the resulting mixture is warmed to room temperature and stirred for an additional 12 h. The reaction mixture is washed with 1 N NaOH (aq) and the organic phase is dried over anhydrous MgSO$_4$, filtered and concentrated in vacuo. The residue is purified by preparative plate chromatography (silica gel) using 2–5% MeOH—CH$_2$Cl$_2$ saturated with aqueous ammonium hydroxide to give the title dibenzyl compound (256 mg, MH+=418) and the title tribenzyl compound (78.4 mg, MH+=508).

EXAMPLE 28Y1

N1-cyclohexyl-N2-[3-(1H-imidazol-1-yl)propyl]-N2,4-bis(phenylmethyl)-1,2(R)-Piperazinedicarboxamide To a solution of the title compound from Example 28Y (0.13 g, 0.3 mmol) dissolved in anhydrous dichloromethane (3 ml) was added cyclohexylisocyanate (0.054 mL, 0.43 mmol) and the resulting solution was stirred at room temperature overnight, then concentrated in vacuo. The residue was purified by preparative plate chromatography (silica gel) using 5% MeOH—CH$_2$Cl$_2$ saturated with aqueous ammonium hydroxide to give the title compound as a white solid (164 mg, 99%, mp=89.1° C., MH+=543).

EXAMPLE 28Y2

N1-(1,1-dimethylethyl)-N2-[3-(1H-imidazol-1-yl)propyl]-N2,4-bis(phenylmethyl)-1,2(R)-piperazine-dicarboxamide

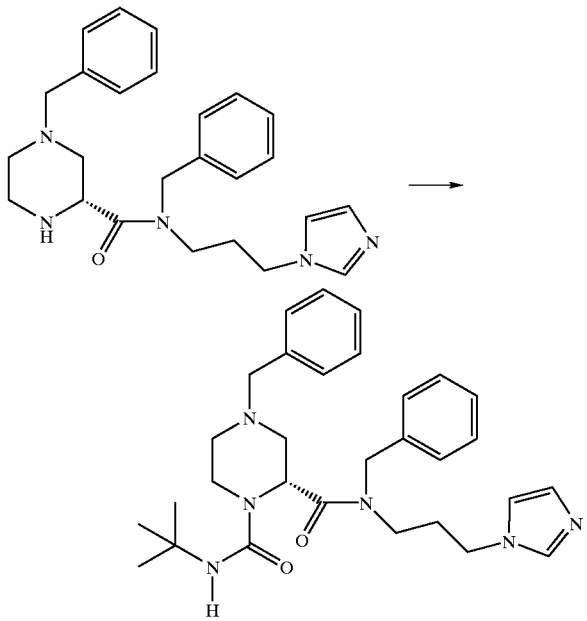

To a solution of the title compound from Example 28Y (0.13 g, 0.3 mmol) dissolved in anhydrous dichloromethane (3 ml) was added t-butylisocyanate (0.05 mL, 0.43 mmol) and the resulting solution was stirred at room temperature overnight, then concentrated in vacuo. The residue was purified by preparative plate chromatography (silica gel) using 5% MeOH—$CH_2Cl_2$ saturated with aqueous ammonium hydroxide to give the title compound as a white solid (131 mg, 83%, mp=57.8° C., MH+=517).

EXAMPLE 28Z

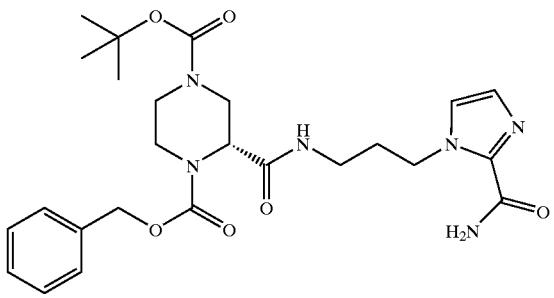

A solution of the title compound from Step B of Preparative Example 23 (0.23 g, 0.86 mmol) is stirred in 4M HCl in dioxane (4 mL) at room temperature overnight. The solution is concentrated and stirred with $CH_2Cl_2$ (10 mL), DMF (10 mL) and TEA (0.47 mL, 5 eq.) before adding piperazine anhydride (0.26 g, 1.2 eq.) portionwise. The resulting solution is stirred at room temperature 1.5 hours and additional anhydride added (0.043 g, 0.2 eq.). The reaction mixture is stirred 0.5 hours before adding CBZ-OSuc (0.28 g, 1.2 eq.). The resulting solution is stirred 3 hours and quenched by the addition of $NaHCO_3$ (10 mL), diluted with $H_2O$ (20 mL) and extracted with $CH_2Cl_2$ (3×50 mL). The combined organics are dried over $Na_2SO_4$, filtered, and concentrated in vacuo. The crude product is purified by flash chromatography using a 5% MeOH in $CH_2Cl_2$ solution as eluent to give a white solid (0.32 g): mp=71–75° C.; LCMS: $MH^+$=515.

EXAMPLE 28 Z1

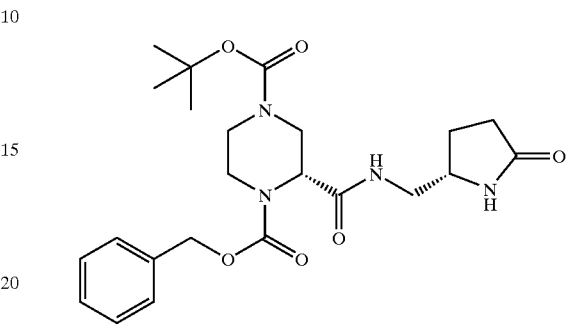

By essentially the same procedure as set forth in Example 28 Z, except using the title compound from Step B of Preparative Example 24, the title compound is prepared (1.66 g): mp=77–79° C.; LCMS: $MH^+$=461.

EXAMPLE 28 Z2.

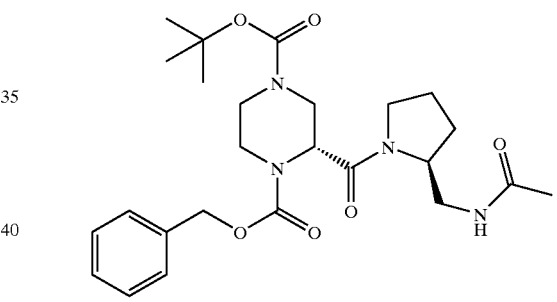

By essentially the same procedure set forth in Example 28 Z except using the title compound from Step C of Preparative Example 25 (0.17 g, 0.950 mmol), the title compound is prepared (0.37 g): mp=58–60° C.; LCMS: $MH^+$=489.

EXAMPLE 29. PS 287238-1-0

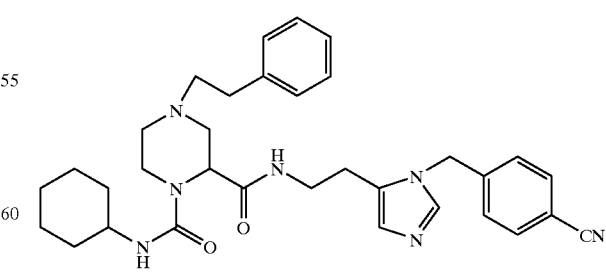

Accurate Mass ($[M + H]^+$)
Calculated: 568
Found: 568

EXAMPLE 30. PS 812520-1-0
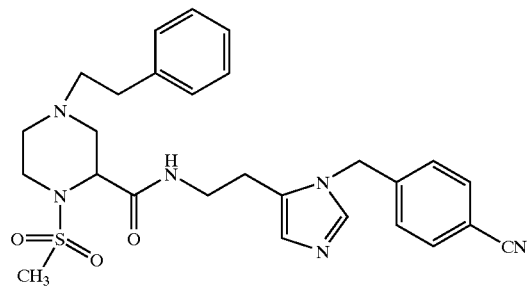
Accurate Mass ([M + H]+)
Calculated: 521
Found: 521
EXAMPLE 31. PS 465781-1-0
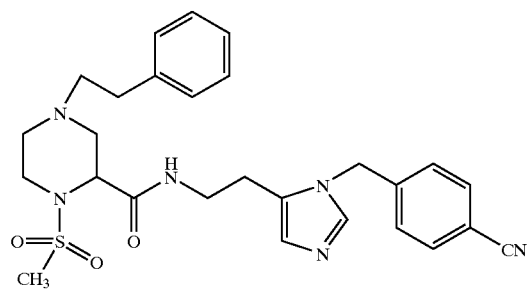
Accurate Mass ([M + H]+)
Calculated: 527
Found: 527
EXAMPLE 32. PS 461400-1-0
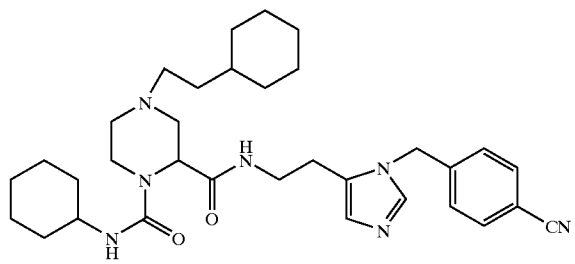
Accurate Mass ([M + H]+)
Calculated: 574
Found: 574
EXAMPLE 33. PS 815156-1-0
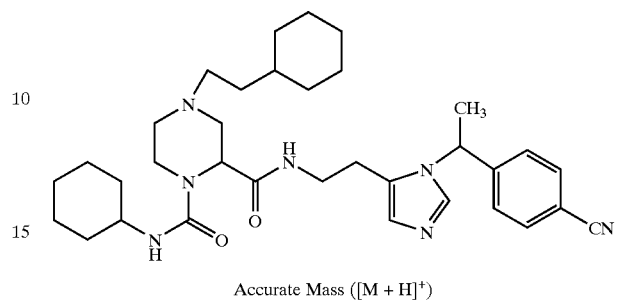
Accurate Mass ([M + H]+)
Calculated: 588
Found: 588
EXAMPLE 34. PS 159773-1-0
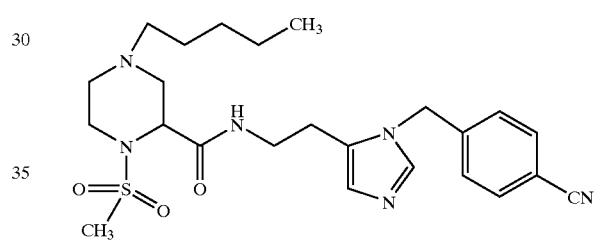
Accurate Mass ([M + H]+)
Calculated: 487
Found: 487
EXAMPLE 35. PS 372802-1-0
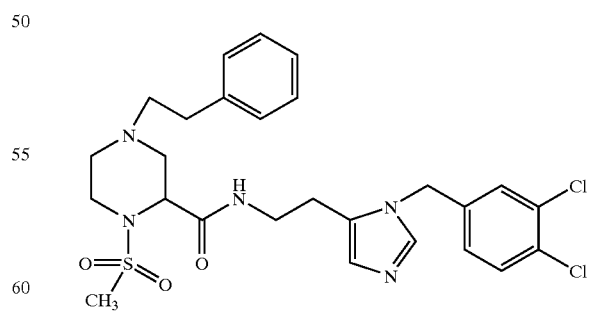
Accurate Mass ([M + H]+)
Calculated: 564
Found: 564

EXAMPLE 36. PS 793961-1-0
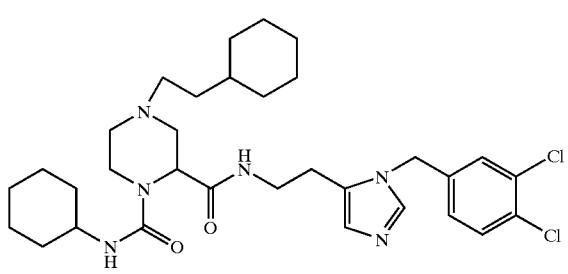
Accurate Mass ([M + H]⁺)
Calculated: 617
Found: 617
EXAMPLE 37. PS 321542-1-0
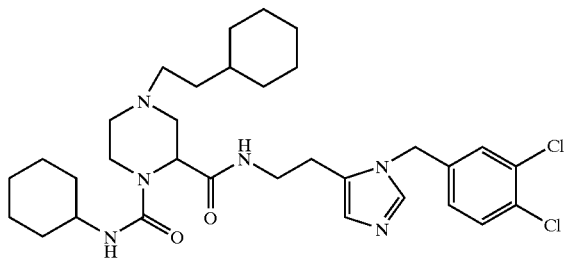
Accurate Mass ([M + H]⁺)
Calculated: 617
Found: 617
EXAMPLE 38. PS 288326-1-0
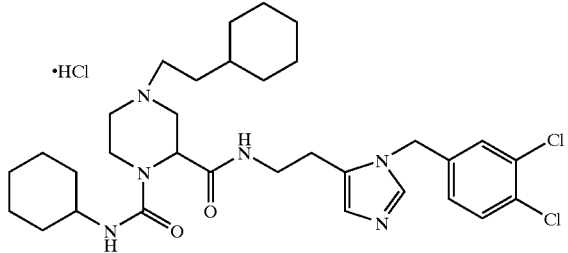
Accurate Mass ([M + H]⁺)
Calculated: 617
Found: 617
EXAMPLE 39. PS 478500-1-0
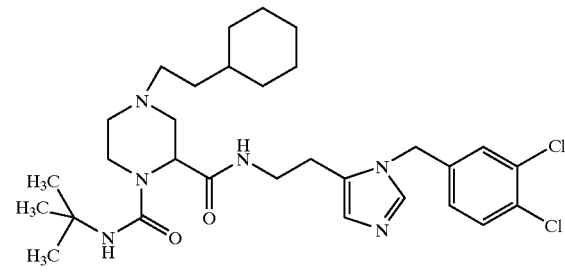
Accurate Mass ([M + H]⁺)
Calculated: 592
Found: 592
EXAMPLE 40. PS 783003-1-0
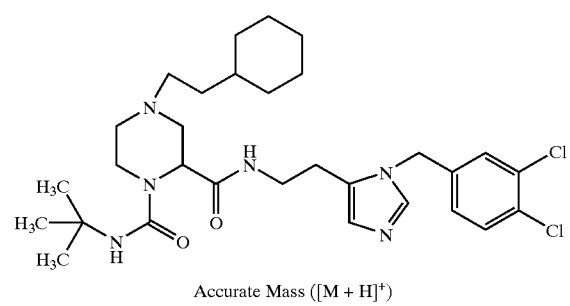
Accurate Mass ([M + H]⁺)
Calculated: 591
Found: 591
EXAMPLE 41. PS 241936-1-0
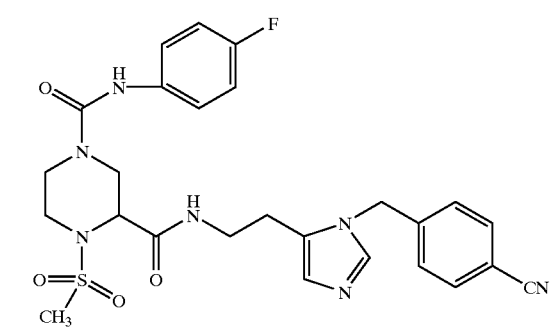
Accurate Mass ([M + H]⁺)
Calculated: 554
Found: 554

EXAMPLE 42. PS 409643-1-0
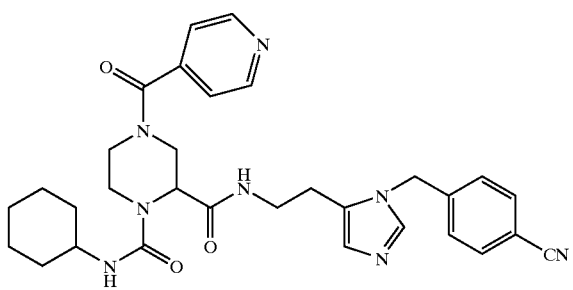
Accurate Mass ([M + H]$^+$)
Calculated: 569
Found: 569
EXAMPLE 43. PS 725556-1-0
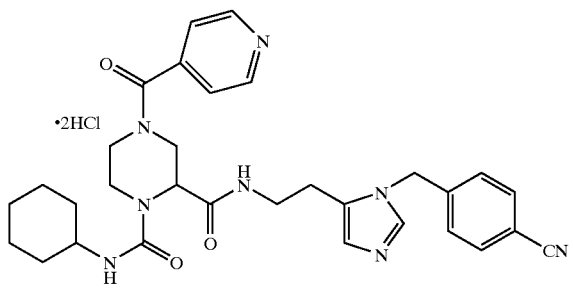
•2HCl
Accurate Mass ([M + H]$^+$)
Calculated: 569
Found: 569
EXAMPLE 44. PS 769295-1-0
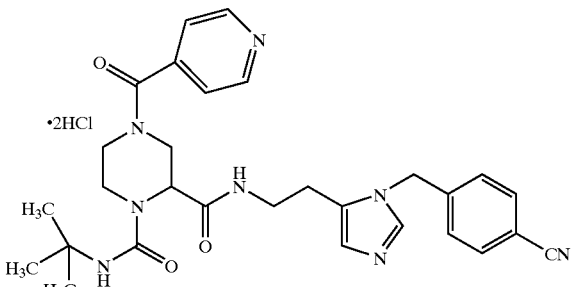
•2HCl
Accurate Mass ([M + H]$^+$)
Calculated: 544
Found: 544
EXAMPLE 45. PS 075114-1-0
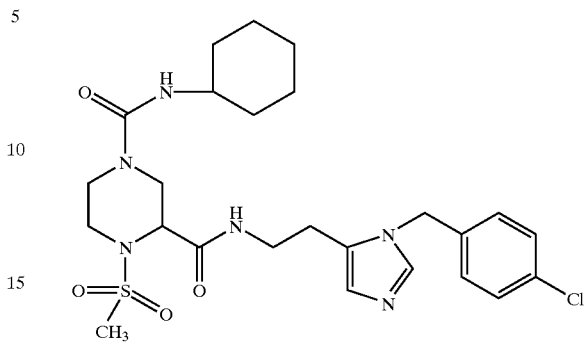
Accurate Mass ([M + H]$^+$)
Calculated: 551
Found: 551
EXAMPLE 46. PS 990951-1-0
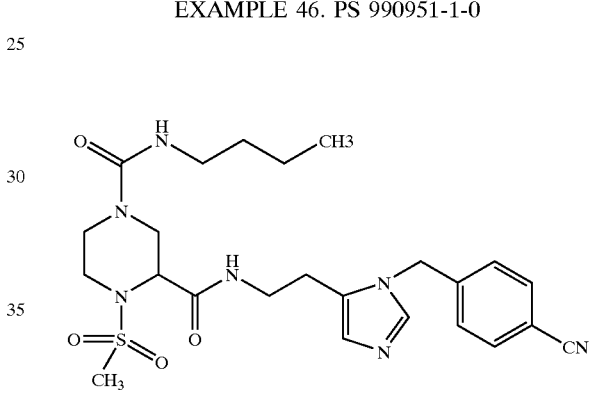
Accurate Mass ([M + H]$^+$)
Calculated: 516
Found: 516
EXAMPLE 47. PS 192638-1-0
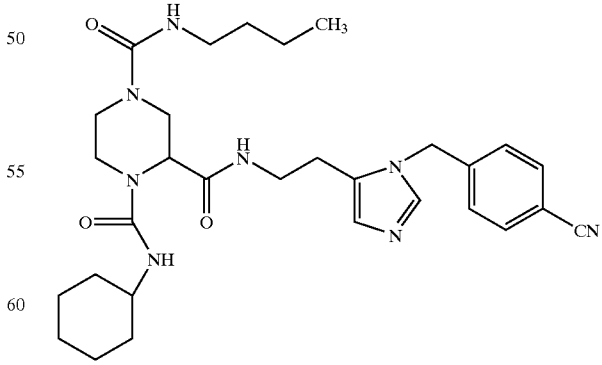
Accurate Mass ([M + H]$^+$)
Calculated: 563
Found: 563

EXAMPLE 48. PS 354164-1-0
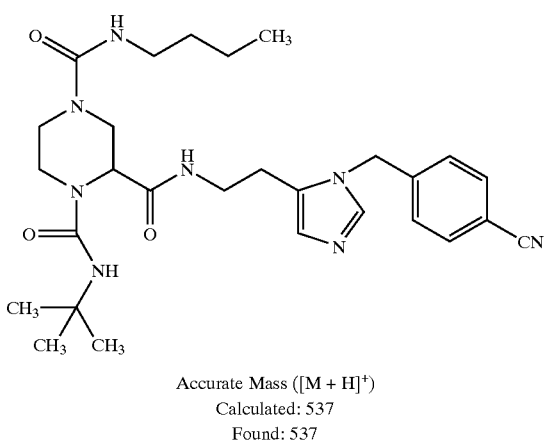
Accurate Mass ([M + H]⁺)
Calculated: 537
Found: 537
EXAMPLE 49. PS 395570-1-0
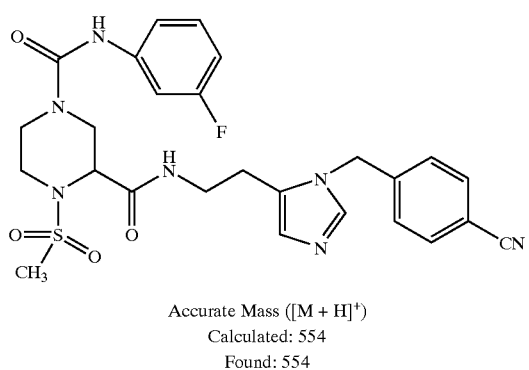
Accurate Mass ([M + H]⁺)
Calculated: 554
Found: 554
EXAMPLE 50. PS 956973-1-0
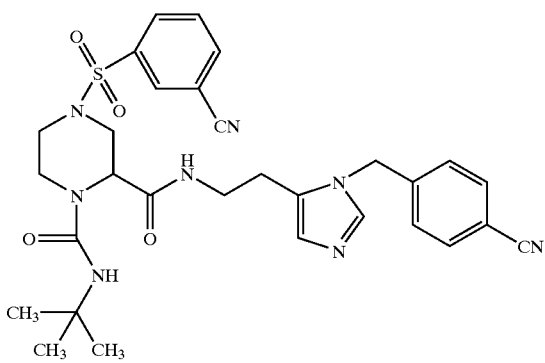
Accurate Mass ([M + H]⁺)
Calculated: 603
Found: 603
EXAMPLE 51. PS 859989-1-0
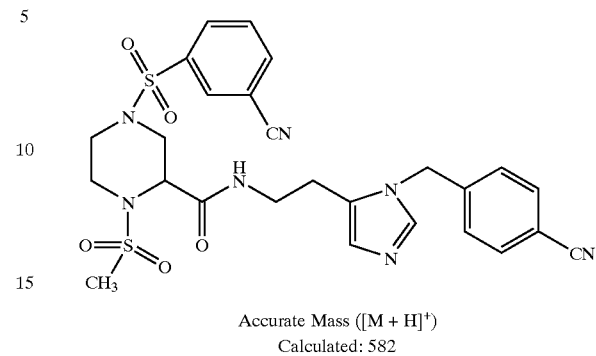
Accurate Mass ([M + H]⁺)
Calculated: 582
Found: 582
EXAMPLE 52. PS 467023-1-0
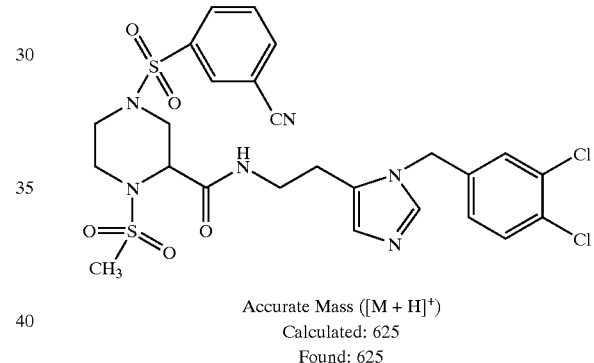
Accurate Mass ([M + H]⁺)
Calculated: 625
Found: 625
EXAMPLE 53. PS 437810-1-0
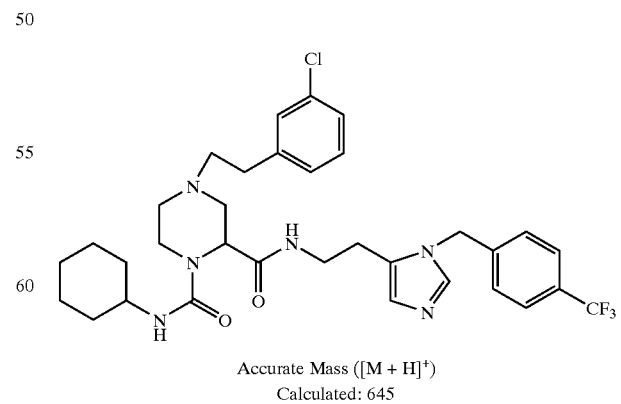
Accurate Mass ([M + H]⁺)
Calculated: 645
Found: 645

EXAMPLE 54. PS 381385-1-0
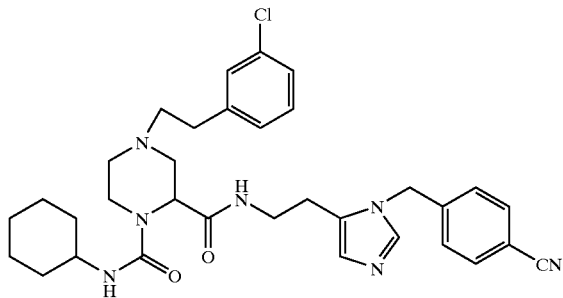
Accurate Mass ([M + H]⁺)
Calculated: 602
Found: 602
EXAMPLE 55. PS 201633-1-0
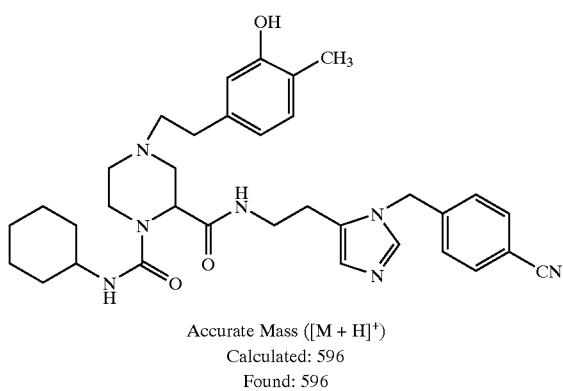
Accurate Mass ([M + H]⁺)
Calculated: 596
Found: 596
EXAMPLE 56. PS 593455-1-0
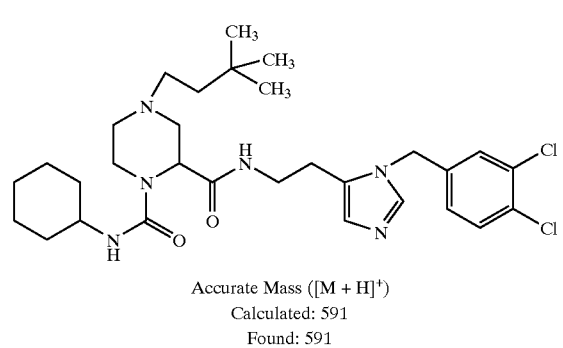
Accurate Mass ([M + H]⁺)
Calculated: 591
Found: 591
EXAMPLE 57. PS 409643-1-0
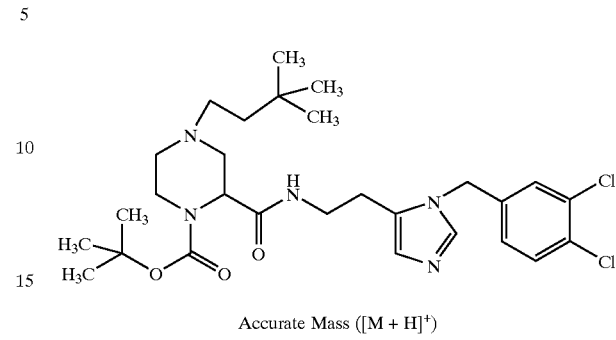
Accurate Mass ([M + H]⁺)
Calculated: 566.
Found: 566.
EXAMPLE 57A. PS 477090-1-0
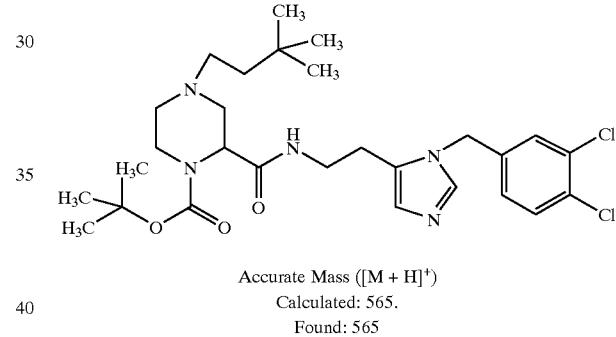
Accurate Mass ([M + H]⁺)
Calculated: 565.
Found: 565
EXAMPLE 58. PS 130057-1-0
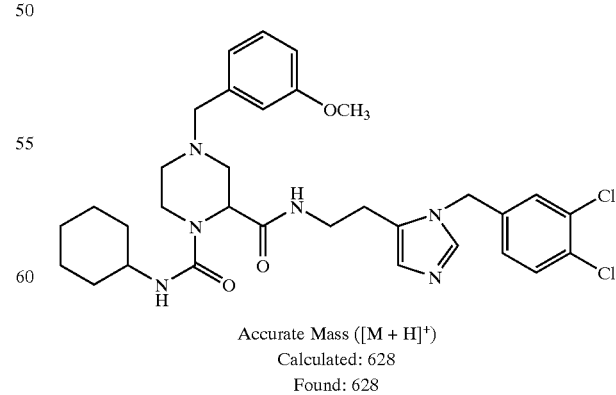
Accurate Mass ([M + H]⁺)
Calculated: 628
Found: 628

EXAMPLE 59. PS 516972-1-0
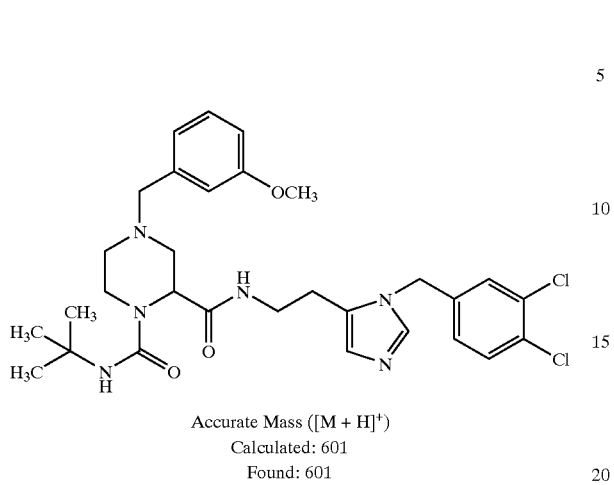
Accurate Mass ([M + H]⁺)
Calculated: 601
Found: 601
EXAMPLE 60. PS 064691-1-0
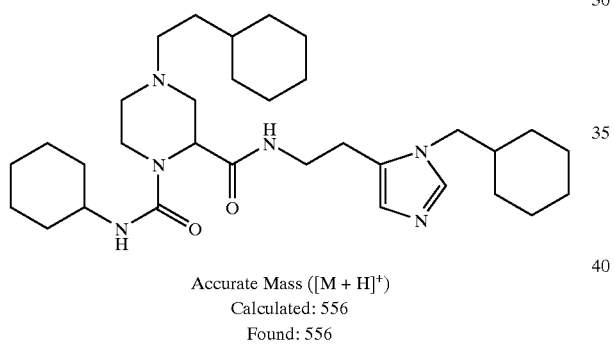
Accurate Mass ([M + H]⁺)
Calculated: 556
Found: 556
EXAMPLE 61. PS 028348-1-0
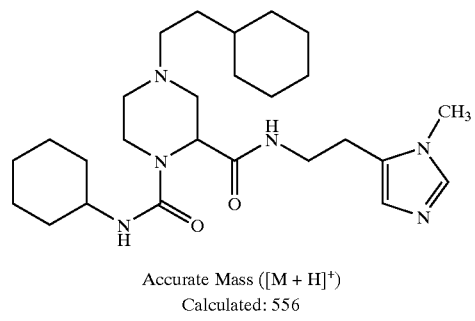
Accurate Mass ([M + H]⁺)
Calculated: 556
Found: 556
EXAMPLE 62. PS 410892-1-0
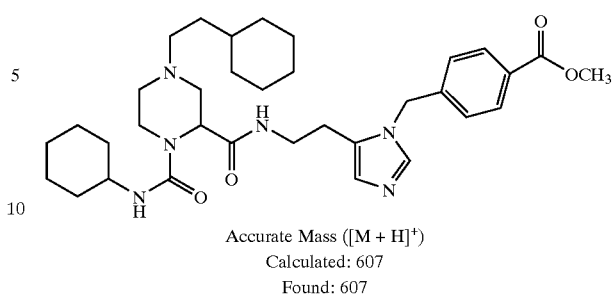
Accurate Mass ([M + H]⁺)
Calculated: 607
Found: 607
EXAMPLE 64. PS 813558-1-0
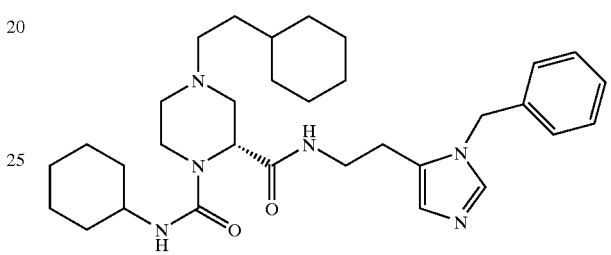
Accurate Mass ([M + H]⁺)
Calculated: 549
Found: 549
EXAMPLE 65. PS 319448-1-0
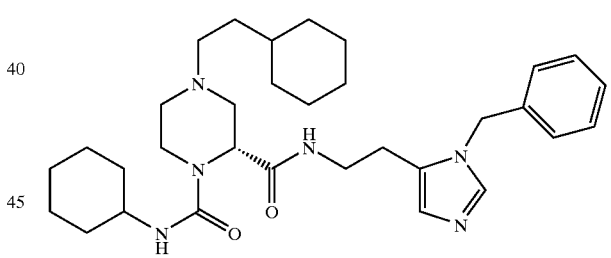
Accurate Mass ([M + H]⁺)
Calculated: 549
Found: 549
EXAMPLE 66. PS 4200838-1-0
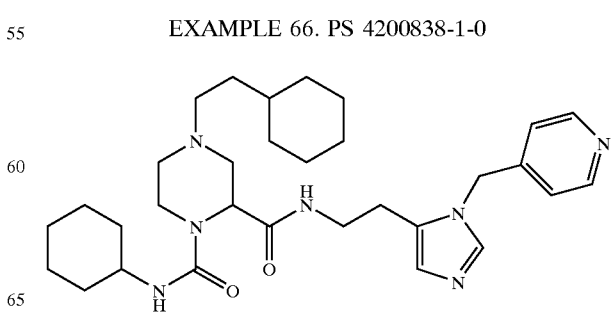

EXAMPLE 67. PS 259236-1-0
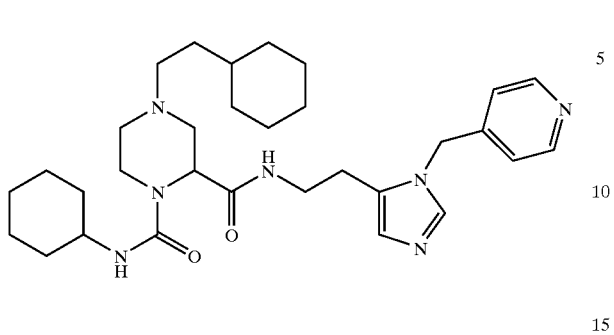
EXAMPLE 68
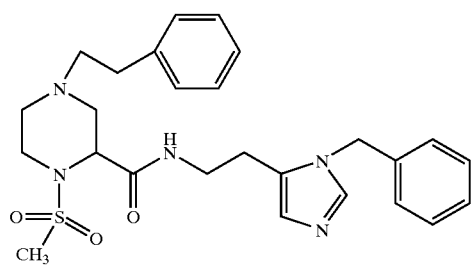
EXAMPLE 69
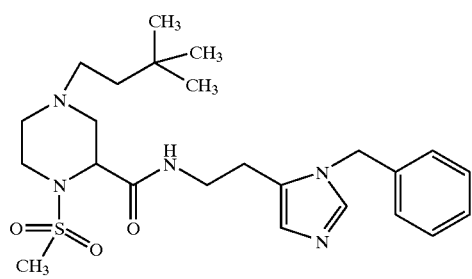
EXAMPLE 70
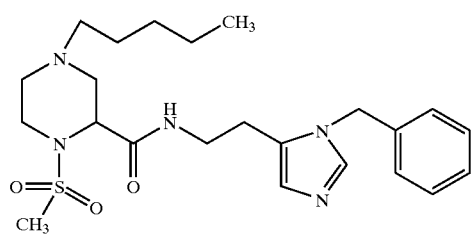
EXAMPLE 71
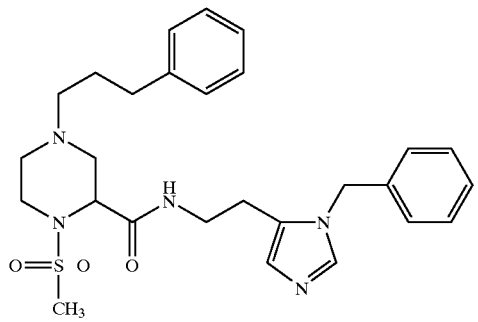
EXAMPLE 72
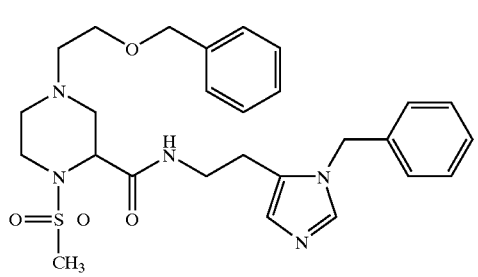
EXAMPLE 73
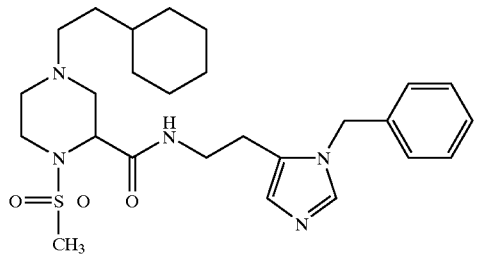
EXAMPLE 74
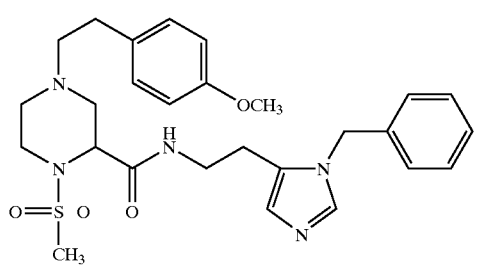

EXAMPLE 75
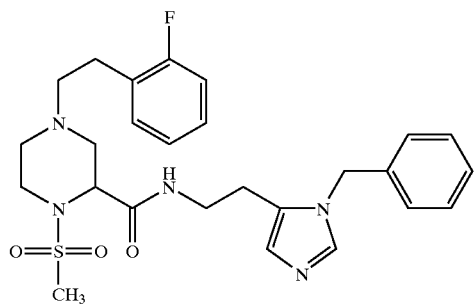
EXAMPLE 79
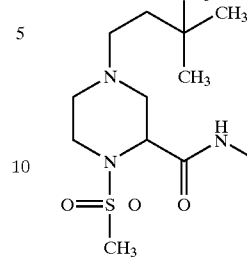
EXAMPLE 76
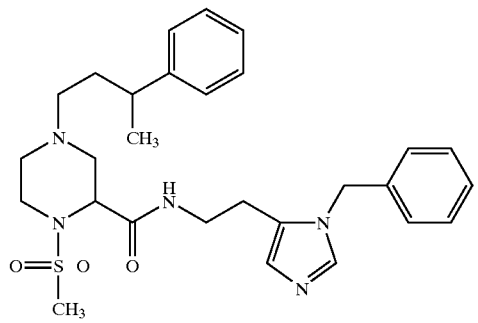
EXAMPLE 80
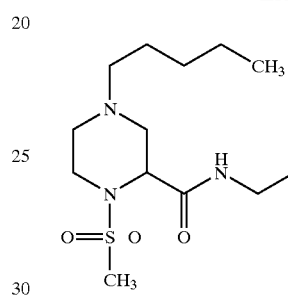
EXAMPLE 77
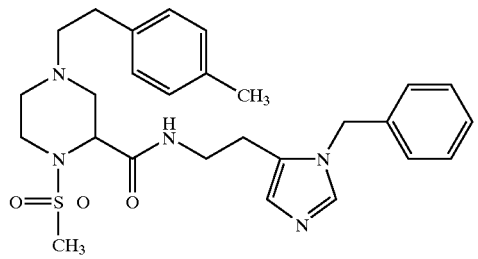
EXAMPLE 81
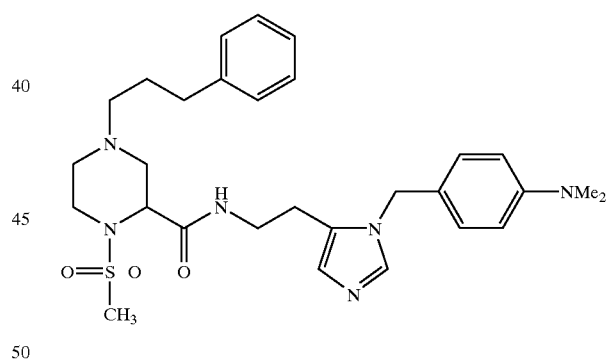
EXAMPLE 78
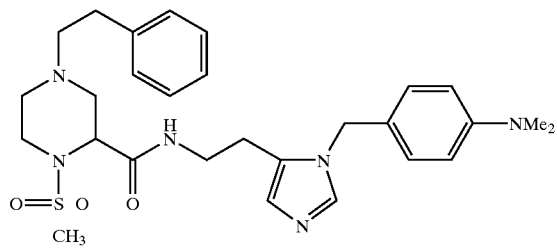
EXAMPLE 82
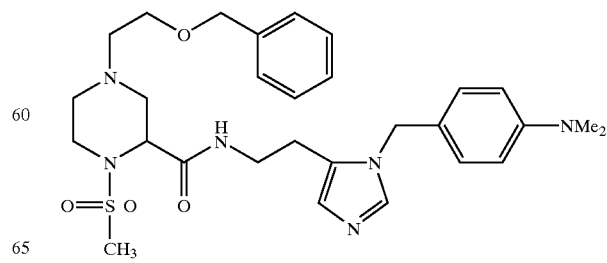

EXAMPLE 83
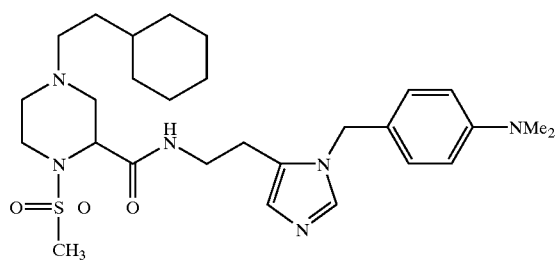
EXAMPLE 87
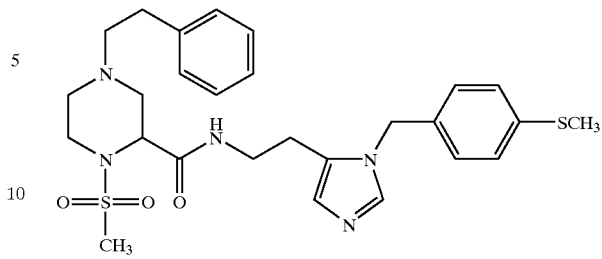
EXAMPLE 84
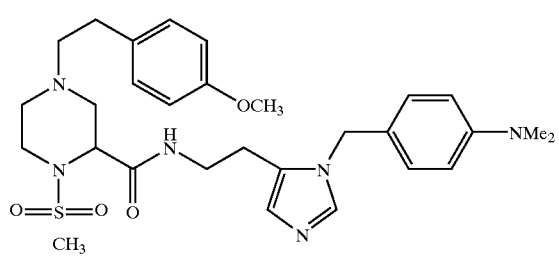
EXAMPLE 88
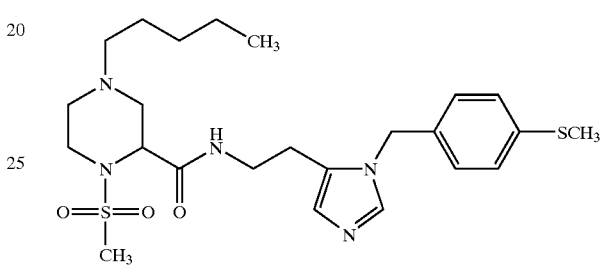
EXAMPLE 85
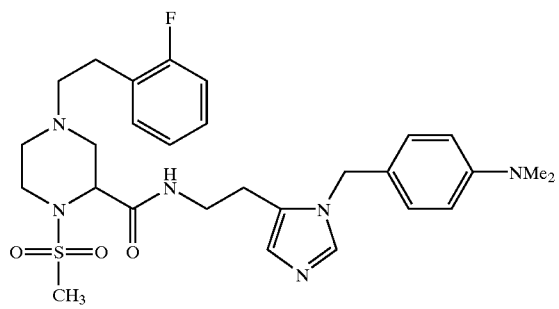
EXAMPLE 89
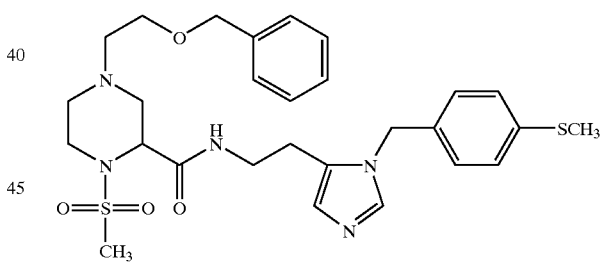
EXAMPLE 86
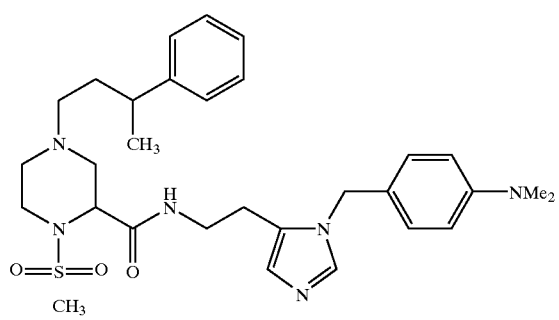
EXAMPLE 90
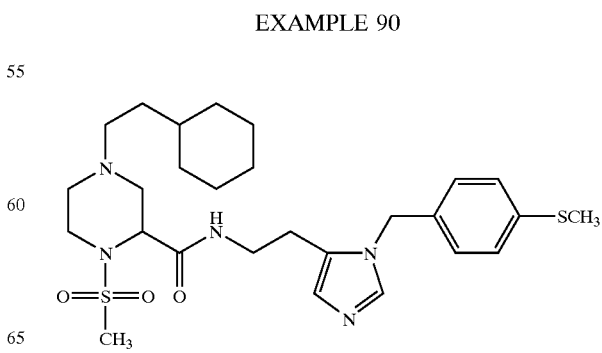

EXAMPLE 91
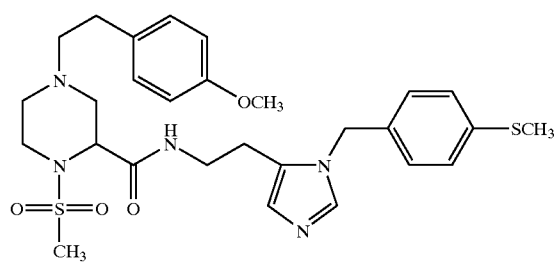
EXAMPLE 95
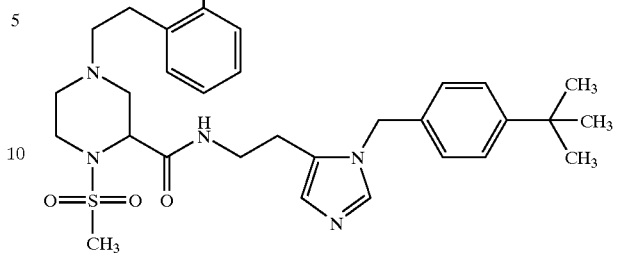
EXAMPLE 92
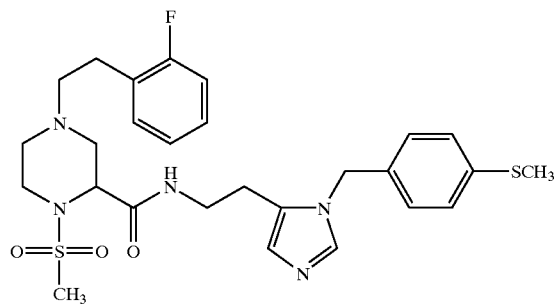
EXAMPLE 96
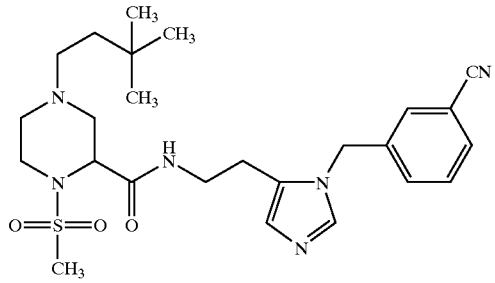
EXAMPLE 93
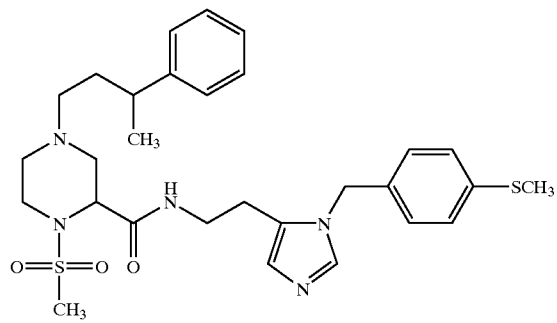
EXAMPLE 97
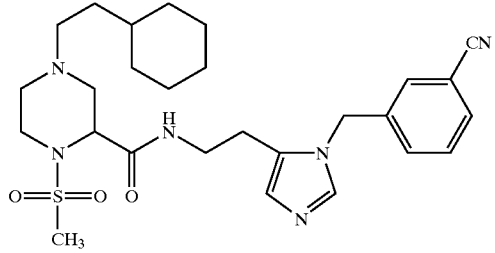
EXAMPLE 94
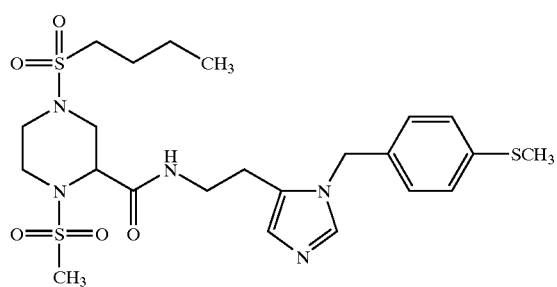
EXAMPLE 98
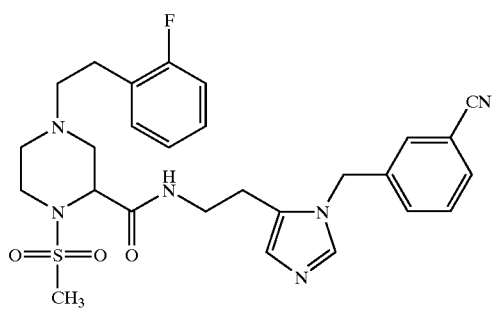

73
EXAMPLE 99
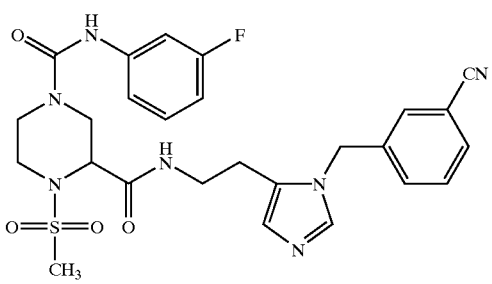
EXAMPLE 100
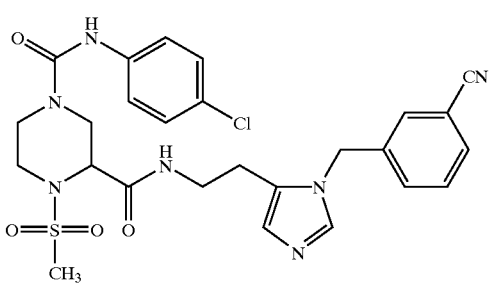
EXAMPLE 101
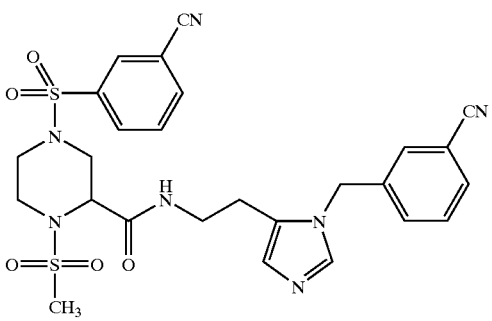
EXAMPLE 102
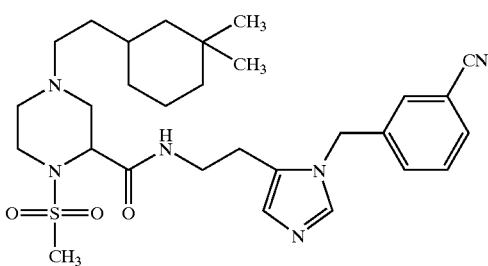
74
EXAMPLE 103
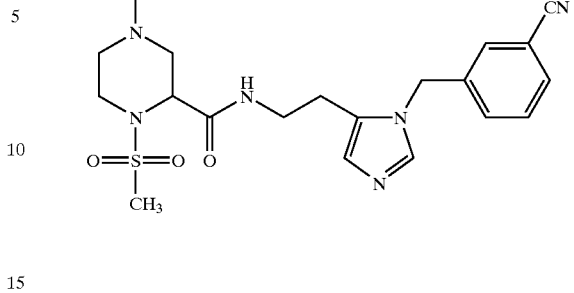
EXAMPLE 104
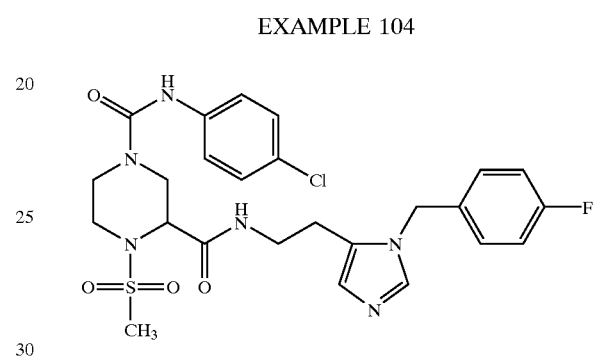
EXAMPLE 105
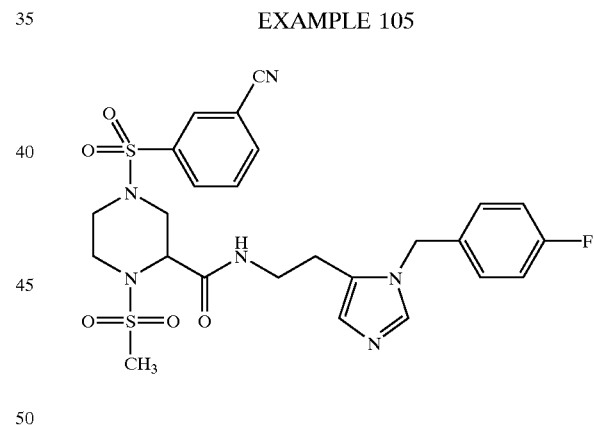
EXAMPLE 106
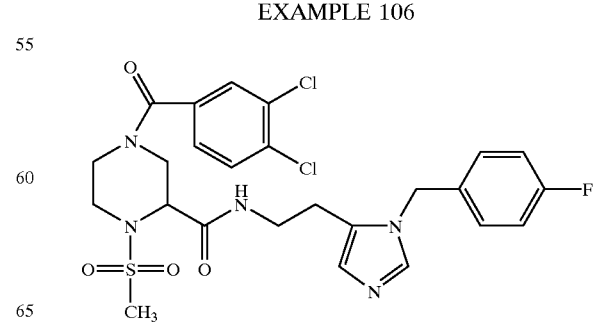

EXAMPLE 107
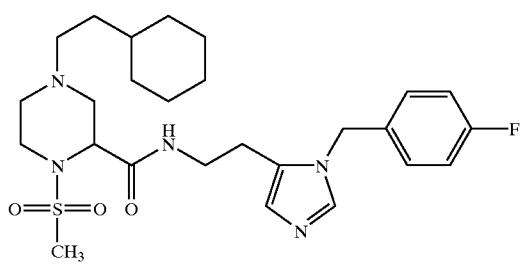
EXAMPLE 111
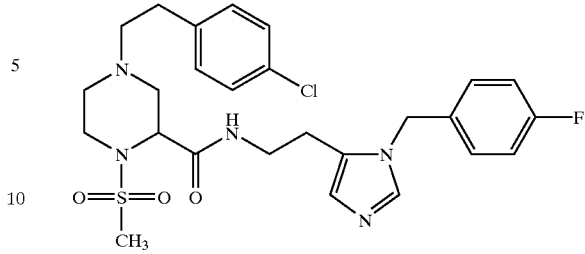
EXAMPLE 108
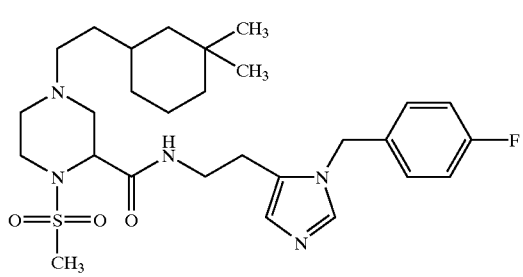
EXAMPLE 112
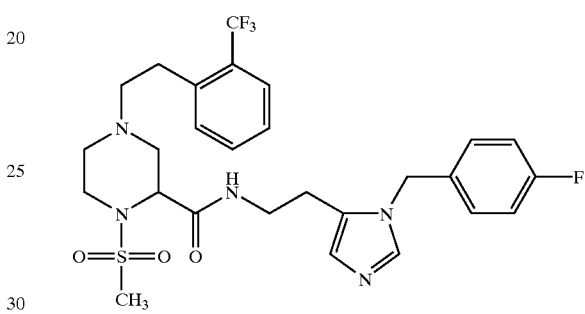
EXAMPLE 109
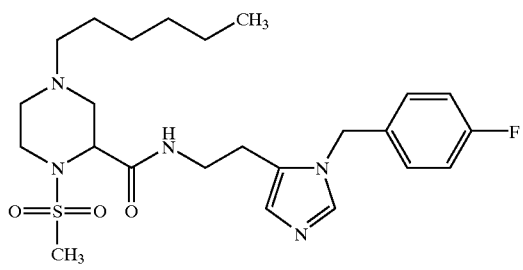
EXAMPLE 113
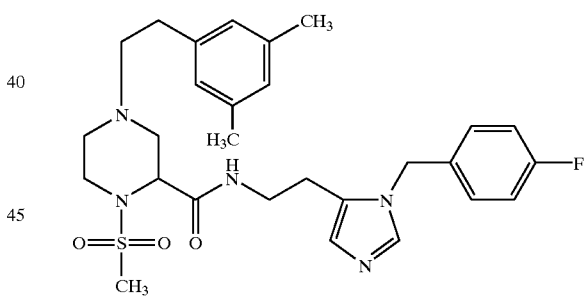
EXAMPLE 110
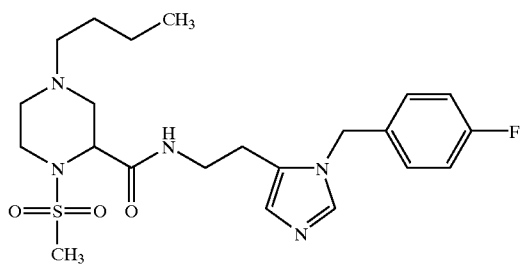
EXAMPLE 114
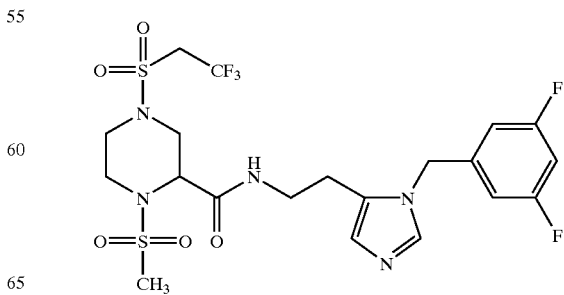

EXAMPLE 115
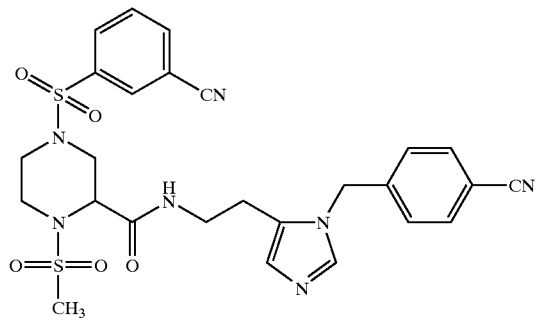
EXAMPLE 116
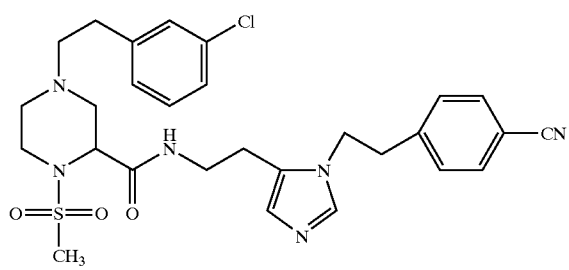
EXAMPLE 117
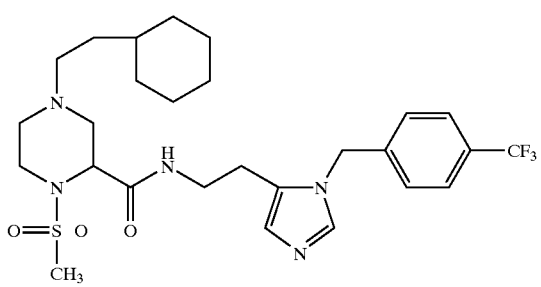
EXAMPLE 118
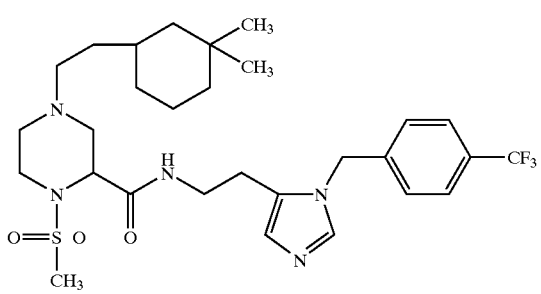
EXAMPLE 119
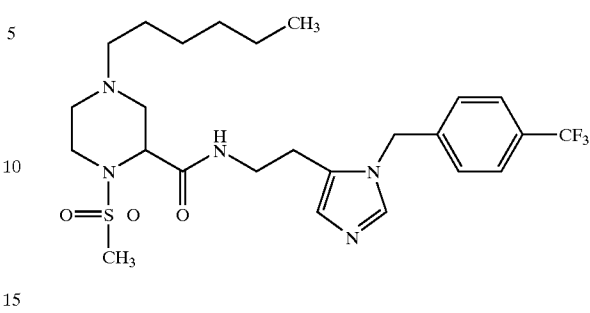
EXAMPLE 120
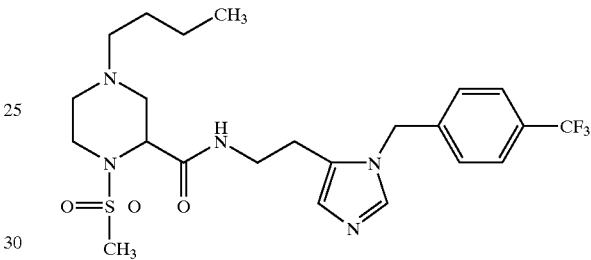
EXAMPLE 121
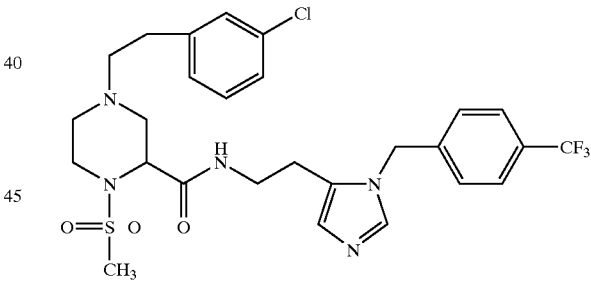
EXAMPLE 122
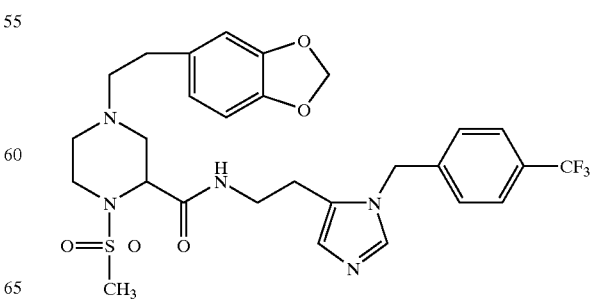

EXAMPLE 123
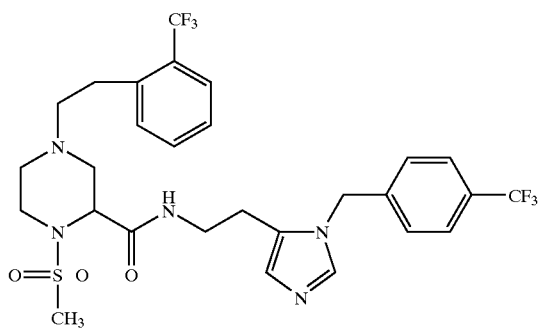
EXAMPLE 127
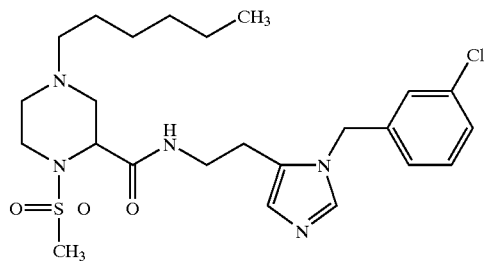
EXAMPLE 124
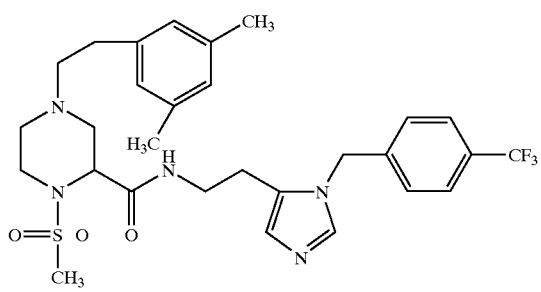
EXAMPLE 128
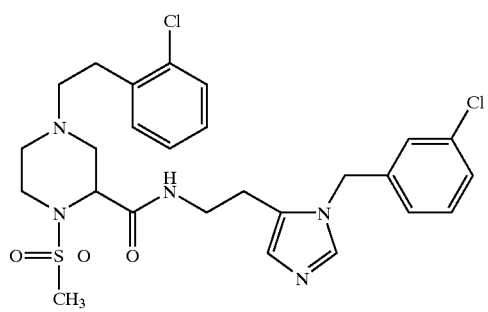
EXAMPLE 125
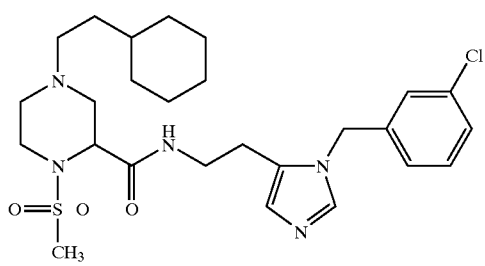
EXAMPLE 129
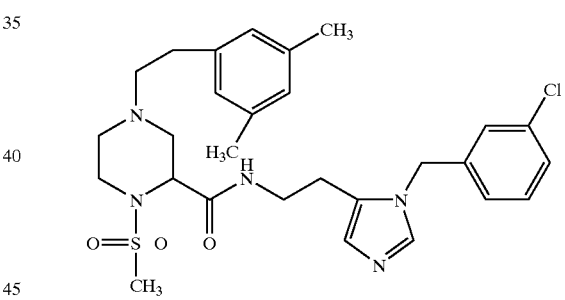
EXAMPLE 126
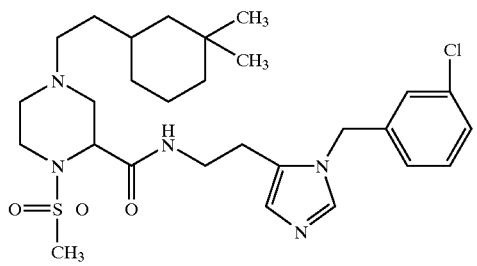
EXAMPLES 130–165
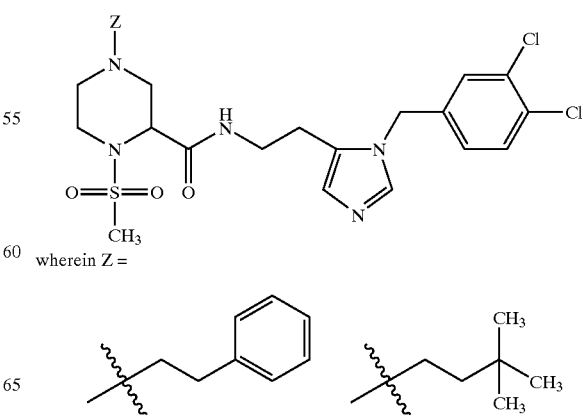
wherein Z =

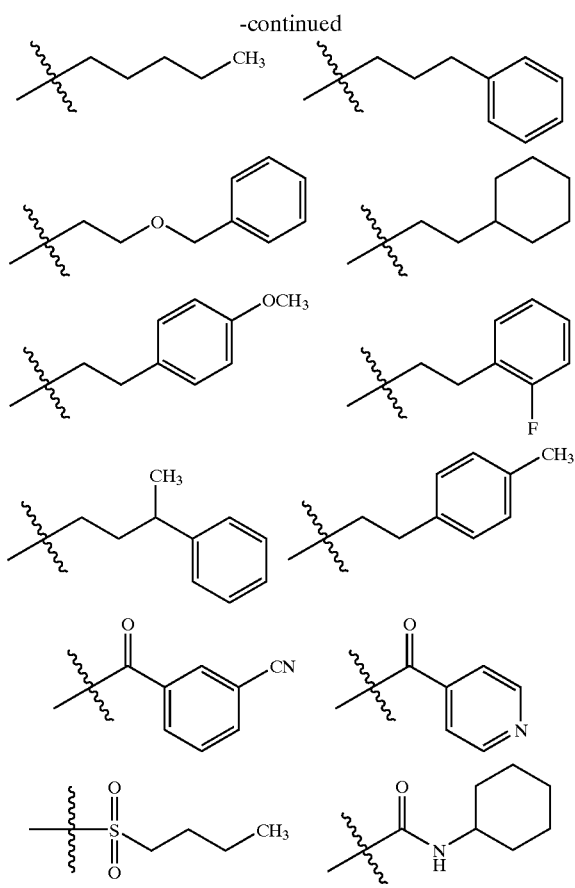
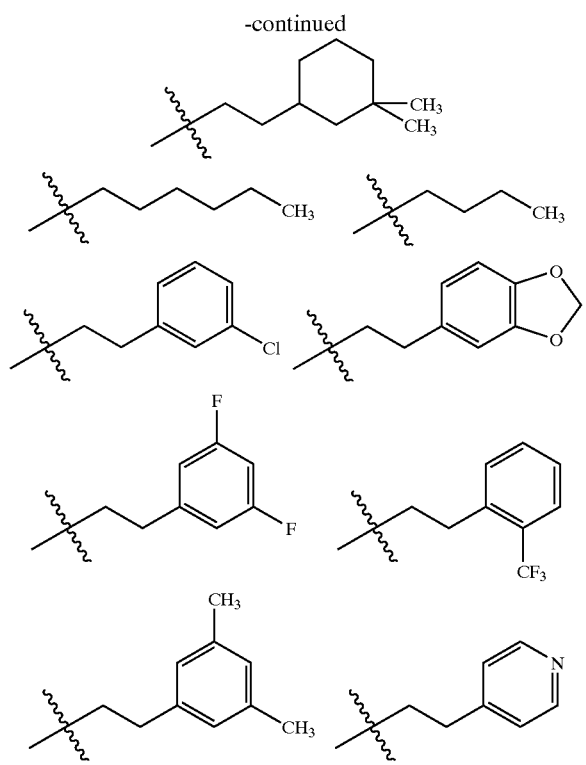
EXAMPLES 165–193
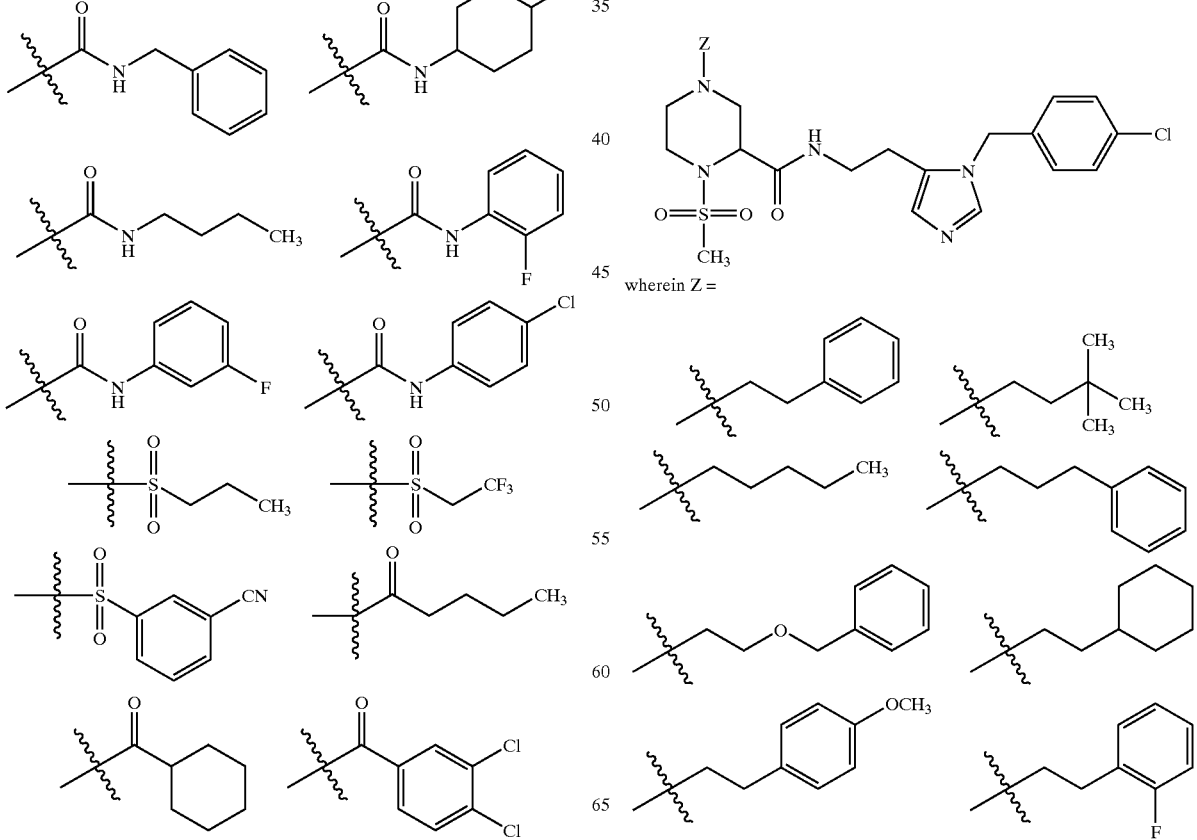
wherein Z =

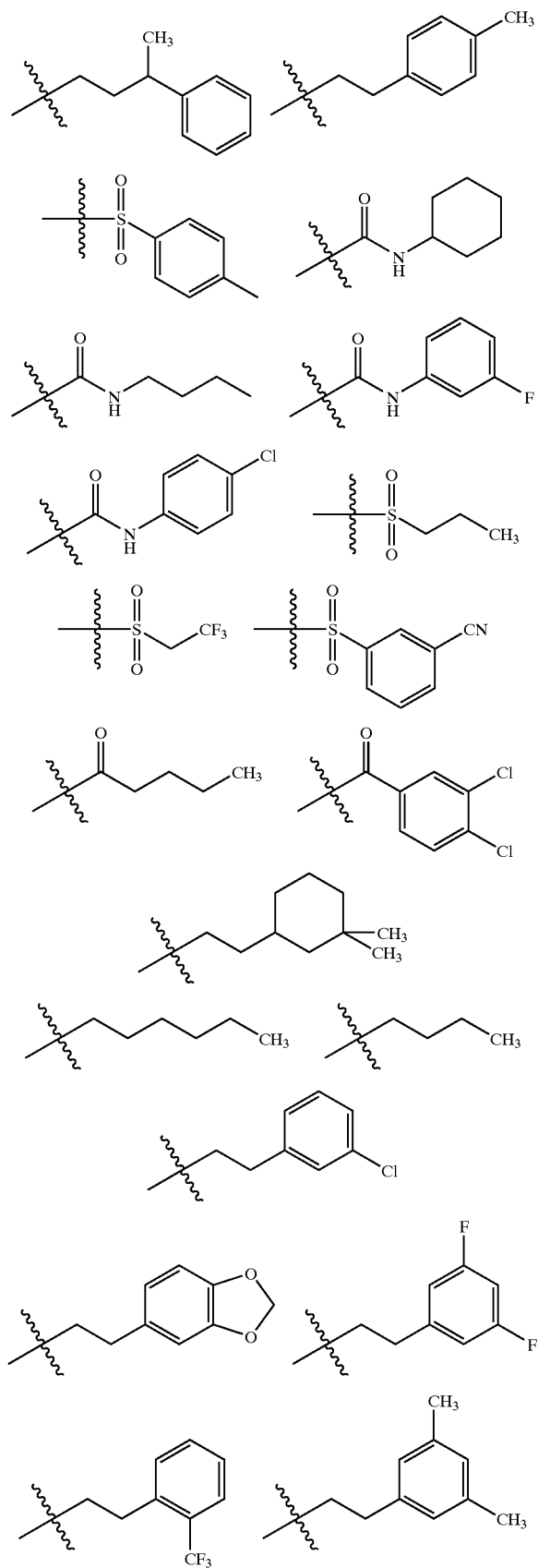
EXAMPLES 193–235
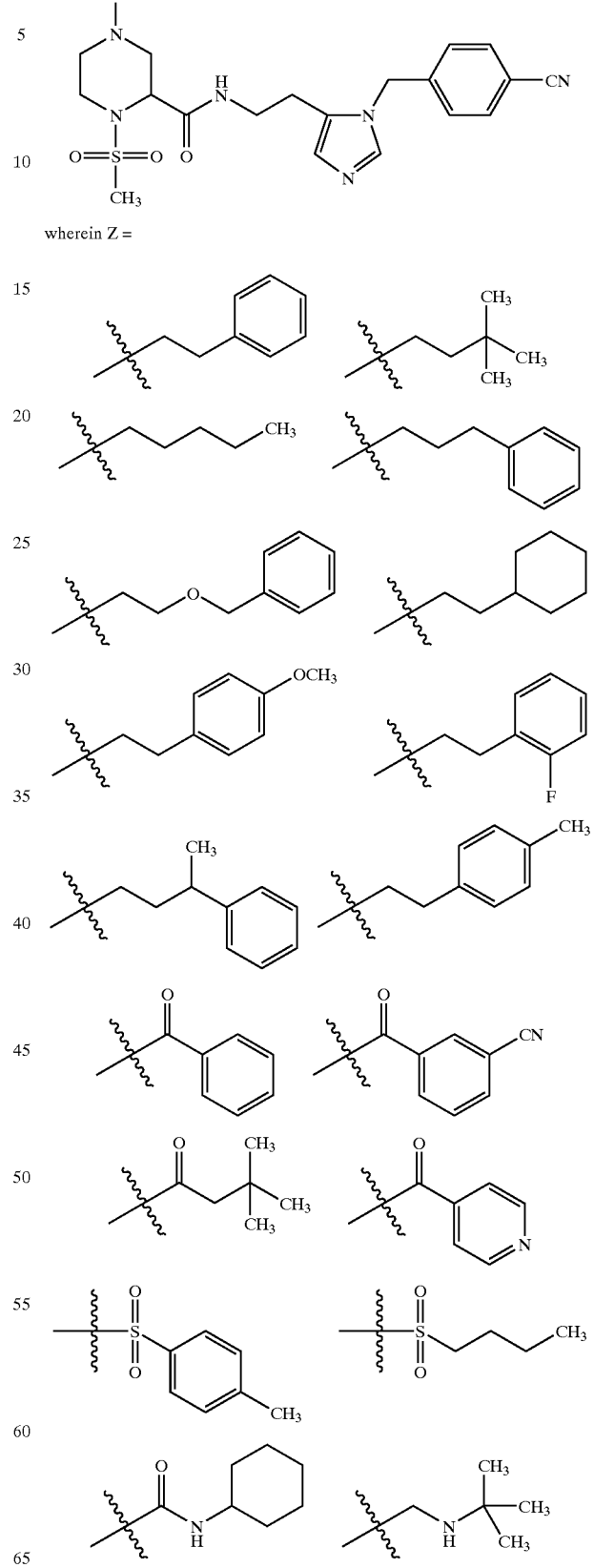
wherein Z =

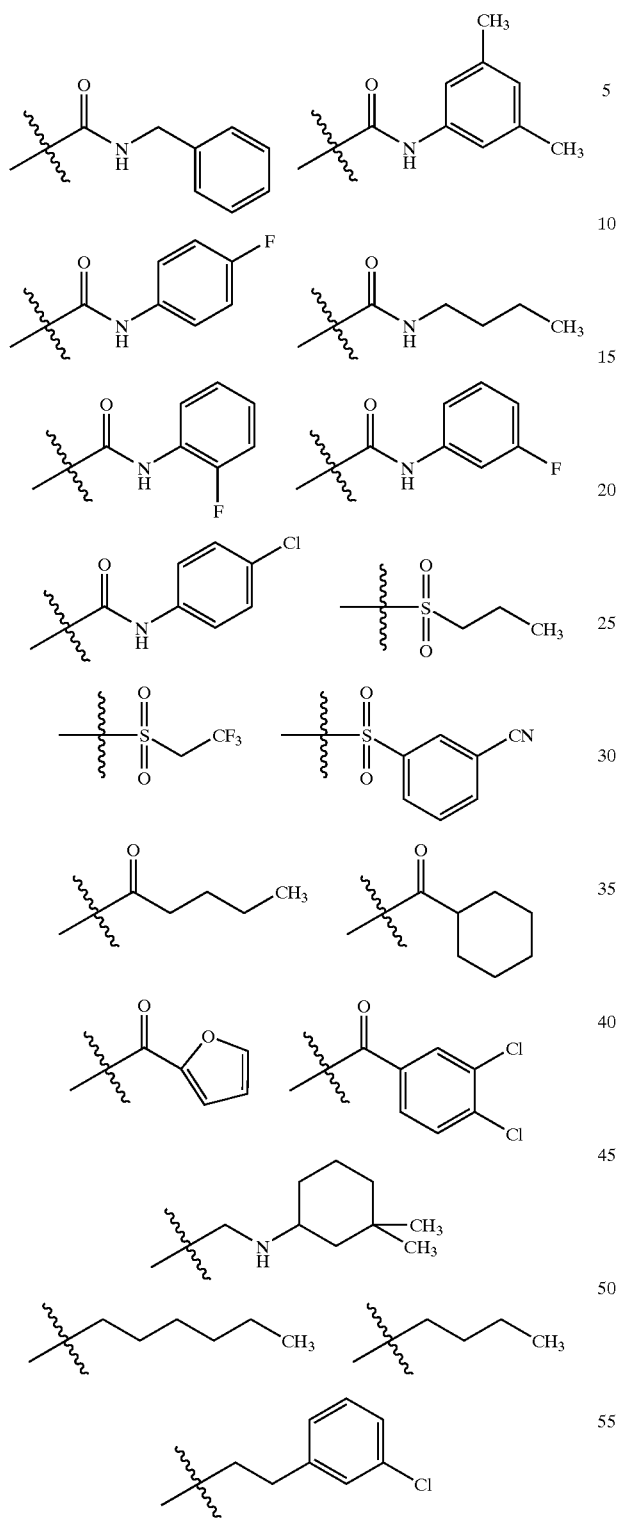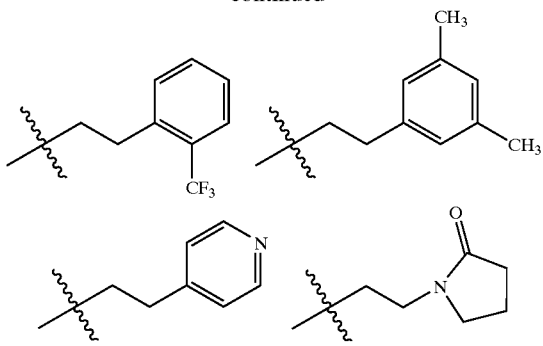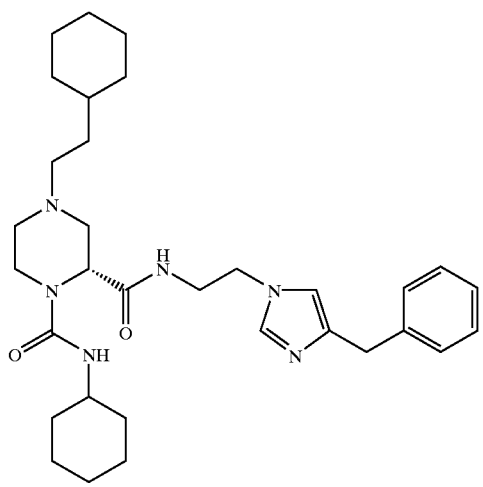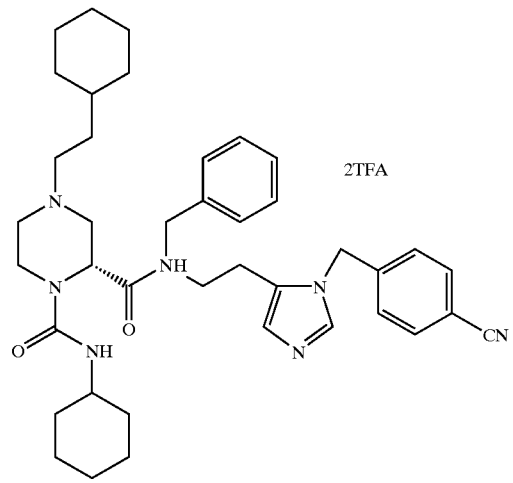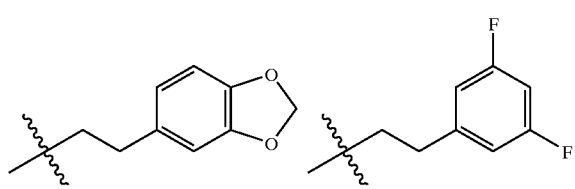

EXAMPLES 236–237

PS204446

PS365776

Preparation of Starting Materials

Starting materials useful in preparing the compounds of the present invention are exemplified by the following preparative examples, which should not be construed to limit the scope of the disclosure. Methods for preparing various starting materials can also be found in references such as, for example, Emmett, J. C., Holloway, F. H., Turner, J. L. J. Chem. Soc., Perkin Trans. 1 1979, 1341–1344 and Abdel-Magid, A. F., Maryanoff, C. A., Carson, K. G. *Tetrahedron Lett.* 1990, 31, 5595.

Preparative Example 1

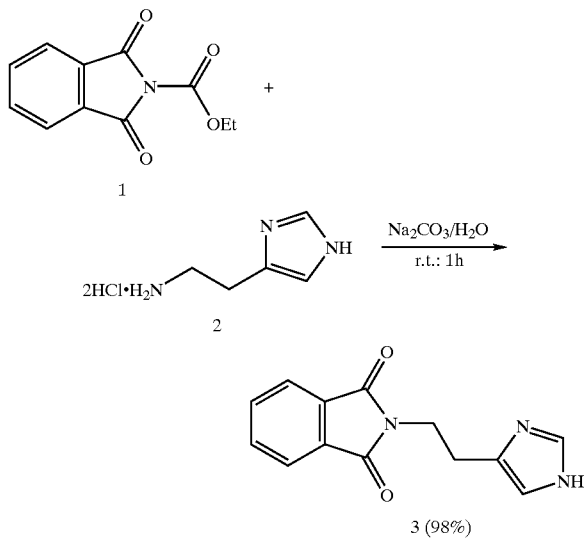

N-Carbethoxyphthalimide 1 (62.8 g, 0.275 mol, 1.1 eq.) is added portionwise over a period of 30 minutes to a stirred solution of histamine dihydrochloride 2 (46.7 g, 0.250 mol, 1.0 eq.) and sodium carbonate (54.3 g, 0.513 mol, 2.05 eq.) in distilled water (1250 ml) at room temperature. The resulting snow-white suspension is stirred vigorously at room temperature for 90 minutes. The solid is filtered off and thoroughly washed with ice-cold distilled water (4×50 ml). The solid is collected and dried under vacuum over $P_2O_5$ at 60° C. for 12 h to give $N^\alpha$-phthaloylhistamine 3 (59.2 g, 0.245 mol, 98%) in high purity (>95% by $^1$H NMR). The snow-white solid is used directly without further purification.

Preparative Example 2

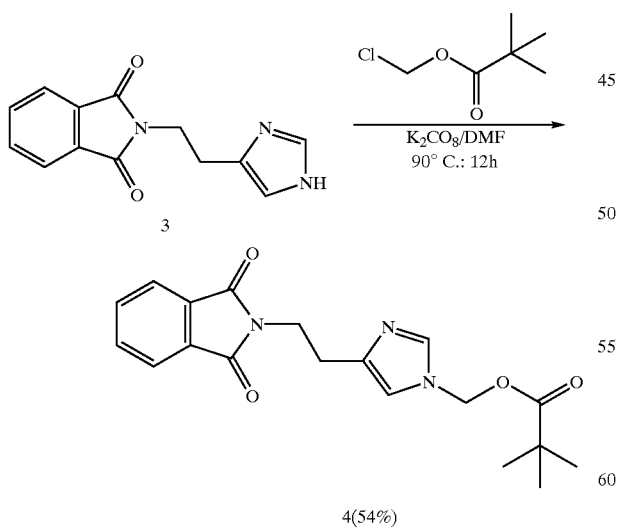

A solution of chloromethyl pivalate (18.5 ml, 0.125 mol, 1.2 eq.) in anhydrous N,N-dimethylformamide (DMF, 100 ml) is added dropwise over a period of one hour to a stirred mixture of 3 (25.0 g, 0.104 mol, 1.0 eq.) and potassium carbonate (17.2 g, 0.125 mol, 1.2 eq.) in anhydrous DMF (500 ml) at 90° C. under a nitrogen atmosphere. The mixture is stirred at 90° C. for 12 h. The volatiles are removed under vacuum at 50° C. The residue is taken up in brine (100 ml) and extracted with ethyl acetate (4×25 ml). The combined organic extracts are dried over $Na_2SO_4$, filtered, and concentrated under vacuum at 30° C. The residual off-white solid is flash-chromatographed (hexanes:acetone=6:4 v/v) over silica gel to give N-pivaloyloxymethyl-N-phthaloylhistamine 4 (20 g, 0.056 mol) as a crystalline, white solid of high purity.

Preparative Example 3

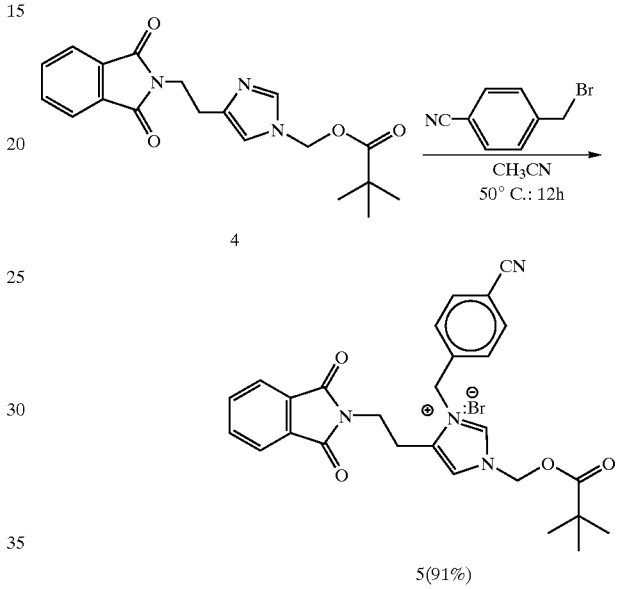

A solution of 4 (10.2 g, 28.7 mmol, 1.0 eq.) and a-bromo-p-tolunitrile (11.4 g, 57.4 mmol, 2.0 eq.) is stirred in anhydrous acetonitrile (150 ml) at 50° C. under a nitrogen atmosphere for 12 h. The resulting snow-white suspension is cooled to room temperature and chilled in a refrigerator at −20° C. for one hour. The precipitate is filtered off and thoroughly washed with ice-cold ethyl acetate (4× 50 ml). The solid is collected and dried under vacuum over $P_2O_5$ at 50° C. for 12 h to give 1-pivaloyloxymethyl-3-(4-cyanobenzyl)-4-(2-phthalimidoethyl)imidazolium bromide 5 (14.4 g, 26.2 mmol).

Preparative Example 3A

1-Pivaloyloxymethyl-3-(4-chlorobenzyl)-4-(2-phthalimidoethyl)imidazolium chloride

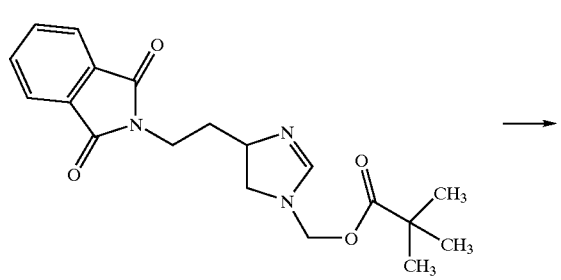

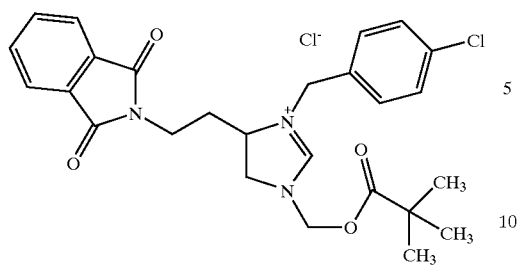

A solution of the title compound from Preparative Example 2 (5 g, 14.1 mmol) and 4-chlorobenzylchloride (2.5 g, 15.5 mmol) was stirred in anhydrous acetonitrile (60 ml) at reflux under a nitrogen atmosphere for 48 h. The mixture was concentrated in vacuo and recrystallized from ethyl acetate-hexane to give the title compound as a solid (3.2 g, MH+=480), and the filtrate which was concentrated to give additional product (3.6 g).

Preparative Example 3B

1-Pivaloyloxymethyl-3-(4-phenylethyl)-4-(2-phthalimidoethyl)imidazolium bromide

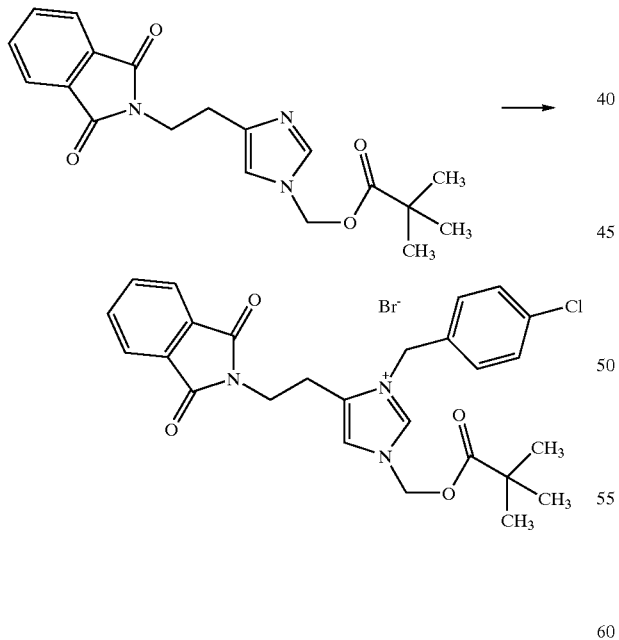

A solution of the title compound from Preparative Example 2 (5 g, 14.1 mmol) and 2-bromoethylbenzene (15.5 mmol, 1.1 eq) is stirred in anhydrous acetonitrile (50 ml) at reflux under a nitrogen atmosphere for 72 h. The mixture is concentrated in vacuo to give the title compound as a sticky oil (100%, MH+=460).

Preparative Example 3C

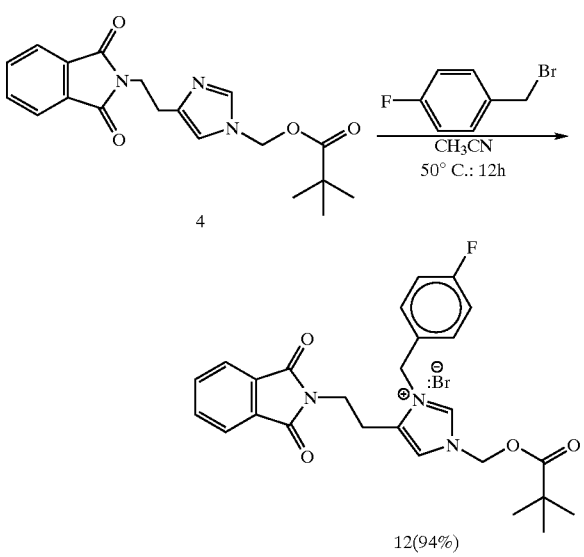

A solution of 4 (3.0 g, 8.4 mmol, 1.0 eq.) and 4-fluorobenzylbromide (2.2 ml, 16.9 mmol, 2.0 eq.) is stirred in anhydrous acetonitrile (50 ml) at 50° C. under a nitrogen atmosphere for 12 h. The resulting snow-white suspension is cooled to room temperature and chilled in a refrigerator at −20° C. for one hour. The precipitate is filtered off and thoroughly washed with ice-cold ethyl acetate (4×25 ml). The solid is collected and dried under vacuum over $P_2O_5$ at 50° C. for 12 h to give 1-pivaloyloxymethyl-3-4-fluorobenzyl)-4-(2-phthalimidoethyl)imidazolium bromide 12 (4.32 g, 7.93 mmol) in 94% yield.

Preparative Example 4.

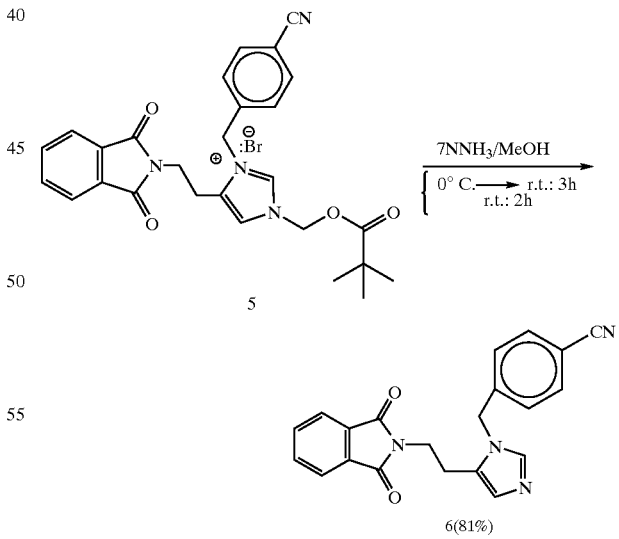

A 7 N solution of ammonia in methanol (75 ml, 0.525 mol, 7.25 eq.) is added dropwise over a period of 75 minutes to a stirred solution of 5 (40 g, 0.073 mol, 1.00 eq.) in anhydrous methanol (1000 ml) at 0° C. under a nitrogen atmosphere. The mixture is slowly (3 h) warmed to ambient temperature and stirred for another 12 h. The volatiles are evaporated under vacuum at 30° C. and the residual white solid is flash-chromatographed (CH$_2$Cl$_2$:2 N NH$_3$/MeOH= 90:10 v/v) over silica gel to give N$^o$-(4-cyanobenzyl)-N$^a$-phthaloylhistamine 6 (21 g, 0.059 mol).

Preparative Example 4A

N-[(4-chlorophenyl)methyl]-N-phthaloylhistamine

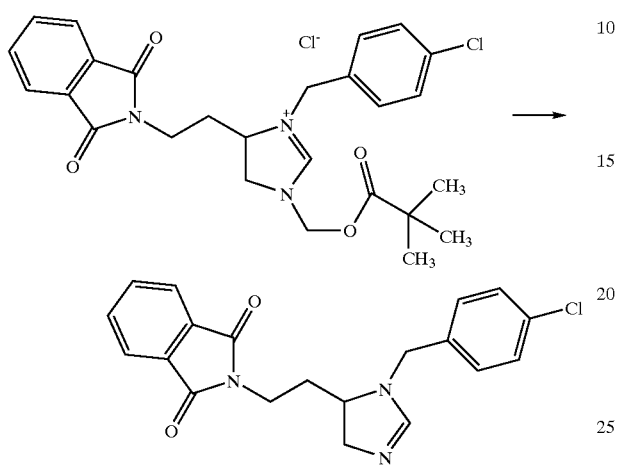

A 7 N solution of ammonia in methanol (10 ml, 0.07 mol) is added slowly to a stirred solution of the title compound from Preparative Example 3A (3.2 g, 6.6 mmol) diluted with MeOH (10 mL) at −20° C. The resulting mixture is warmed to room temperature and stirred for another 12 h, then concentrated in vacuo and purified by flash column chromatography (silica gel) using 3% MeOH—CH$_2$Cl$_2$ saturated with ammonium hydroxide as eluent to afford the title compound as a sticky solid (1.2 g, 51%, MH+=366).

Preparative Example 4B

N-(4-phenylethyl)-N-phthaloylhistamine

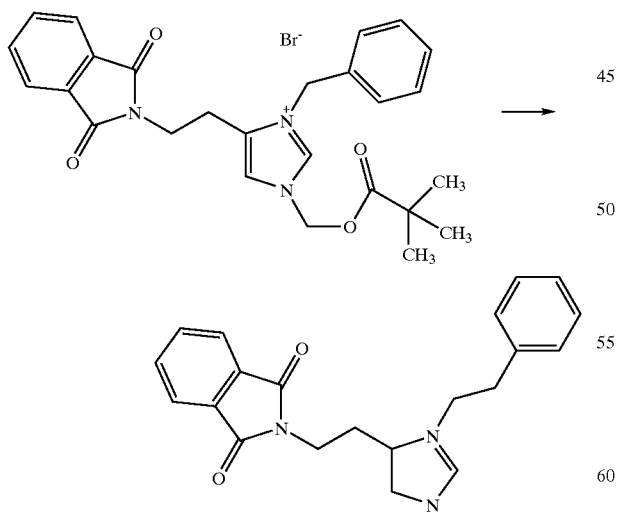

A 7 N solution of ammonia in methanol (23 ml, 0.16 mol) is added slowly to a stirred solution of the title compound from Preparative Example 3B (15.8 mmol) diluted with MeOH (60 mL) at −20° C. The resulting mixture is warmed to room temperature and stirred for another 96 h, then concentrated in vacuo and purified by flash column chromatography (silica gel) using 3% MeOH—CH$_2$Cl$_2$ saturated with ammonium hydroxide as eluent to afford the title compound (1.6 g, MH+=346).

Preparative Example 4C

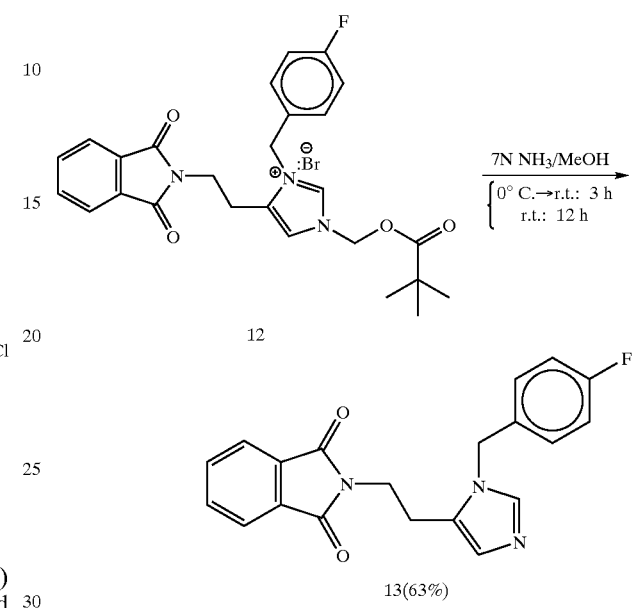

A 7 N solution of ammonia in methanol (8.0 ml, 55.10 mmol, 7.25 eq.) is added dropwise over a period of 10 minutes to a stirred solution of 12 (4.0 g, 7.35 mmol, 1.00 eq.) in anhydrous methanol (50 ml) at 0° C. under a nitrogen atmosphere. The mixture is slowly (3 h) warmed to ambient temperature and stirred for another 12 h. The volatiles are evaporated under vacuum at 30° C. and the residual white solid is flash-chromatographed (CH$_2$Cl$_2$: 2 N NH$_3$/MeOH= 97:3 v/v) over silica gel to give N$^o$-(4-fluorobenzyl)-N$^a$-phthaloylhistamine 13 (1.62 g, 4.63 mmol, 63%) as a snow-white solid.

Preparative Example 5

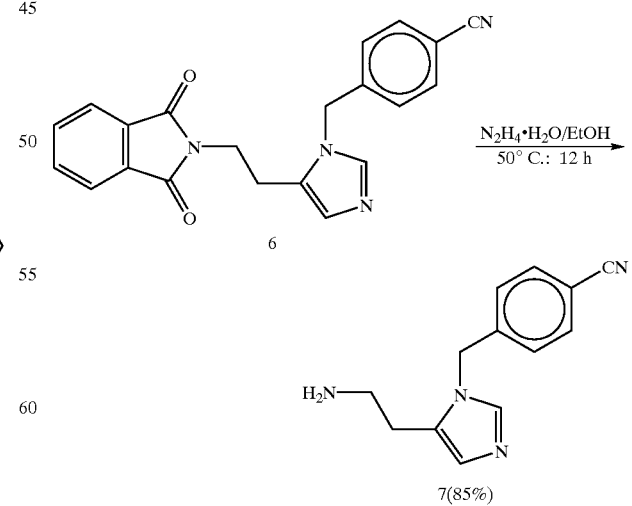

A solution of 6 (21 g, 0.059 mol, 1.0 eq.) and hydrazine monohydrate (15 ml, 0.884 mol, 15.0 eq.) in absolute ethanol (250 ml) is stirred at 50° C. under a nitrogen atmosphere for 12 h. The snow-white suspension is cooled to room temperature and chilled in a refrigerator at −20° C. for one hour. The precipitate (phthalyl hydrazide) is filtered off and thoroughly washed with ice-cold ethanol (190 proof, 500 ml). The filtrates are combined and concentrated under vacuum at 30° C. The residue is subjected to flash column chromatography (CH$_2$Cl$_2$:2 N NH$_3$/MeOH=90:10 v/v) over silica gel to give N$^\circ$-(4-cyanobenzyl)histamine 7 (11.4 g, 0.050 mol, 85%) as a thick, light-brown oil.

Preparative Example 5A

N-[(4-chlorophenyl)methyl]-histamine

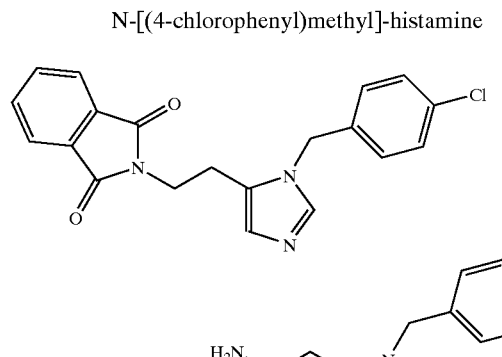

A solution of the title compound from Preparative Example 4A (1.21 g, 3.3 mmol) and hydrazine monohydrate (1.7 ml, 0.033 mol, 10 eq.) in absolute ethanol (20 ml) is stirred at 50° C. under a nitrogen atmosphere for 20 min. The resulting suspension is diluted with ethanol and dichloromethane and filtered. The filtrate is concentrated in vacuo to afford the title compound as a yellow oily solid (0.7 g, MH$^+$=236).

Preparative Example 5B

N-(phenylethyl)histamine

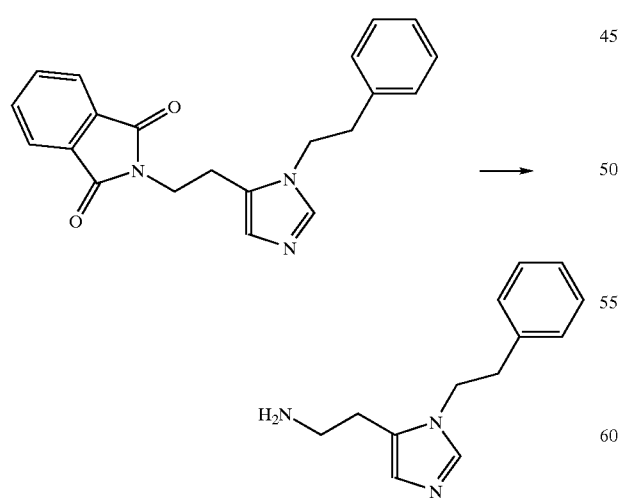

A solution of the title compound from Preparative Example 4B (1.54 g, 4.4 mmol) and hydrazine monohydrate (2.2 ml, 0.044 mol, 10 eq.) in absolute ethanol (25 ml) is stirred at 50° C. under a nitrogen atmosphere for 20 min, then at room temperature overnight. The resulting suspension is diluted with ethanol and dichloromethane and filtered. The filtrate is concentrated in vacuo to afford the title compound as an oily solid (0.88 g, MH$^+$=216).

Preparative Example 5C

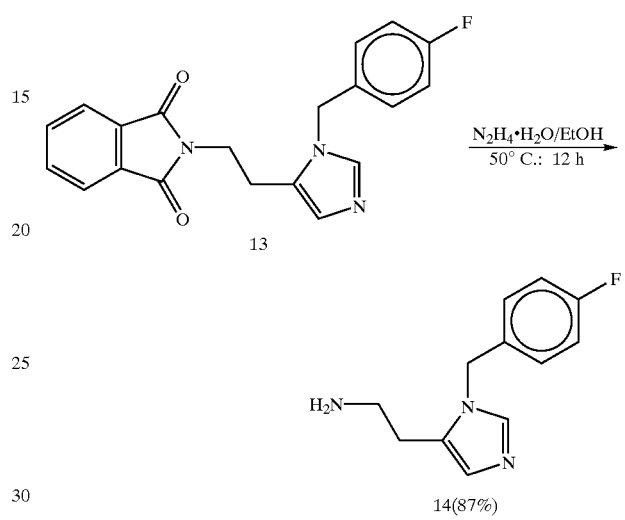

A solution of 13 (1.6 g, 4.6 mmol, 1.0 eq.) and hydrazine monohydrate (1.1 ml, 22.9 mmol, 5.0 eq.) in absolute ethanol (25 ml) was stirred at 50° C. under a nitrogen atmosphere for 12 h. The snow-white suspension was cooled to room temperature and chilled in a refrigerator at −20 ° C. for one hour. The precipitate (phthalyl hydrazide) was filtered off and thoroughly washed with ice-cold ethanol (190 proof, 50 ml). The filtrates were combined and concentrated under vacuum at 30° C. The residue was flash column chromatographed (CH$_2$Cl$_2$: 2 N NH$_3$/MeOH=90: 10 v/v) over silica gel to give N$^\circ$-(4-fluorobenzyl)histamine 14 (870 mg, 3.97 mmol, 87%) as a brown oil.

Preparative Examples 8 and 9.

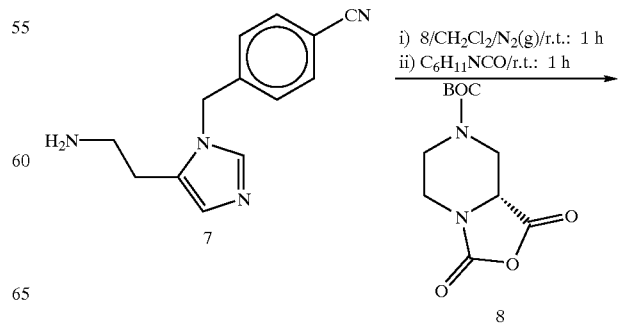

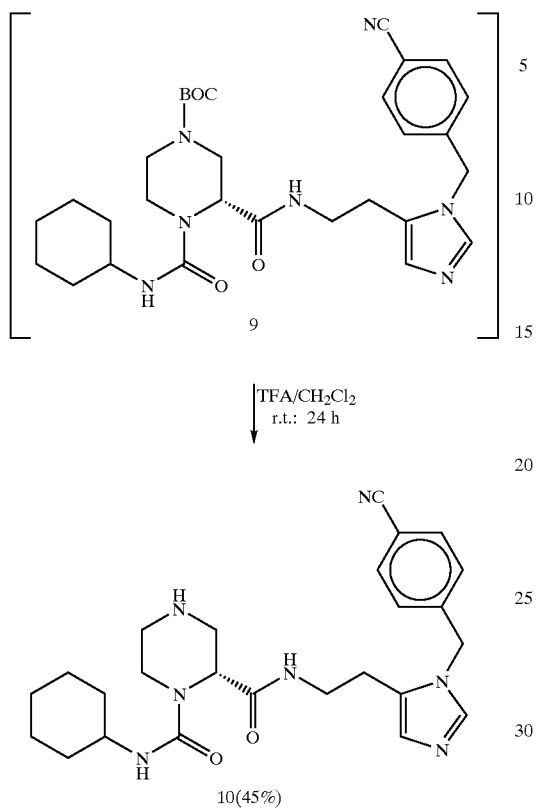

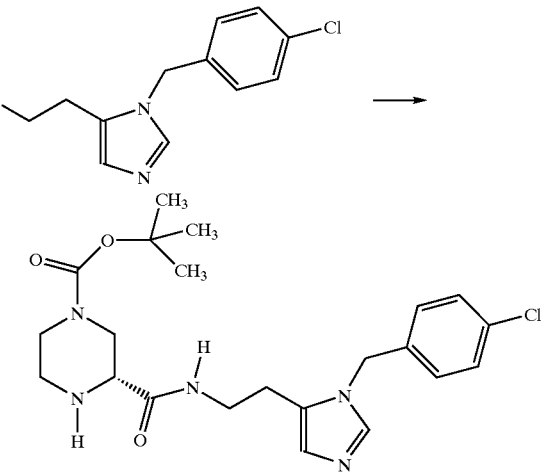

Preparative Example 10A

N4-(1,1-dimethylethyloxycarbonyl)-N2-[2-[1-[(4-chlorophenyl)methyl]-1H-imidazol-5-yl]ethyl]-1,2(R)-piperazinecarboxamide A solution of the title compound from Preparative Example 5A (0.695 g, 2.94 mmol) and the anhydride from Preparative Example (0.75 g, 2.94 mmol) dissolved in anhydrous dichloromethane (10 ml) is stirred at room temperature overnight. Additional anhydride (0.1 g) is added and after 1 hr the reaction mixture is diluted with $CH_2Cl_2$ and extracted with 1 M HCl (aq). The aqueous phase is basified with 1N NaOH (aq), extracted with $CH_2Cl_2$ and the organic phase dried over anhydrous $MgSO_4$. After filtration, the organic phase is concentrated in vacuo to afford a white foam (0.744 g, $MH^+$=448).

A solution of 7 (1.50 g, 6.63 mmol, 1.0 eq.) in anhydrous dichloromethane (30 ml) is added dropwise over a period of 30 minutes to a stirred solution of 15 anhydride 8 (2.04 g, 7.95 mmol, 1.2 eq.) in anhydrous dichloromethane (30 ml) at room temperature. A stream of nitrogen is bubbled through the solution to expel evolved carbon dioxide. The colorless solution is stirred for one hour amid nitrogen bubbling. Bubbling is terminated and cyclohexyl isocyanate (1.75 ml, 13.26 mmol, 2.0 eq.) is added dropwise over a period of 5 minutes. The brown solution is stirred at room temperature for one hour to give 9 (confirmed by $^1H$ NMR). The volatiles are removed under vacuum at 30° C. The residue is taken up in a mixture of trifluoroacetic acid (TFA, 30 ml) and anhydrous dichloromethane (30 ml) and is stirred at ambient temperature under a nitrogen atmosphere for 24 h. The mixture is concentrated under vacuum at 30° C. The residual light-brown oil is taken up in 1 N aqueous NaOH solution (100 ml) and extracted with dichloromethane (4×25 ml). The combined organic extracts are washed with brine (25 ml), dried over $Na_2SO_4$, filtered, and concentrated under vacuum at 30° C. The resulting oil is flash-chromatographed ($CH_2Cl_2$: 2 N $NH_3$/MeOH=90: 10 v/v) over silica gel to give N2-[2-[1-[(4-cyanophenyl)methyl]-1H-imidazol-5-yl]ethyl]-N1-cyclohexyl-1,2(R)-piperazinedicarboxamide 10 (1.34 g, 2.95 mmol) as a light-yellow foam.

Preparative Example 10B

N4-(1,1-dimethylethyloxycarbonyl)-N2-[2-[1-(phenylethyl)-1H-imidazol-5-yl]ethyl]-1,2(R)-piperazinecarboxamide

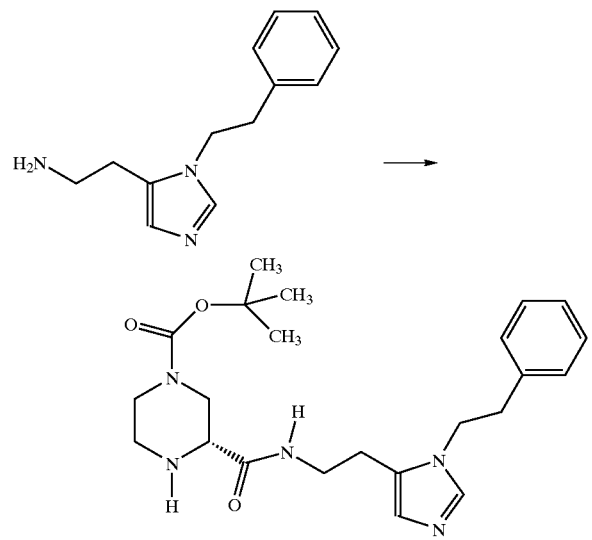

A solution of the title compound from Preparative Example 5B (0.874 g, 4.04 mmol) and the anhydride from Preparative Example (1.04 g, 4.04 mmol) dissolved in anhydrous dichloromethane (10 ml) is stirred at room temperature overnight. Additional anhydride (0.23 g) is added and after 1 hr the reaction mixture is diluted with CH$_2$Cl$_2$ and extracted with 1 M HCl (aq). The aqueous phase is basified with 1 N NaOH (aq), extracted with CH$_2$Cl$_2$ and the organic phase dried over anhydrous MgSO$_4$. After filtration, the organic phase is concentrated in vacuo to afford a white foam (1.22 g, 710%, MH$^+$=428).

Preparative Example 10

N4-(1,1-dimethylethyloxycarbonyl)-N2-[2-[1-[(4-cyanophenyl)methyl]-1H-imidazol-5-yl]ethyl]-1,2(R)-piperazinecarboxamide

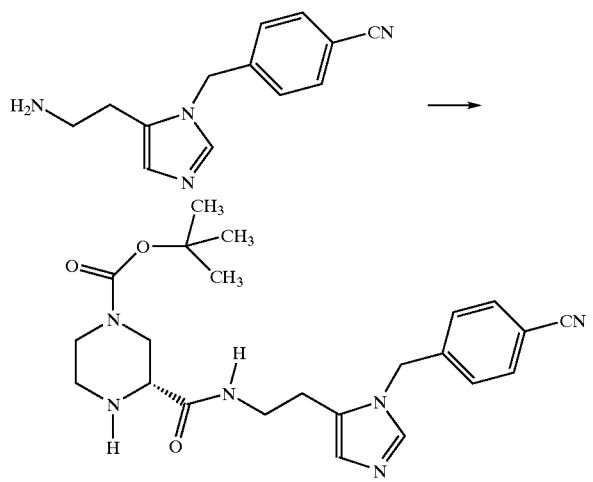

A solution of the title compound from Preparative Example 5 (7.8 g, 34.5 mmol), triethylamine (10 mL) and the anhydride from Preparative Example (10 g, 39.0 mmol) dissolved in anhydrous dichloromethane (300 ml) is stirred at room temperature overnight. The reaction mixture is concentrated in vacuo, diluted with CH$_2$Cl$_2$ and extracted with 1 M HCl (aq). The aqueous phase is basified with 1 N NaOH (aq), extracted with CH$_2$Cl$_2$ and the organic phase dried over anhydrous MgSO$_4$. After filtration, the organic phase is concentrated in vacuo to afford the title compound (10.0 g, MH$^+$=448).

Preparative Example 11

N2-[2-[1-[(4-cyanophenyl)methyl]-1H-imidazol-5-yl]ethyl]-N4-phenyl-1,2(R)-piperazinecarboxamide

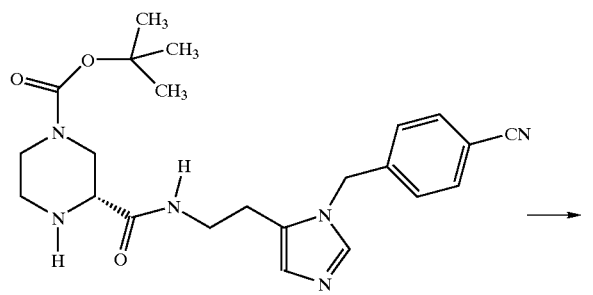

-continued

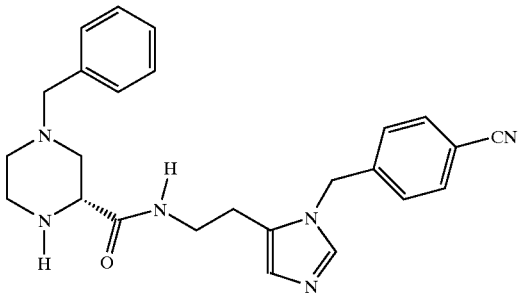

A solution of the title compound from Preparative Example 10 (5 g, 1.1.4 mmol) dissolved in anhydrous dichloromethane (50 ml) and trifluoroacetic acid (10 ml) is stirred at room temperature for 1 hr, then concentrated in vacuo. The residue is combined with benzaldehyde (1.4 mmol) and diluted with glacial acetic acid (25 mL) and anhydrous dichloromethane (100 ml), then cooled to 0° C. Sodium triacetoxyborohydride (4.83 g, 22.8 mmol) is added and the resulting mixture is stirred at 0° C. for 2 h, then at room temperature overnight. The reaction mixture is concentrated in vacuo, diluted with dichloromethane and extracted with 1 N HCl (aq). The aqueous phase is basified with 1 N NaOH (aq) and extracted with dichloromethane, then dried over anhydrous Na$_2$SO$_4$, filtered, concentrated in vacuo. Flash column chromatography (silica gel) using 10% MeOH—CH$_2$Cl$_2$ saturated with ammonium hydroxide as eluent affords the title compound (1.5 g, MH$^+$=428).

Preparative Example 12

N2-[2-[1-[(4-chlorophenyl)methyl]-1H-imidazol-5-yl]ethyl]-N1-cyclohexyl-1,2(R)-piperazinecarboxamide

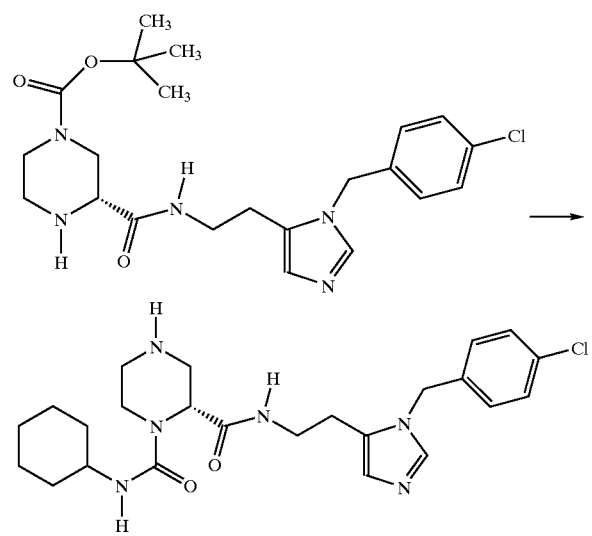

To a solution of the title compound from Preparative Example 10A (0.30 g, 0.67 mmol) dissolved in anhydrous dichloromethane (3 ml) is added cyclohexylisocyanate (0.09 mL, 0.7 mmol) and the resulting solution was stirred at room temperature for 30 min, then concentrated in vacuo. The resulting residue is diluted with dichloromethane (3 ml) trifluoroacetic acid (3 ml). The solution is stirred at room temperature overnight, then concentrated in vacuo, diluted with dichloromethane and washed with 1 N NaOH (aq). The organic phase is dried over anhydrous MgSO$_4$, filtered, and concentrated in vacuo to afford a yellow foam (0.319 g, MH$^+$=473).

Preparative Example 12A

N2-[2-[1-(phenylethyl)-1H-imidazol-5-YL]ethyl]-N1-cyclohexyl-1,2(R)-piperazinedicarboxamide

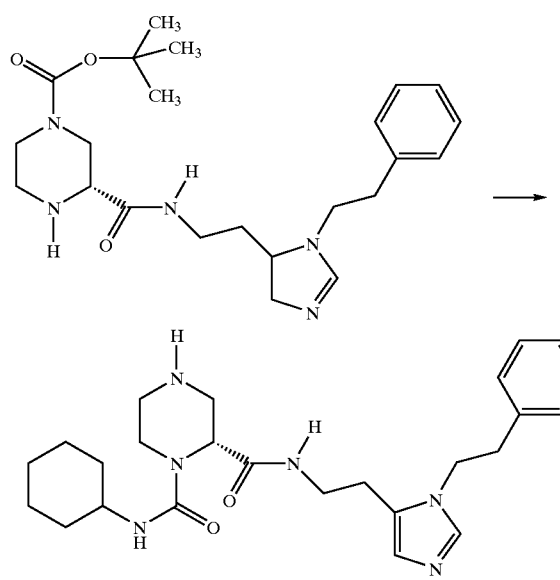

To a solution of the title compound from Preparative Example 10 B (0.33 g, 0.77 mmol) dissolved in anhydrous dichloromethane (3 ml) is added cyclohexylisocyanate (0.11 mL, 0.9 mmol) and the resulting solution is stirred at room temperature for 30 min, then concentrated in vacuo. The resulting residue is diluted with dichloromethane (3 ml) trifluoroacetic acid (3 ml). The solution is stirred at room temperature overnight, then concentrated in vacuo, diluted with dichloromethane and washed with 1 N NaOH (aq). The organic phase is dried over anhydrous MgSO$_4$, filtered, and concentrated in vacuo to afford a yellow foam (0.338 g, MH$^+$=453).

Preparative Example 13.

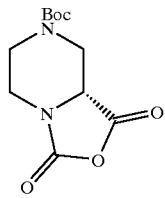

Step a. 2-R-carboxyl-piperazine-di-(R)-(-)-camphorsulfonic

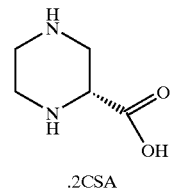

.2CSA

To 2.5 kg of (R)-(-)-camphorsulfonic acid stirring at 60° C. in 1250 ml of distilled water are added a solution of the potassium salt of 2-carboxyl-piperazine (565 gm, 3.35 mol). The mixture is allowed to stir at 95° C. until completely dissolved. The solution is allowed to stand at ambient temperature for 48 hrs. The resulting precipitate is filtered to obtain 1444 gm of damp solid. The solids are then dissolved in 1200 ml of distilled water and heated on a steam bath until all solids dissolved. The hot solution is then set aside to cool slowly for 72 hrs. The crystalline solids are filtered to give 362 gm of pure product as a white crystalline solid. [a]$_D$=–14.9°

Step b. N,N-di-tert.butoxycarbonyl-2-R-carboxyl-piperazine

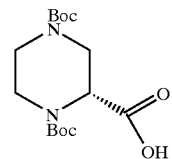

2-R-carboxyl-piperazine-di-(R)-(-)-camphorsulfonic (362 gm, 0.608 mol) from Step a. is dissolved in 1.4 L of distilled water and 1.4 L of methanol. 75 ml of 50% NaOH are dripped in to the stirred reaction mixture to obtain an about pH=9.5 solution. To this solution is added di-tert.butyl-dicarbonate (336 gm, 1.54 mol) as a solid. The pH drops to about 7.0. The pH of the reaction mixture is maintained at 9.5 with 50% NaOH (total of 175 ml), and the reaction mixture is stirred for 2.5 hours to obtain a white precipitate. The reaction mixture is diluted to 9 L with ice/water followed by washing with 2 L of ether. The ether is discarded and the pH of the aqueous layer is adjusted to pH 3.0 by the portionwise addition of solid citric acid. The acidified aqueous layer is then extracted with dichloromethane 3× with 2 L. The organic layers are combined, dried over sodium sulfate, filtered and evaporated to obtain 201.6 gm of title compound as a white glassy solid. FABMS (M+1)=331

Step c. "N-Boc-piperazine-2-amidoanhydride"

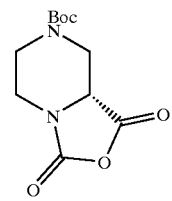

To an ice cold solution N,N-dimethylformamide (49.6 ml) is added, dropwise, thionylchloride (46.7 ml) over a period of 5 minutes in a 5 L round bottom flask under a nitrogen atmosphere The reaction mixture is allowed to stir for 5 min.

and the ice bath removed and the reaction mixture allowed to stir at ambient temperature for 30 min. The reaction mixture is cooled again in an ice bath and a solution of of N,N-di-butoxycarbonyl-2-R-carboxyl-piperazine (201.6 gm, 0.61 mmol) from Step b. in 51.7 ml of pyridine and 1.9 L of acetonitrile are cannulated into the reaction mixture. The reaction mixture is allowed to warm to ambient to obtain a yellowish turbid solution. After stirring at ambient temperature for 18 hours, the reaction mixture is filtered and the filtrate poured into ice water (7 L) and then extracted with 4×2 L of ethylacetate, dried over sodium sulfate, filtered and evaporated to dryness under vacuo to obtain 115.6 gm of the title product as a white solid. FABMS (M+1)=257.

Preparative Example 14

[2-(2-methyl-1H-benzimidazol-1-yl)ethyl]amine

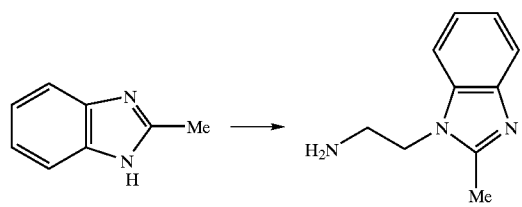

A mixture of 2-methylbenzimidazole (4.93 g, 37.3 mmol), 2-chloroethylamine hydrochloride (4.67 g, 40.3 mmol), tetrabutylammonium sulfate (0.51 g, 1.5 mmol), sodium hydroxide (5.37 g, 134.2 mmol) and acetonitrile (80 mL) are stirred at reflux for 48 hrs. The resulting mixture is cooled to room temperature, filtered and concentrated in vacuo. The residue is purified by flash column chromatography (silica gel) using 1–3% MeOH—CH$_2$Cl$_2$ saturated with ammonium hydroxide as eluent to afford the title compound (3.56 g, MH$^+$=176).

Preparative Example 15

[2-(2,4-dimethylimidazol-1-yl)ethyl]amine and [2-(2,5-dimethylimidazol-1-yl)ethyl]amine

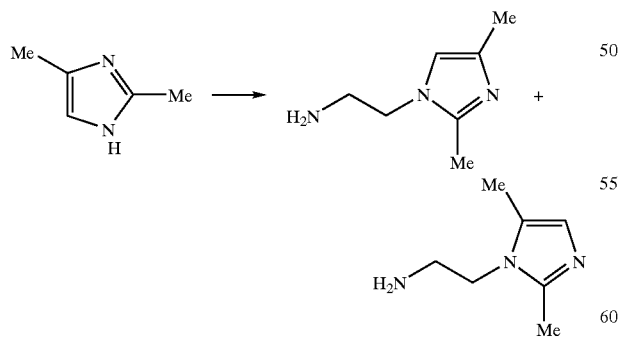

Following a similar procedure used in Preparative Example 14, but using 2,4-dimethylimidazole instead of 2-methylbenzimidazole, the title compounds were prepared as a mixture of regioisomers (10.7 g, MH$^+$=).

Preparative Example 16

3-(1H-imidazol-1-yl)propyl-phenylmethylamine

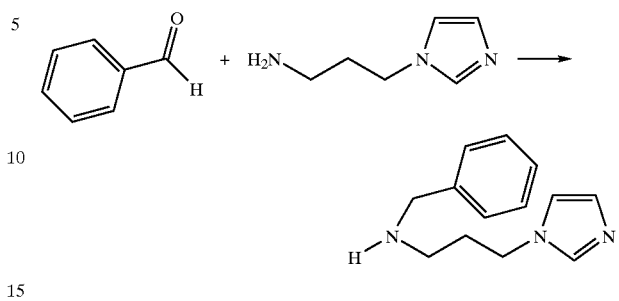

A mixture of 1-(3-aminopropyl)imidazole (Aldrich, 37.1 g, 297 mmol), benzaldehyde (30 g, 283 mmol), 3 Å molecular sieves (50 g), sodium acetate (24.1 g, 283 mmol) and anhydrous methanol (700 mL) are stirred at room temperature under N$_2$ overnight. The mixture is cooled to 0° C. and sodium borohydride (10.9 g, 288 mmol) is added portionwise over 1 hour. The mixture is stirred at room temperature for 3 hours. The mixture is filtered through celite, washed with methanol, and concentrated in vacuo to give a residue which is diluted with dichloromethane and washed with 10% aqueous sodium hydroxide. The organic phases are washed with brine, dried over anhydrous magnesium sulfate, filtered and concentrated in vacuo to give the title compound as a pale yellow oil (56.3 g, MH$^+$=216).

Preparative Example 17

2(R)-[[[3-(1H-imidazol-1-yl)propyl](phenylmethyl)amino]carbonyl]piperazine

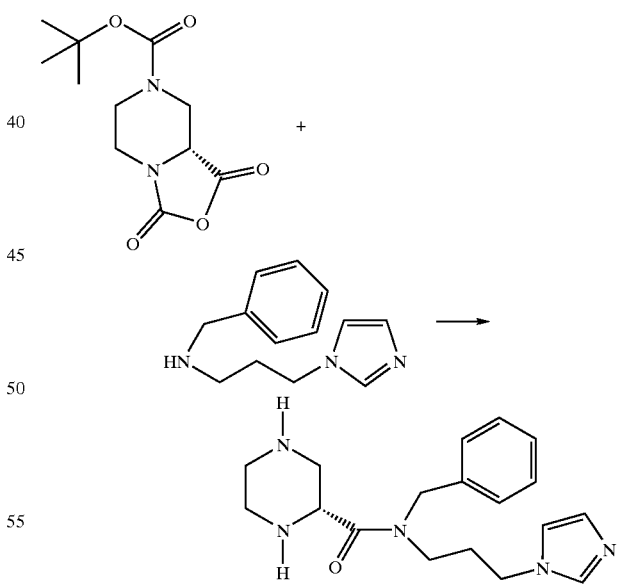

A mixture of the title compound from Preparative Example 16 (1.34 g, 6.2 mmol), the title compound from Preparative Example 13 (1.6 g, 6.2 mmol), triethylamine (1.3 mL, 9.3 mmol) and anhydrous CH$_2$Cl$_2$ (10 mL) are stirred at room temperature for 48 hrs. Trifluoroacetic acid (10 mL) is added and the resulting mixture is stirred for an additional 1.5 hrs. Aqueous NaOH (1 N) is added dropwise to neutralize the reaction mixture and the resulting mixture is extracted with $CH_2Cl_2$. The organic phase is dried over anhydrous $MgSO_4$, filtered and concentrated in vacuo to give a residue which is purified by flash column chromatography (silica gel) using 1% MeOH-99% $CH_2Cl_2$ saturated with aqueous ammonium hydroxide to give the title compound as an oil (520 mg, $MH^+=328$).

Preparative Example 18

Ethyl 4-piperidinyl acetate

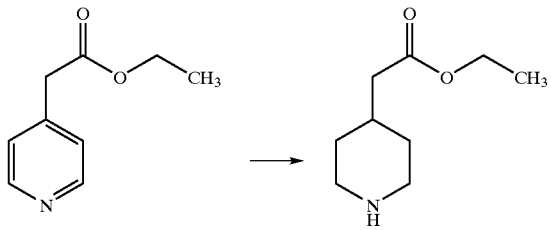

Ethyl 4-pyridyl acetate (4.5 g, 27.24 mmoles) is placed in a 500 mL Parr bottle and dissolved in anhydrous EtOH (70 mL). To the bottle is added 10% Palladium on charcoal (1.0 g). The bottle is put on a hydrogenator and the contents shaken under 55 psi hydrogen pressure at 25° C. for 94 h. The mixture is filtered through Celite® and washed with 4×40 mL anhydrous EtOH. The filtrate is rotovapped down and the residue chromatographed on silica gel using 3% (10% conc. $NH_4OH$ in methanol)dichloromethane as the eluant to give 2.944 g of the title compound.

Preparative Example 19

Ethyl 1-aminocarbonyl-4-piperidinyl acetate

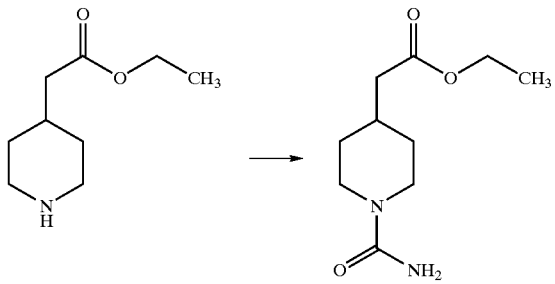

Ethyl 4-piperidinyl acetate (500 mg; 2.92 mmoles) is dissolved in anhydrous $CH_2Cl_2$ (25 mL). To the stirring solution is added trimethylsilyl isocyanate (5.9 mL; 43.8 mmoles) and the solution is stirred at 25° C. for 17 h. The solution is worked up in $CH_2Cl_2$-saturated $NaHCO_3$ and the product chromatographed on silica gel using 2→3%(conc. $NH_4OH$ in methanol)dichloromethane as the eluant to give 622 mg of the title compound.

Preparative Example 20

1-Aminocarbonyl-4-piperidinylacetic acid

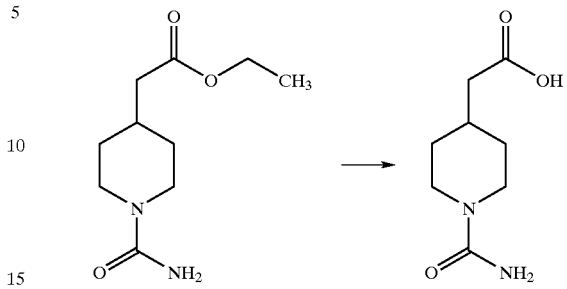

Ethyl 1-aminocarbonyl-4-piperidinyl acetate (153.6 mg, 0.717 mmoles) is dissolved in anhydrous $CH_2Cl_2$ (3.58 mL) and EtOH (3.58 mL). To the solution is added 1.0M LiOH (1.73 mL, 1.73 mmoles) and the mixture is stirred at 50° C. for 5.5 h. The mixture is cooled quickly to 25° C. and 1.0N HCl (2.02 mL, 2.02 mmoles) is added and the mixture stirred for 5 minutes and then rotovapped to dryness to give the title compound which is used without further purification.

Preparative Example 21

Step A:

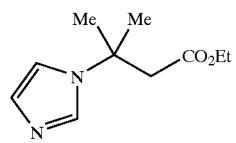

Ethyl 2,2-dimethyl acrylate (50.0 g, 2.0 eq.) is stirred with imidazole (13.28 g, 200 mmol) at 900 for 48 hours. The resulting solution is cooled, diluted with water (150 mL) and $CH_2Cl_2$ (150 mL) and separated. The aqueous layer is washed with $CH_2Cl_2$ (2×75 mL) and the combined organics are dried over $Na_2SO_4$ and concentrated in vacuo. The crude mixture is purified by flash chromatography using a 10% MeOH in $CH_2Cl_2$ solution as eluent to give pure product as a clear oil (11.27 g).

Step B:

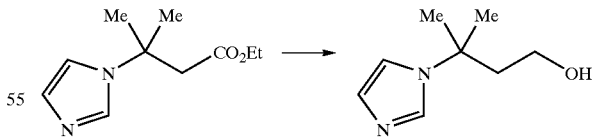

A solution of the title compound from Step A (10.0 g, 50.96 mmol) is treated with $LiAlH_4$ (51 mL, 1 M solution in ether, 1.0 eq.). The reaction mixture is stirred one hour at room temperature before quenching by the dropwise addition of saturated $Na_2SO_4$ (~3.0 mL). The resulting slurry is dried with $Na_2SO_4$ (solid), diluted with EtOAc (100 mL) and filtered through a plug of Celite. The filtrate is concentrated to give a yellow oil (6.87, 87% yield) which is used without further purification.

Step C:

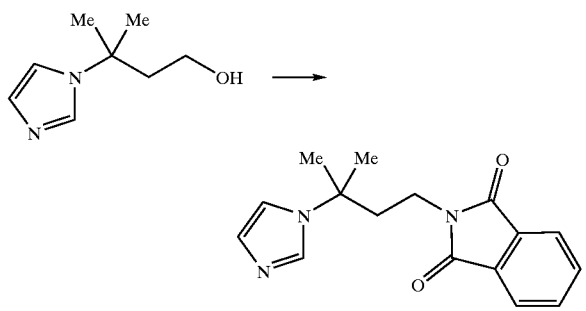

To a solution of the title compound Step B (6.85 g, 44.42 mmol), phthalimide (7.19 g, 1.1 eq.), and triphenylphosphorous (Ph$_3$P) (12.82 g, 1.1 eq.) in THF (200 mL) at 0° C. is added DEAD(7.69 mL, 1.1 eq.) over 10 minutes. The resulting solution is warmed to room temperature and stirred 48 hours. The reaction mixture is concentrated under reduced pressure and the product isolated by crystallization from CH$_2$Cl$_2$/Et$_2$O to give a white solid (10.03 g).

Step D:

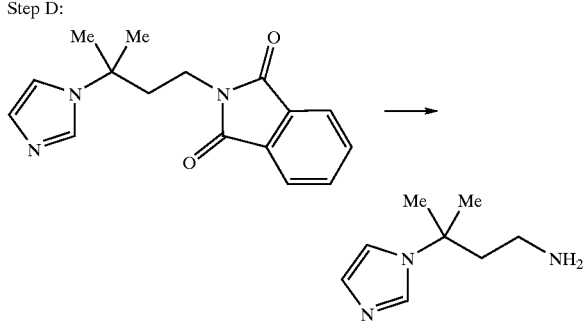

A solution of the title compound from Step C (9.50 g, 33.53 mmol) and (N$_2$H$_4$) (1.25 mL, 1.2 eq.) in EtOH (100 mL) is heated at reflux 4 hours. The resulting slurry is cooled, filtered, and the filtrate concentrated under reduced pressure. The crude product is purified by flash chromatography using a 15% (10% NH$_4$OH in MeOH) solution in CH$_2$Cl$_2$ as eluent to give a pale yellow oil (2.80 g).

Preparative Example 22

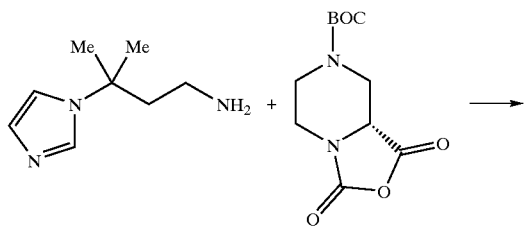

-continued

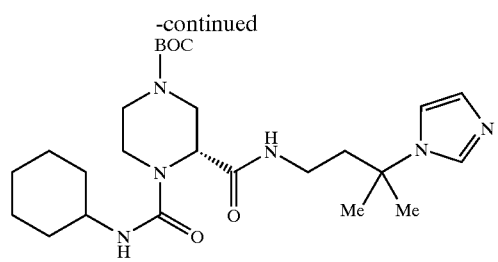

Piperazine anhydride (0.28 g, 1.0 eq.) is added portionwise to a solution of the title compound from Step D of Preparative Example 21 (0.17 g, 1.2 mmol) in CH$_2$Cl$_2$ (5:0 mL) and the resulting solution is stirred 10 minutes at room temperature before adding cyclohexyl isocyanate (0.21 mL, 1.5 eq.). After stirring at room temperature 15 minutes, the reaction mixture is quenched by the addition of MeOH (1 mL), concentrated in vacuo, and purified by flash chromatography using a 10% MeOH in CH$_2$Cl$_2$ solution as eluent to yield a white solid (0.46 g). mp=71–74° C.

Preparative Example 23

Step A:

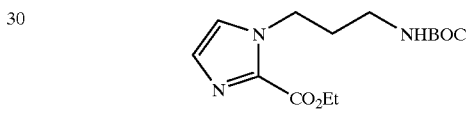

n-BuLi (2.79 mL; 1.75M in hexanes; 2.2 eq.) is added dropwise to a solution of N-BOC aminopropylimidazole (0.50 g, 2.22 mmol) in THF (15 mL) at −78° C. The resulting solution is warmed to −20° C. and stirred two hours before adding TMSCl (0.65 mL, 2.3 eq.). The reaction mixture is warmed to room temperature, stirred one hour, recooled to −78° C. and treated with ClCO$_2$Et (0.25 g, 1.2 eq.). The resulting solution is warmed to room temperature and stirred 60 hours. The reaction is quenched by the addition of water (10 mL) and extracted with CH$_2$Cl$_2$ (3×20 mL). The combined organics are dried over Na$_2$SO$_4$, filtered, and concentrated in vacuo. The crude product is purified by flash chromatography using a 5% MeOH in CH$_2$Cl$_2$ solution as eluent (0.35 g, 53% yield).

Step B:

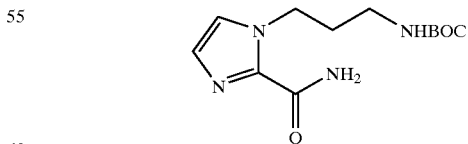

A solution of the title compound from Step A (0.35 g, 1.18 mmol) is stirred in EtOH (10 mL) and 30% NH$_4$OH (2 mL) for 24 hours. The reaction mixture is concentrated under reduced pressure and purified by flash chromatography using neat EtOAc as eluent (0.23 g).

Preparative Example 24

Step A:

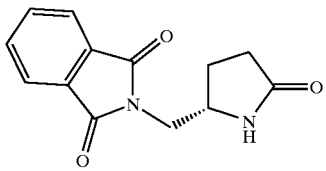

By using essentially the same procedure set forth in Step C of Preparative Example 21 except using S-(+)-5-hydroxymethyl-2-pyrrolidinone (1.0 g, 8.69

Step B:

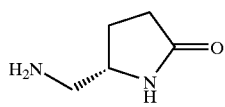

By using essentially the same procedure as set forth in Step D of Preparative Example 21 except using the title compound from Step A of Preparative Example 24 (1.50 g, 6.14 mmol), the title compound is prepared (0.59 g).

Preparative Example 25

Step A:

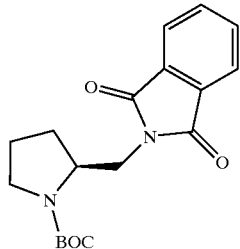

By essentially the same procedure set forth in Step C of Preparative Example 21 except using N-BOC-S-prolinol (0.50 g, 2.48 mmol), the title compound is prepared (0.59 g).

Step B:

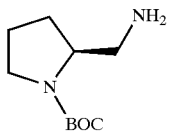

By essentially the same procedure set forth in Step D of Preparative Example 21 except using the title compound from Step A of Preparative Example 25 (0.59 g, 1.79 mmol), the title compound is prepared (0.36 g).

Step C:

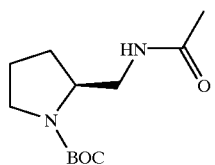

$Ac_2O$ (0.20 mL, 1.2 eq.) is added to the title compound from Step B Preparative Example 25 (0.36 g, 1.80 mmol) and TEA (0.30 mL, 1.2 eq.) in $CH_2Cl_2$ (8.0 mL). The resulting solution is stirred 2 hours and quenched by the addition of saturated $NaHCO_3$ (10 mL). The resulting solution is extracted with $CH_2Cl_2$ (2×20 mL), dried over $Na_2SO_4$, and concentrated in vacuo. The crude product is purified by flash chromatography eluting first with neat EtOAc followed by 5% MeOH in EtOAc (0.23 g).

Assays

1. In vitro enzyme assays: FPT $IC_{50}$ (inhibition of farnesyl protein transferase, in vitro enzyme assay) are determined by the methods disclosed in WO/10515 or WO95/10516. The data demonstrate that the compounds of the invention are inhibitors of Ras-CVLS farnesylation by partially purified rat brain farnesyl protein transferase (FPT). The data also show that there are compounds of the invention which can be considered as potent ($IC_{50}$<10 $\mu$M) inhibitors of Ras-CVLS farnesylation by partially purified rat brain FPT.

Compounds of Examples 1–3, 5–28, 28A–28X, 28Y1, 28Y2, 28Z, 28Z1, 28Z2, 29–57, 57A, 58–62, and 64–67 h ad an FPT $IC_{50}$ within the range of 0.18 nM to 4000 nM (nM represents nanomolar).

Compounds of Examples 1, 5, 6, 8–17, 20–28, 28C, 28E, 28F, 28G, 28I, 28M, 28O, 28P, 28Q, 28R, 28S, 28T, 28V, 28Y1, 28Y2, 29, 31, 32, 34, 36–38, 42, 43, 47, 53–56, 58, 61 and 64 h ad an FPT $IC_{50}$ within the range of 0.18 nM to 21 nM.

Compounds 20, 25, 26, 27, 28, 28O, 54 and 55 had an FPT $IC_{50}$ within the range of 0.18 nM to 1.5 nM.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10–16 days at 37° C. under 5% $CO_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the IC50's can be determined.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound selected from the group consisting of:

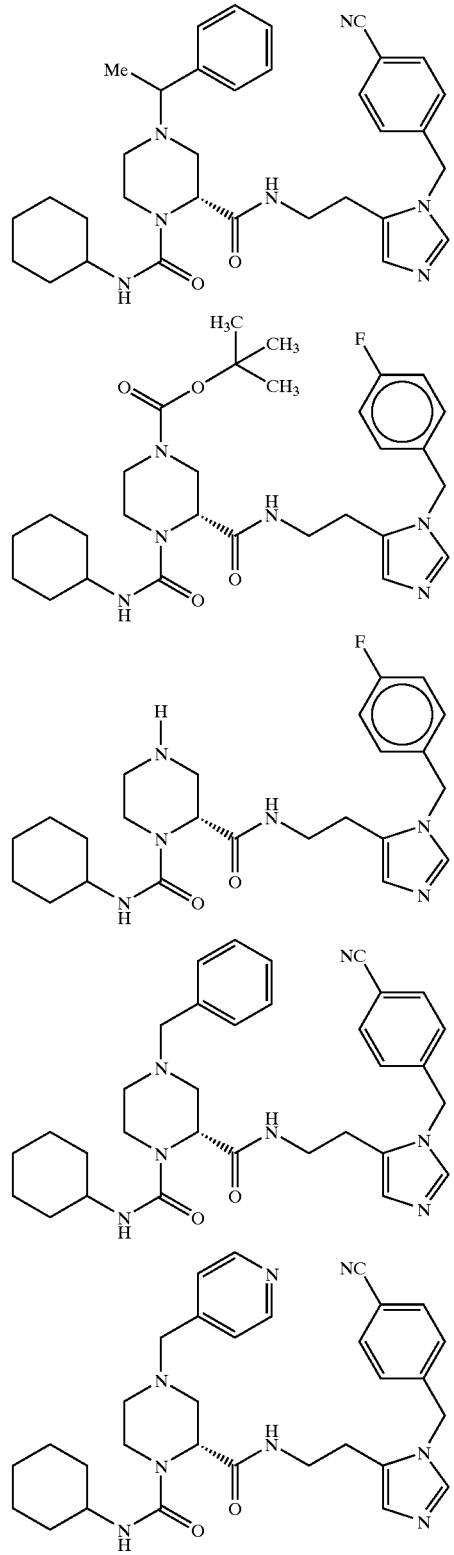

111
-continued
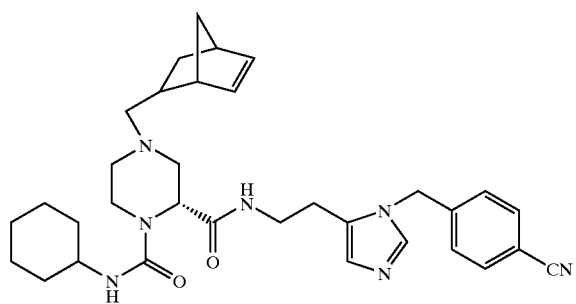
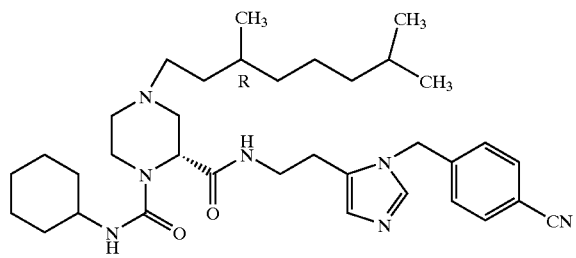
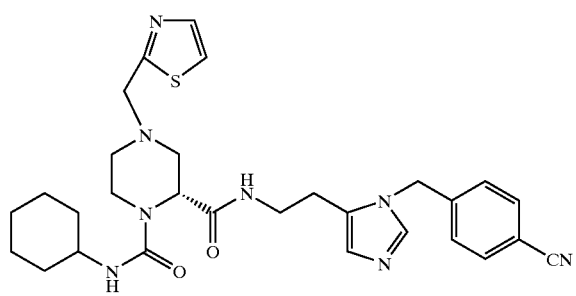
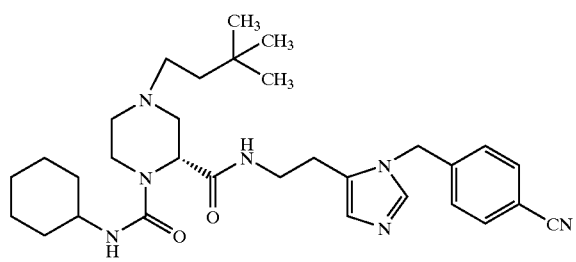
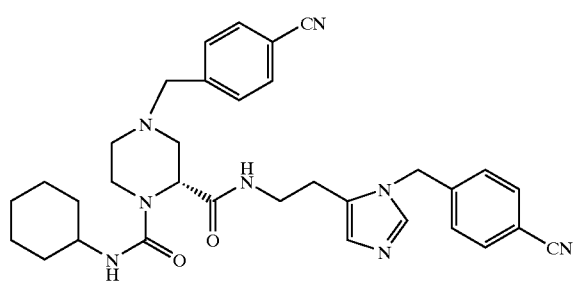
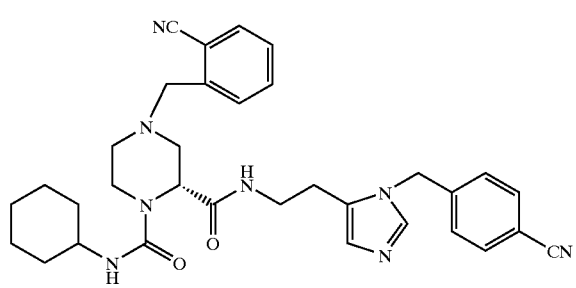
112
-continued
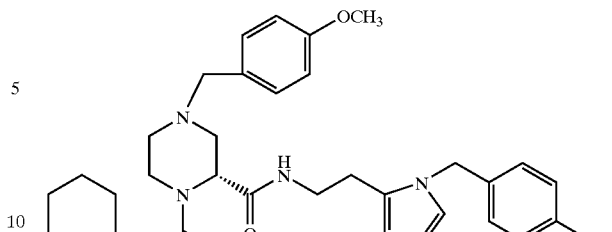
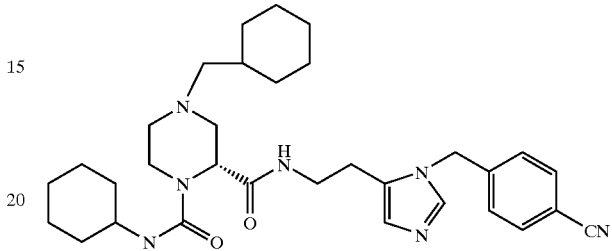
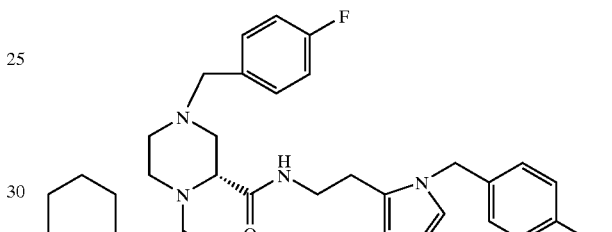
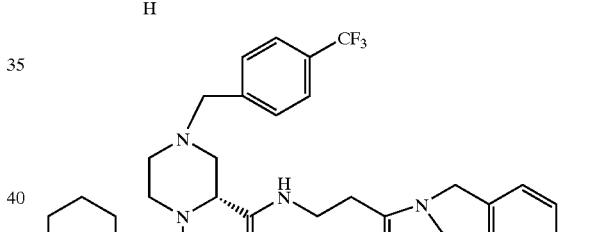
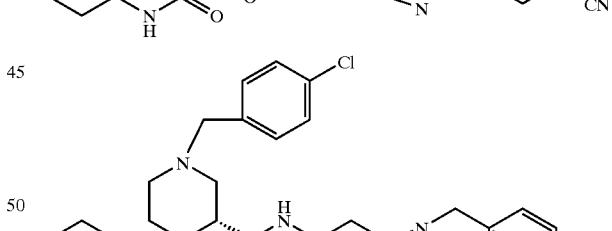
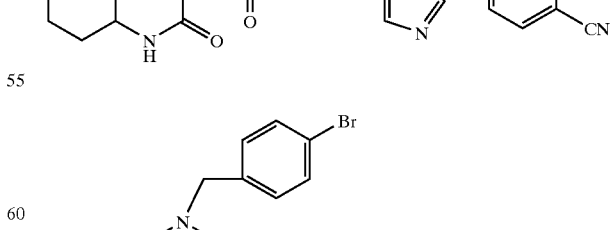

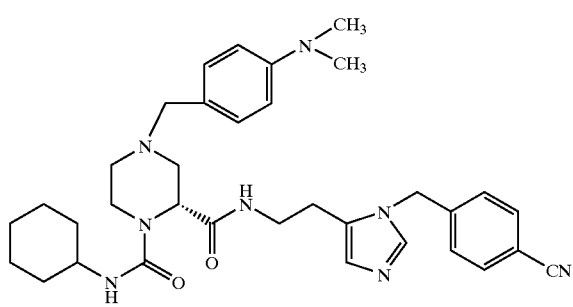
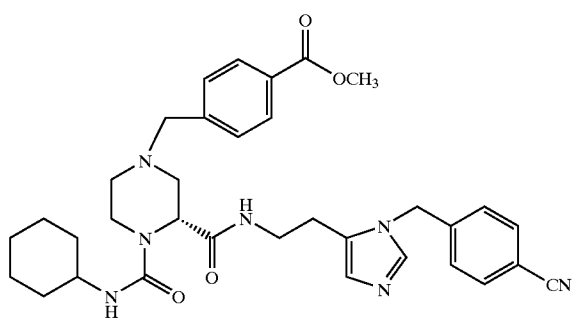
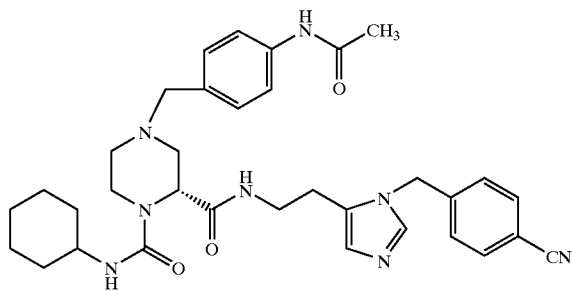
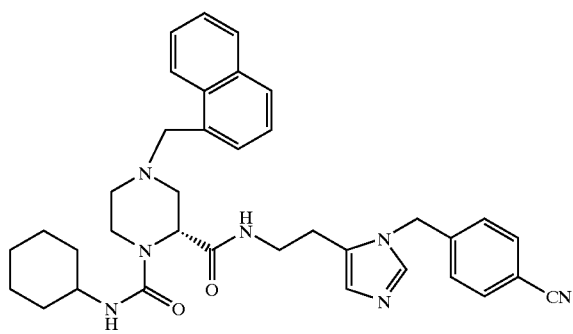
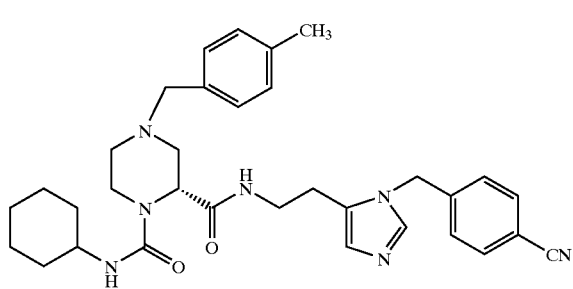
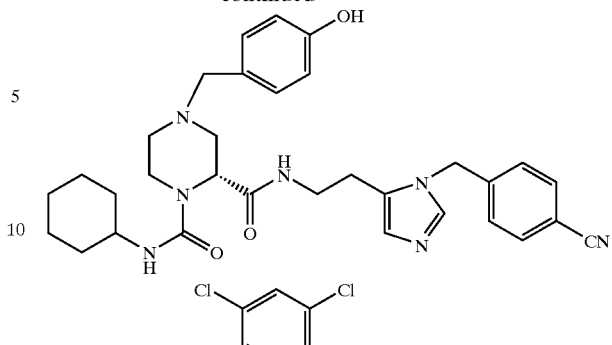
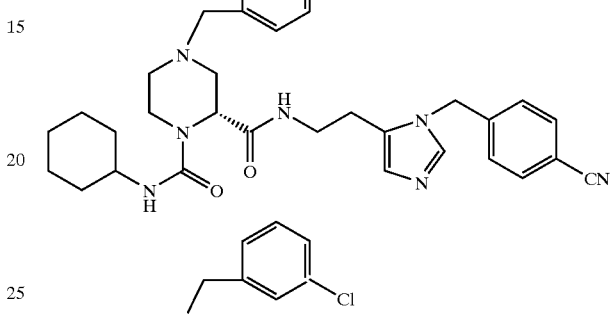
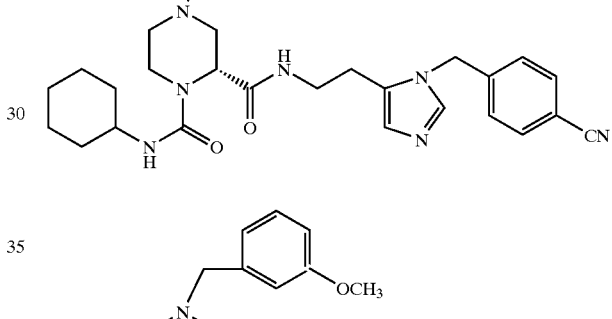
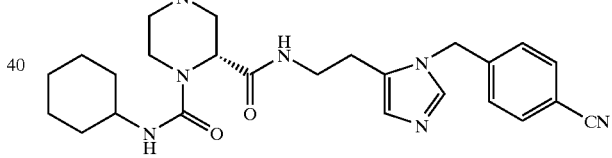
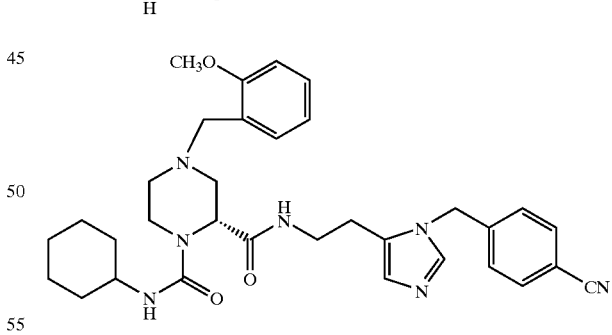
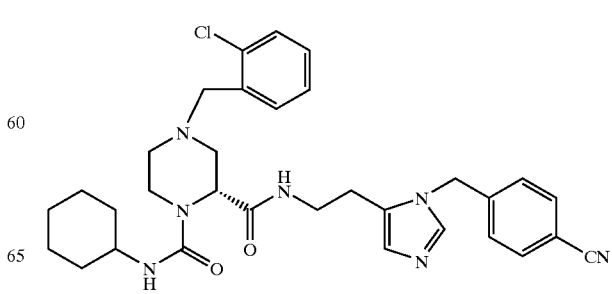

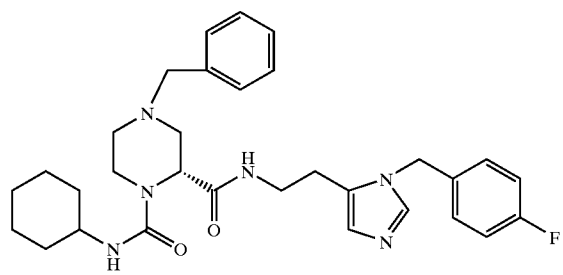
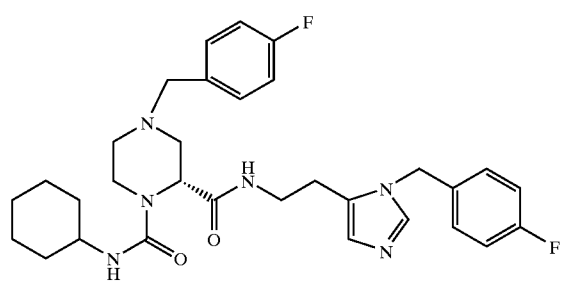
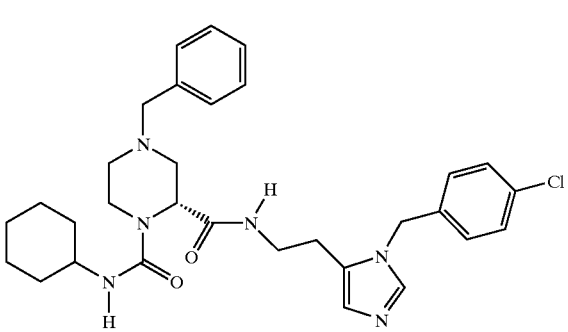
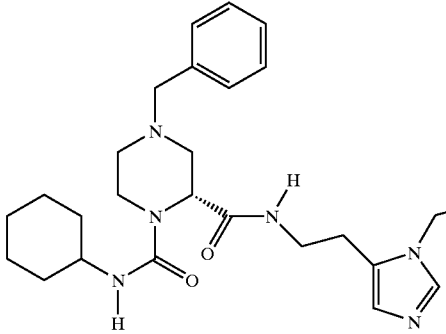
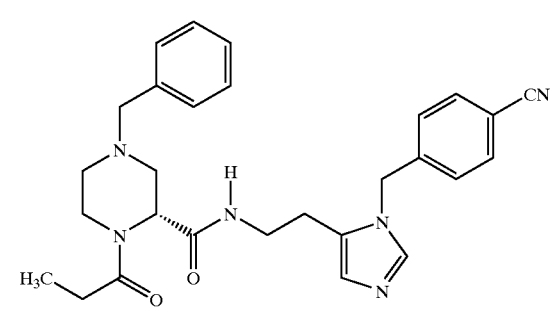
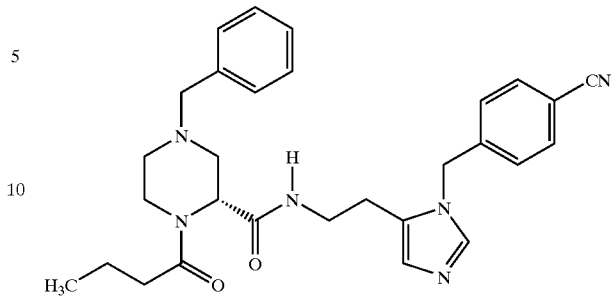
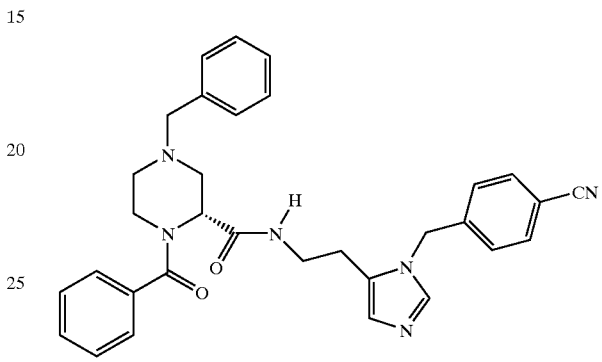
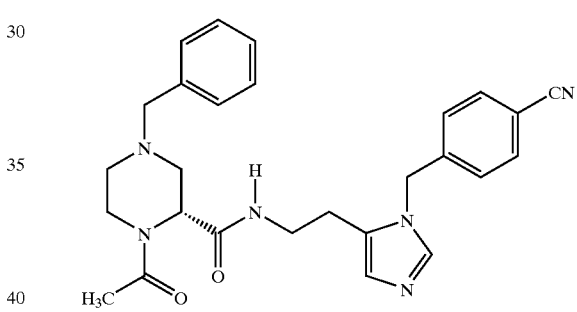
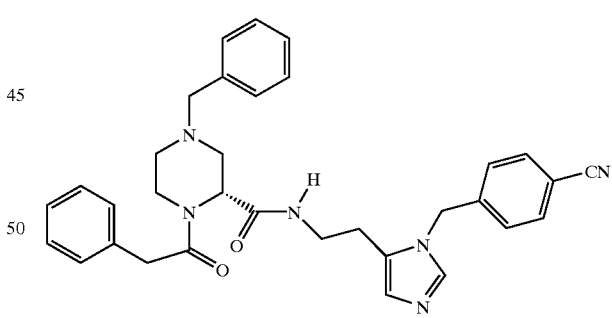
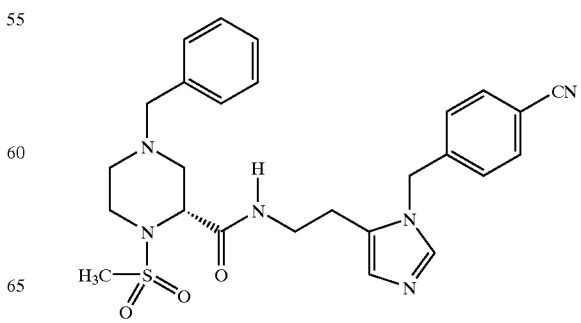

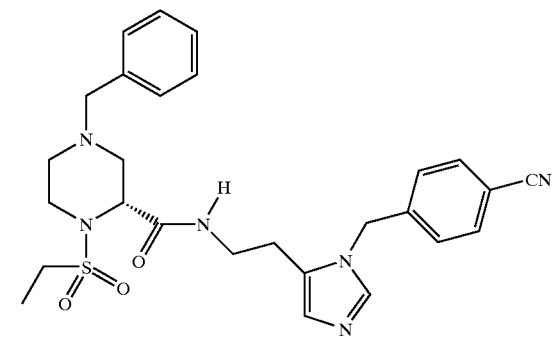
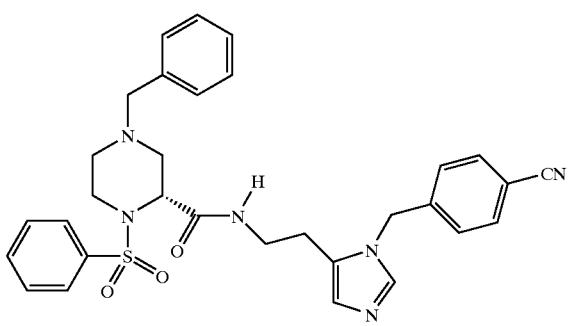
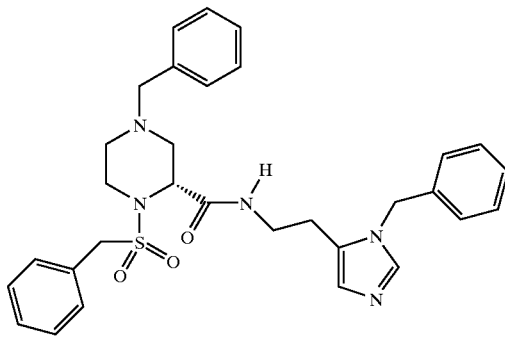
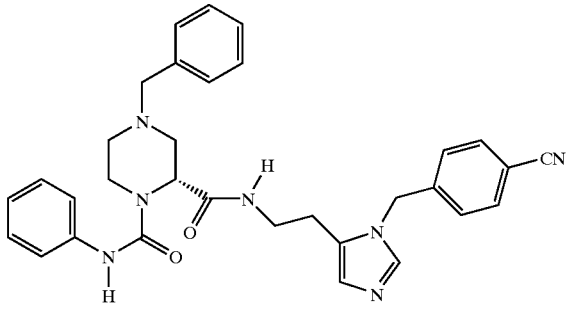
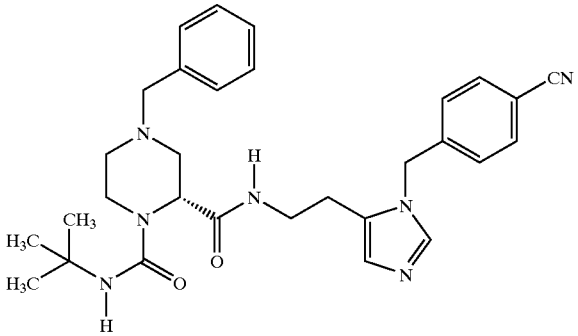
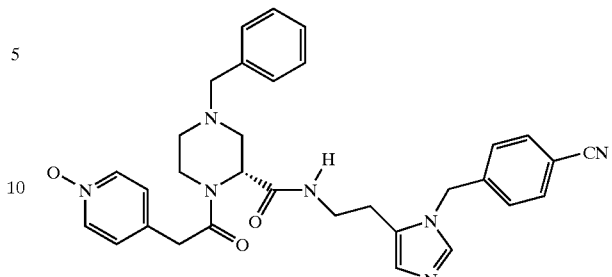
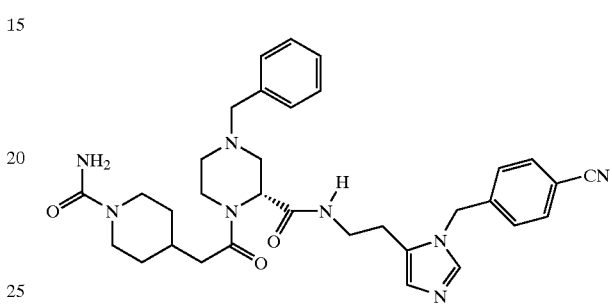
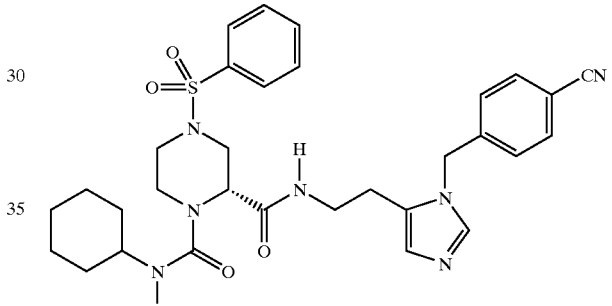
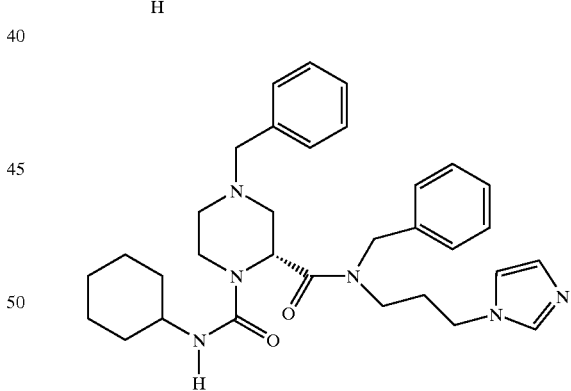
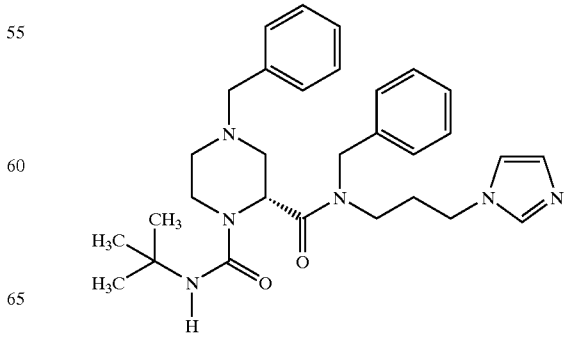

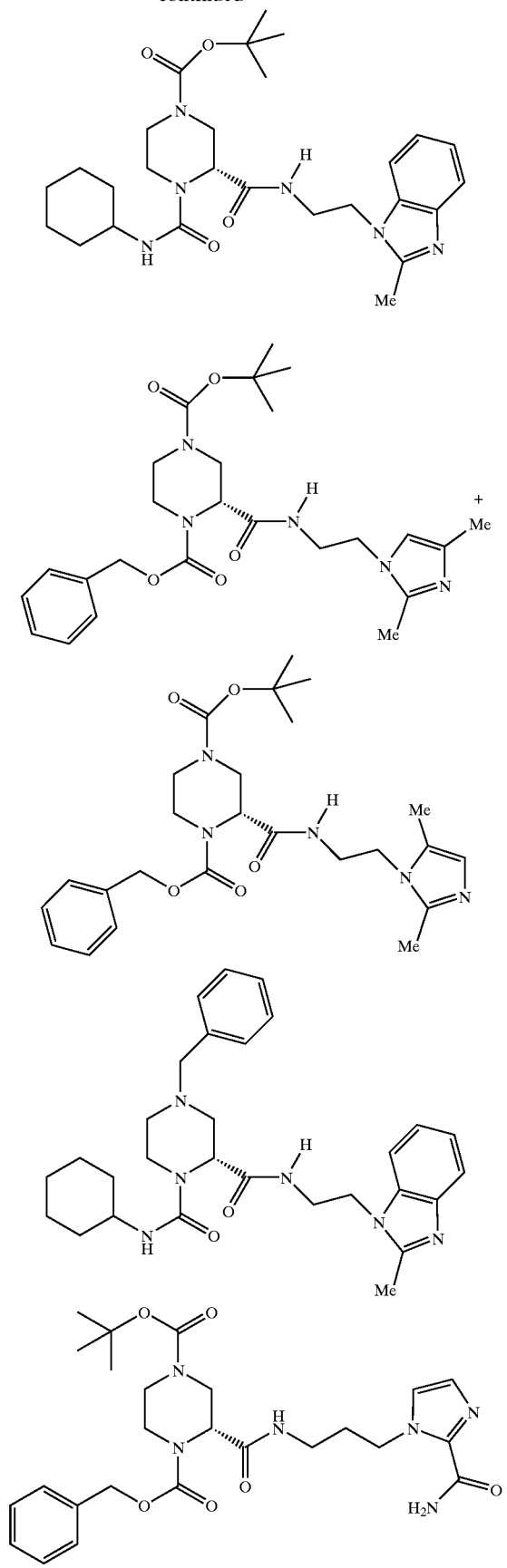
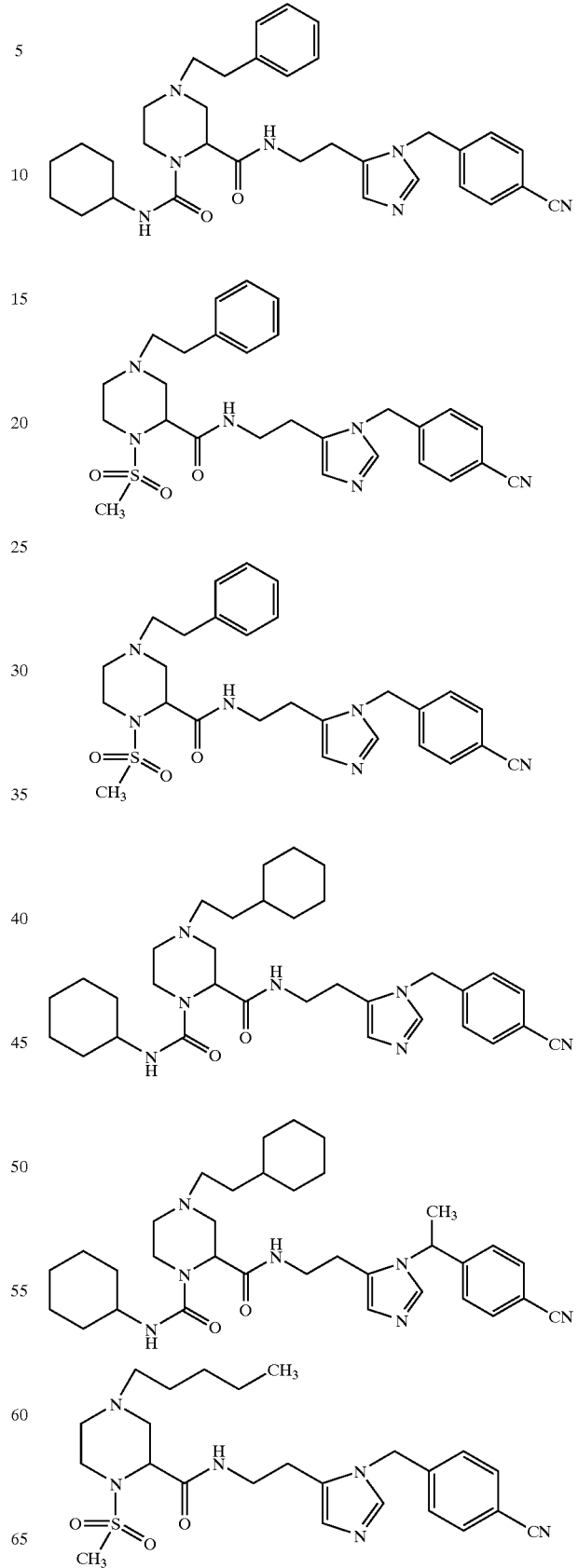

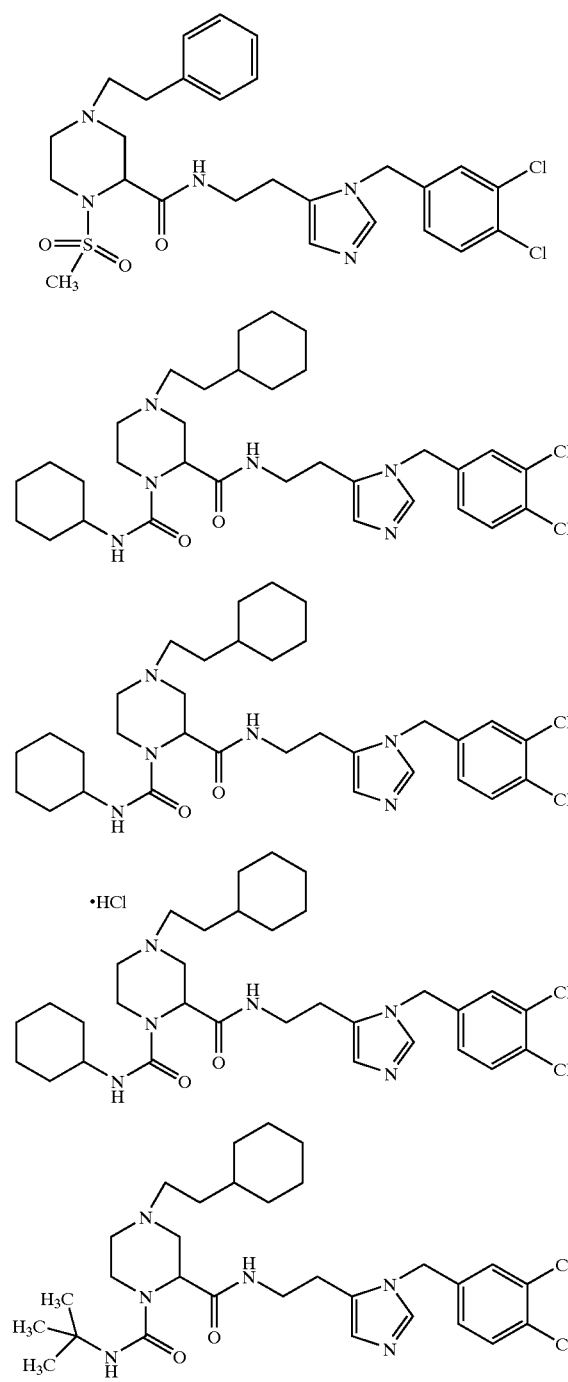
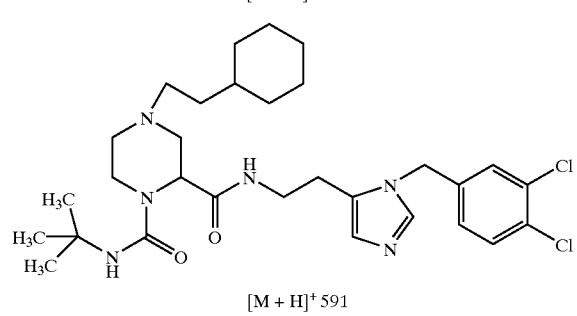
[M + H]⁺ 592
[M + H]⁺ 591
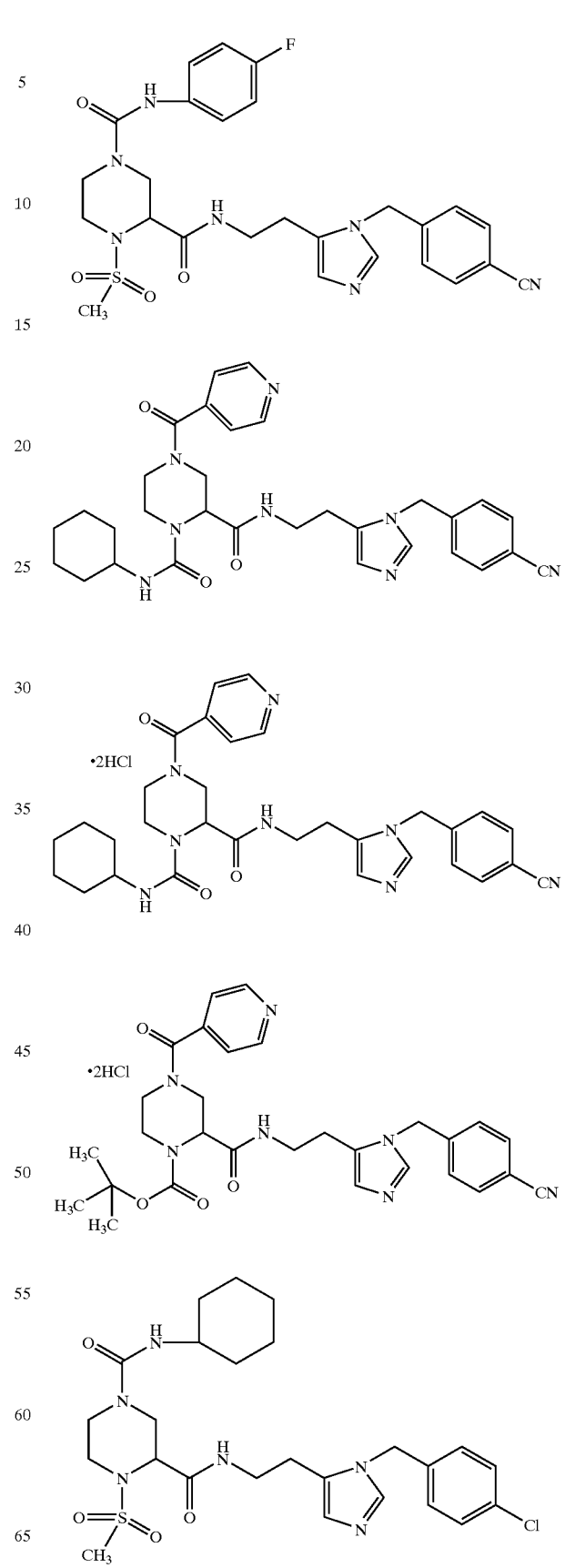

123
-continued
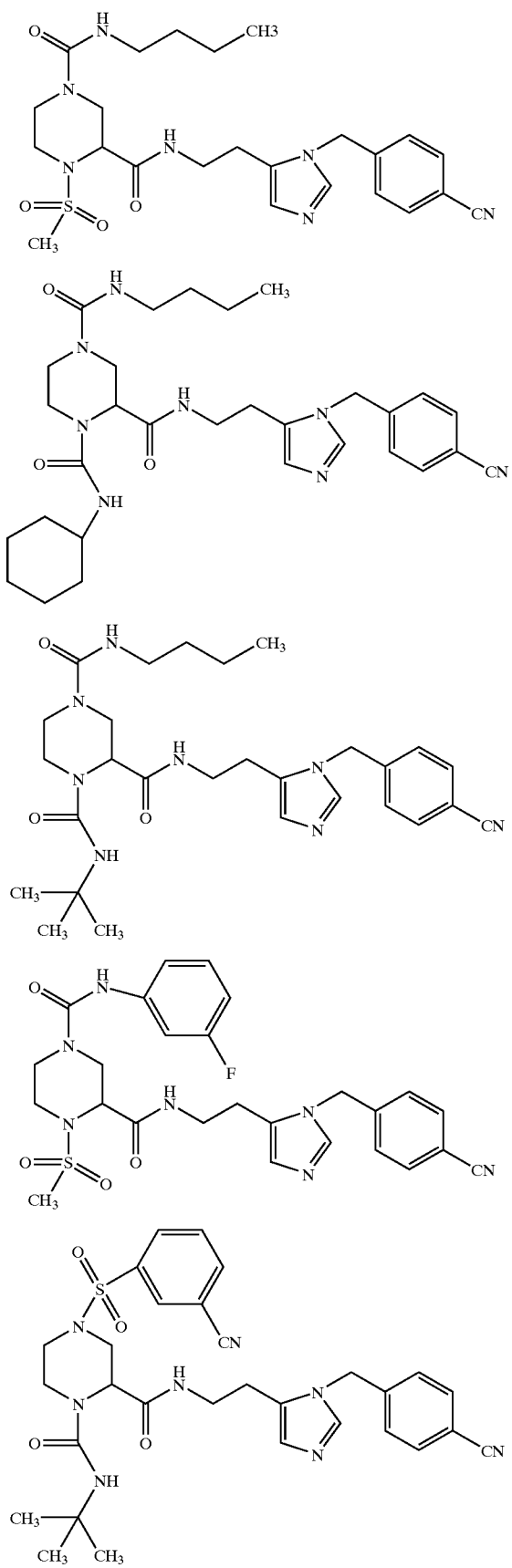
124
-continued
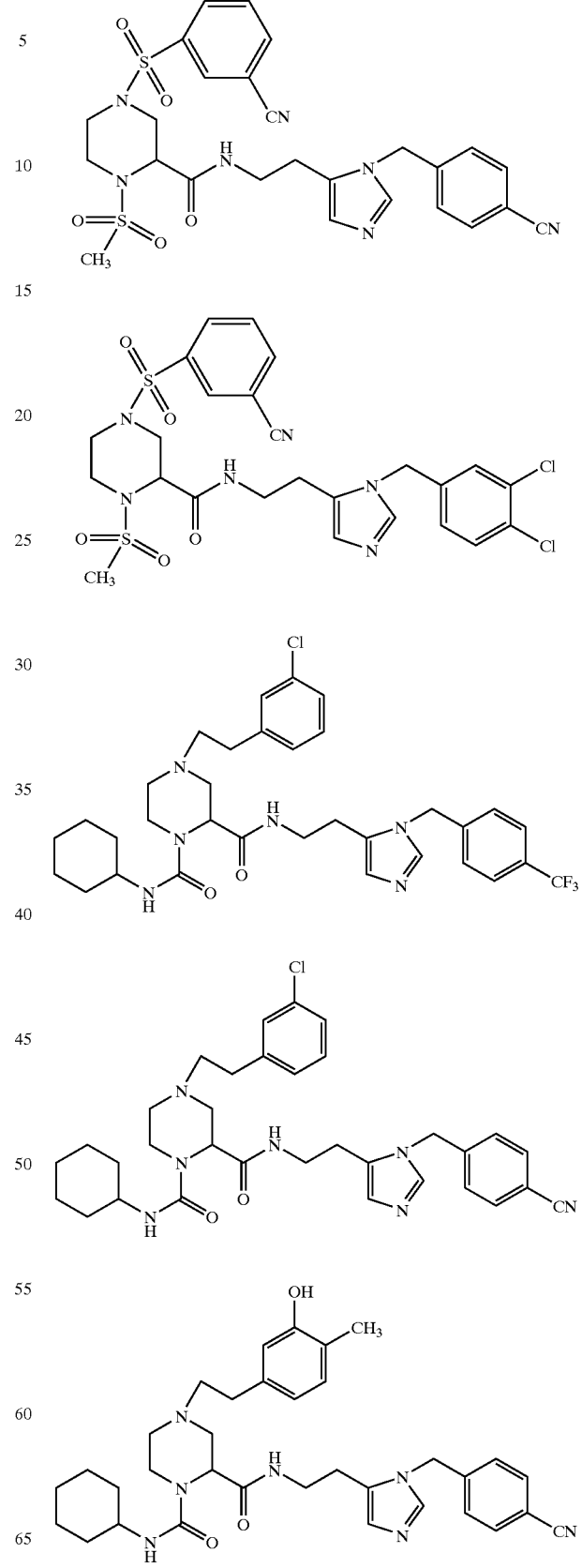

125
-continued
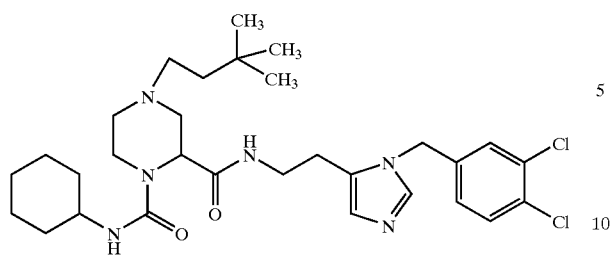
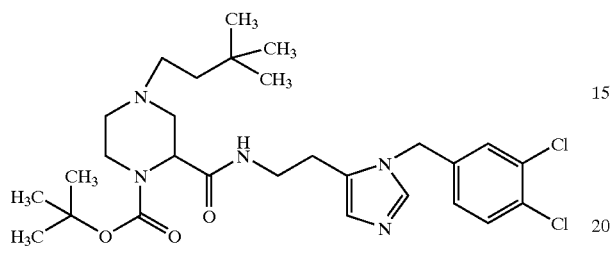
[M = H]+ 566
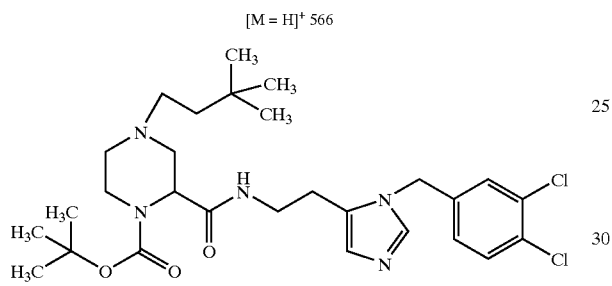
[M = H]+ 565
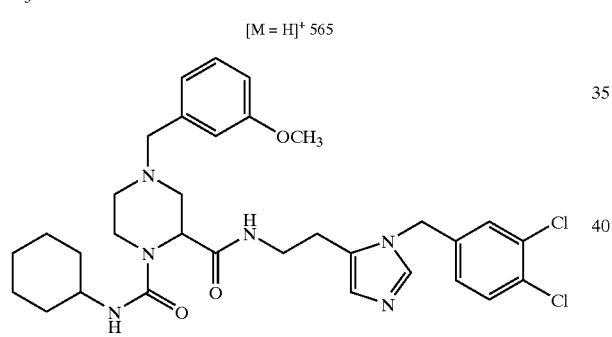
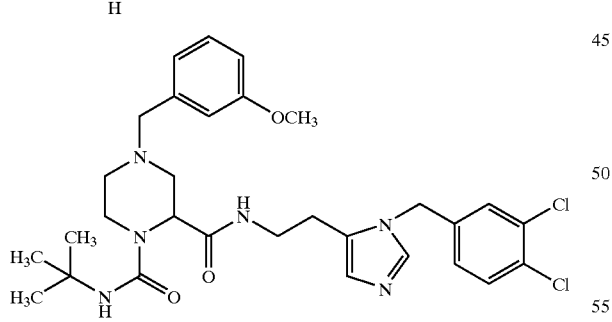
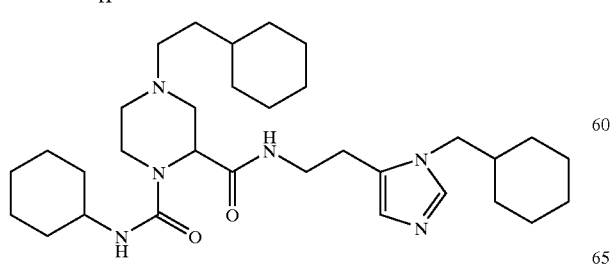
126
-continued
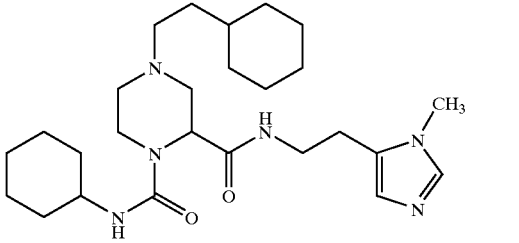
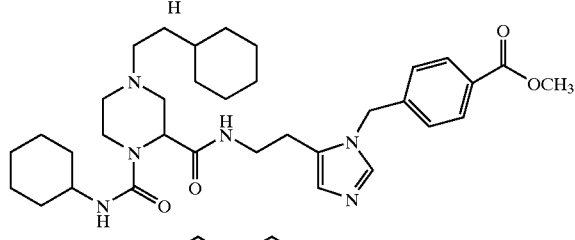
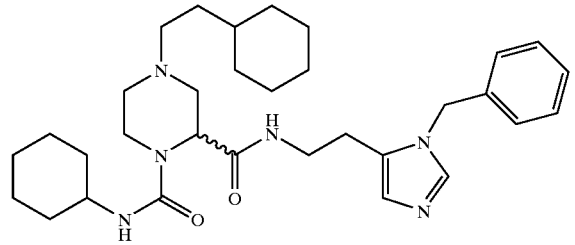
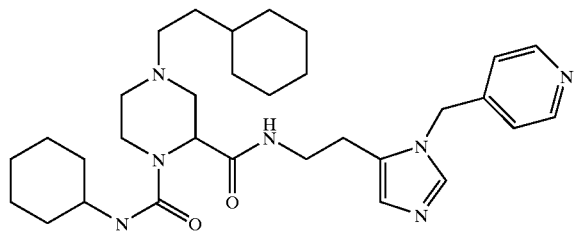
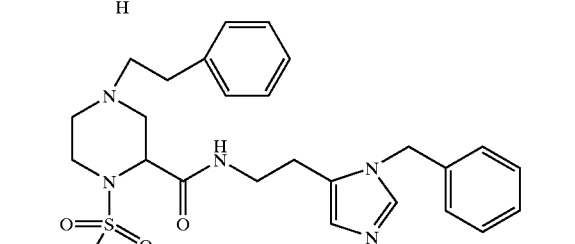
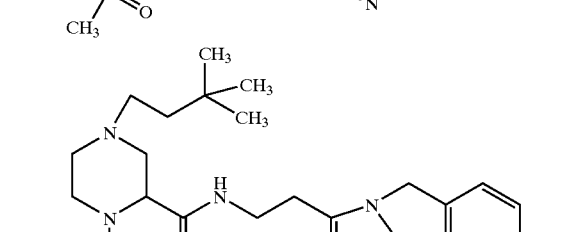
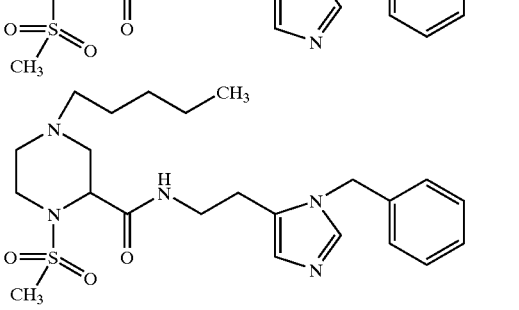

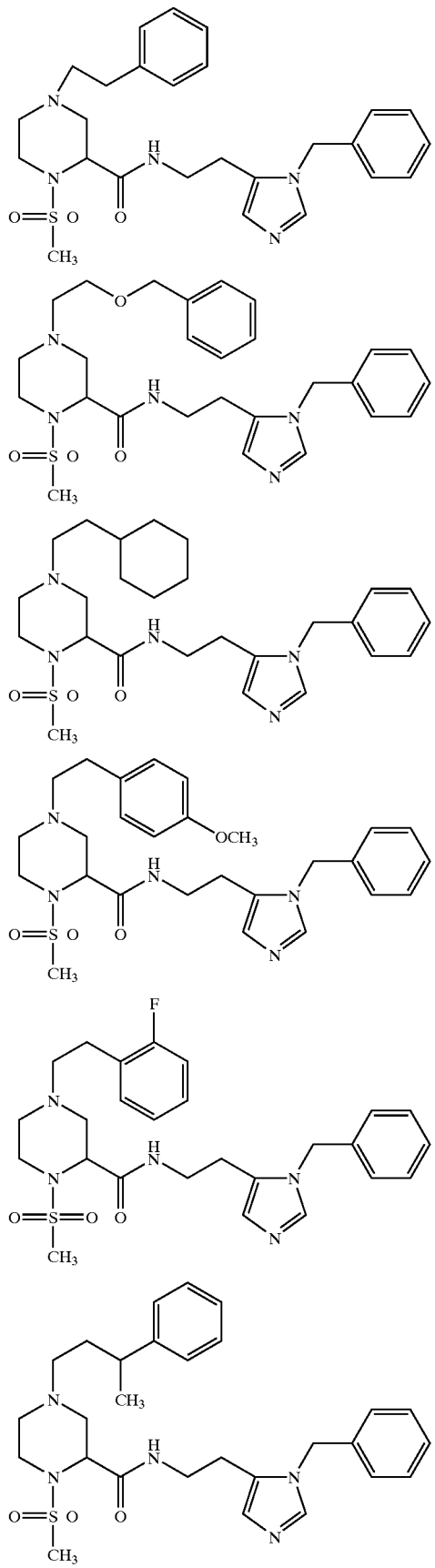
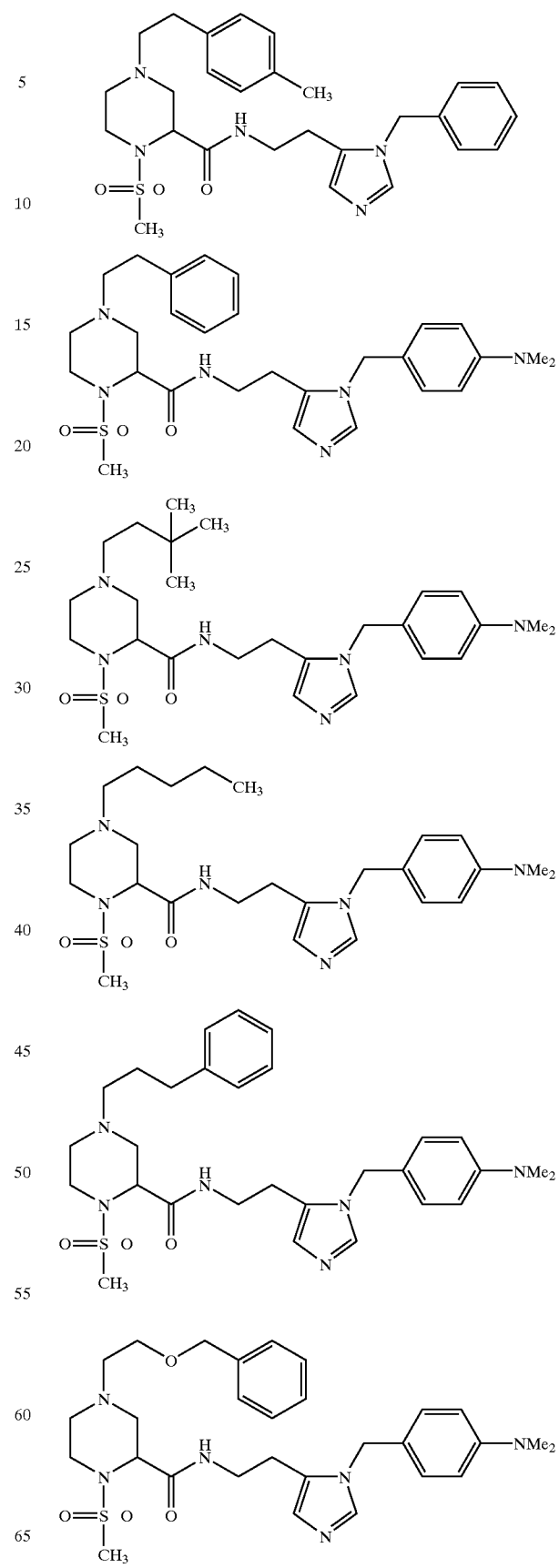

-continued
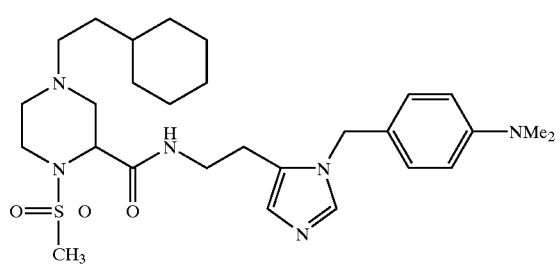
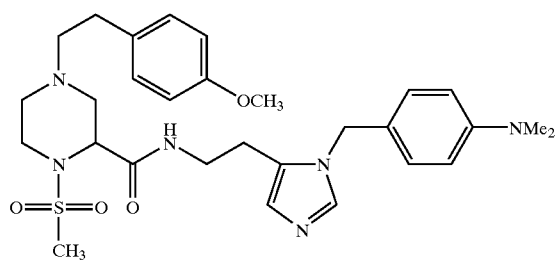
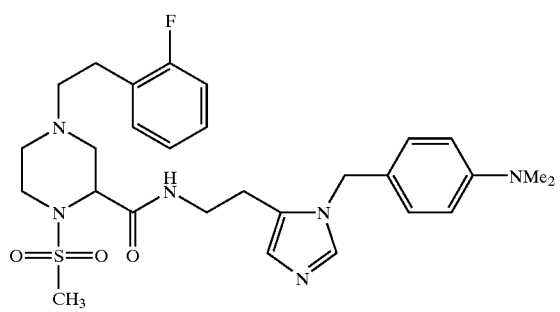
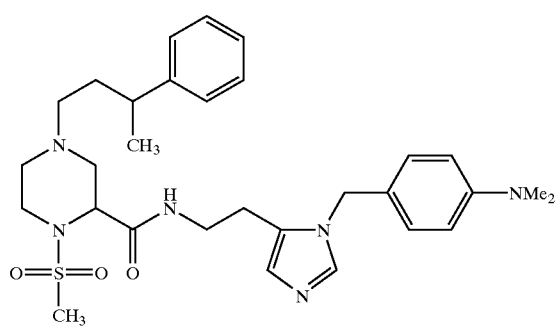
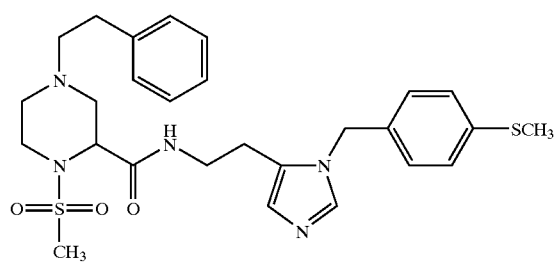
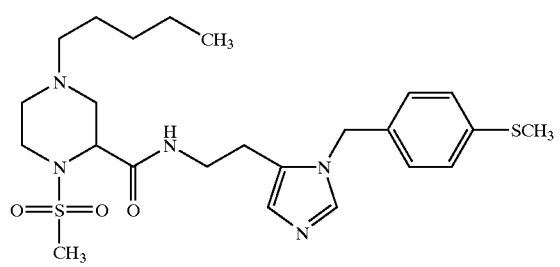
-continued
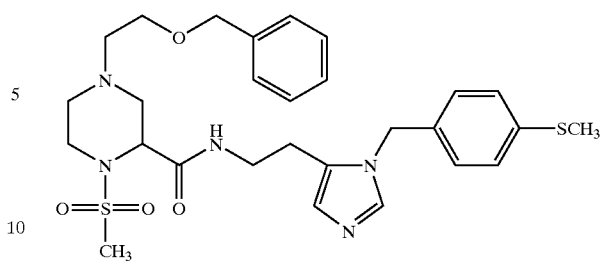
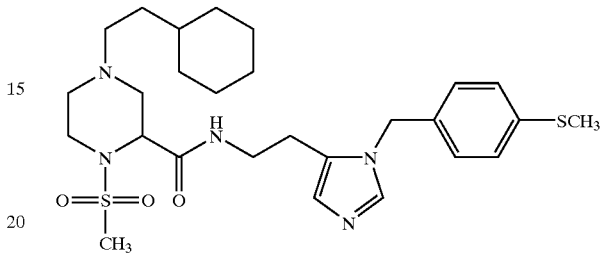
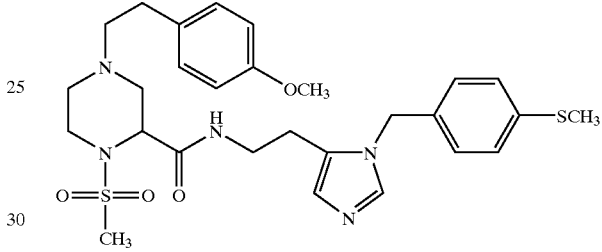
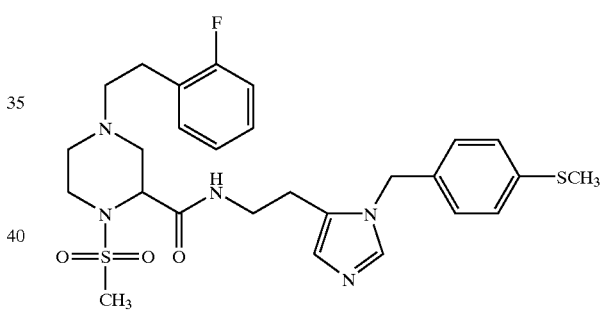
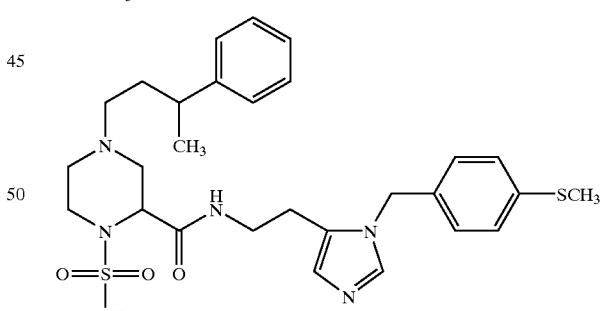
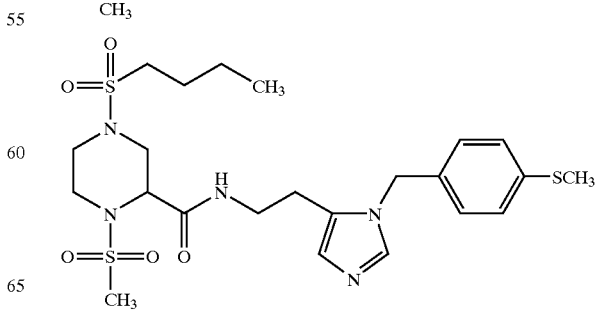

131
-continued
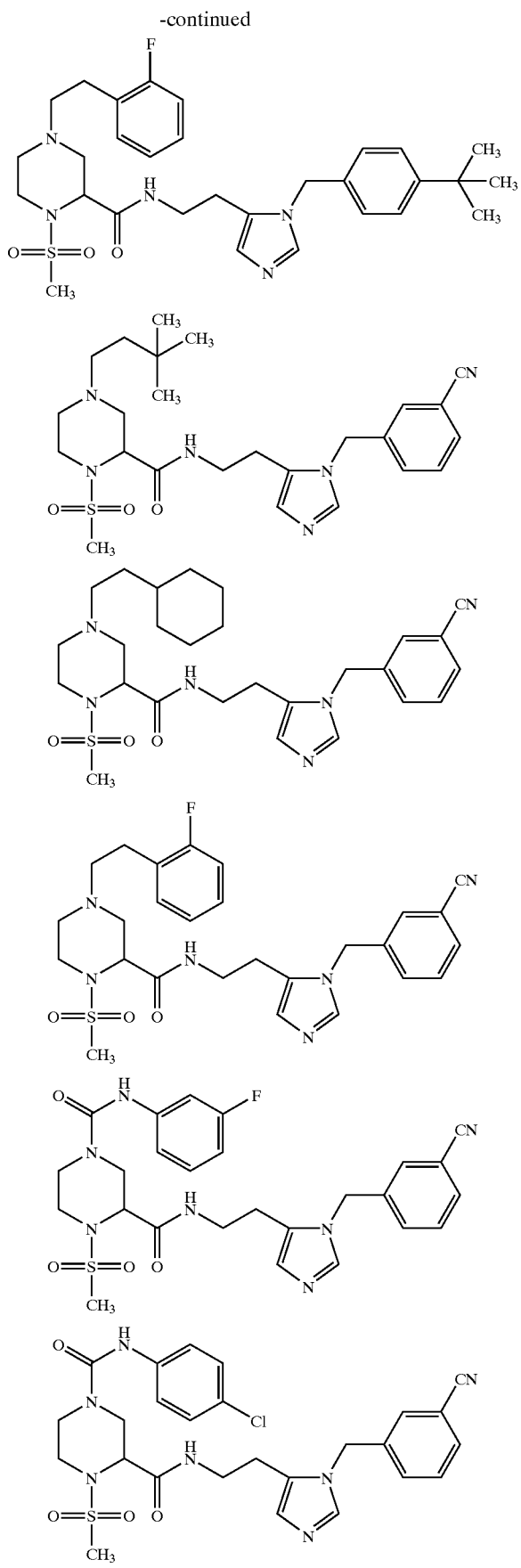
132
-continued
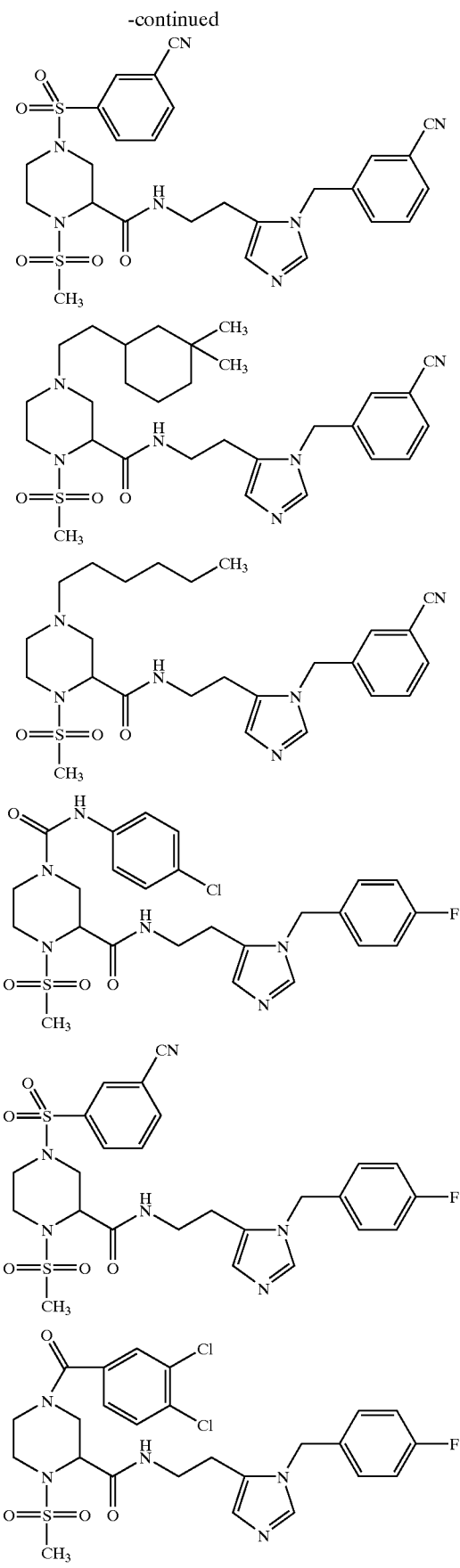

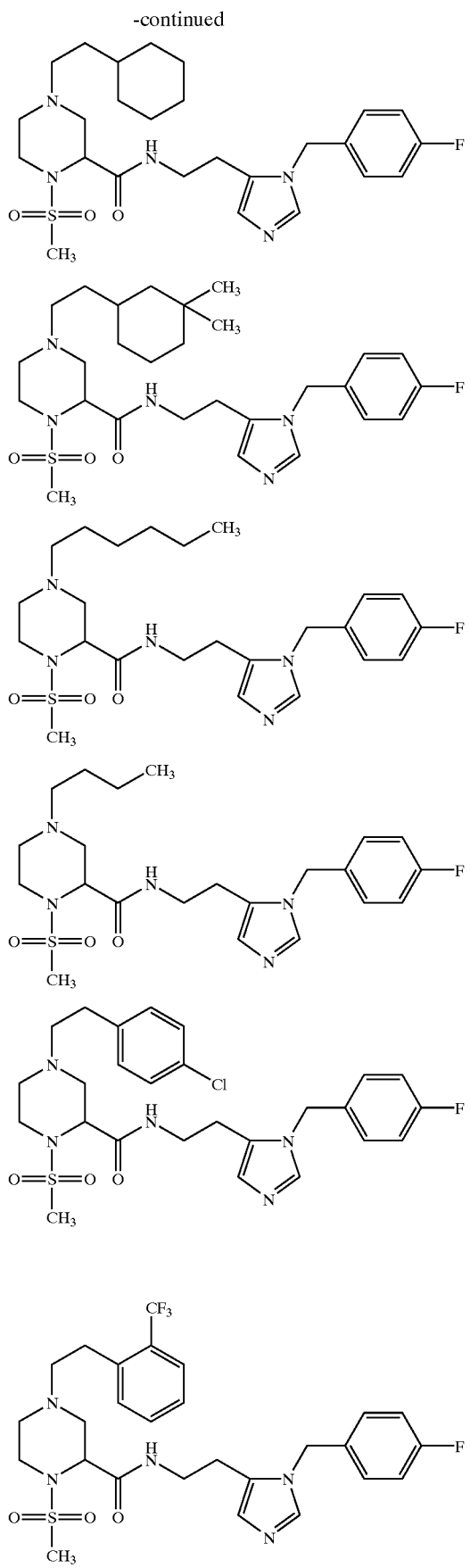
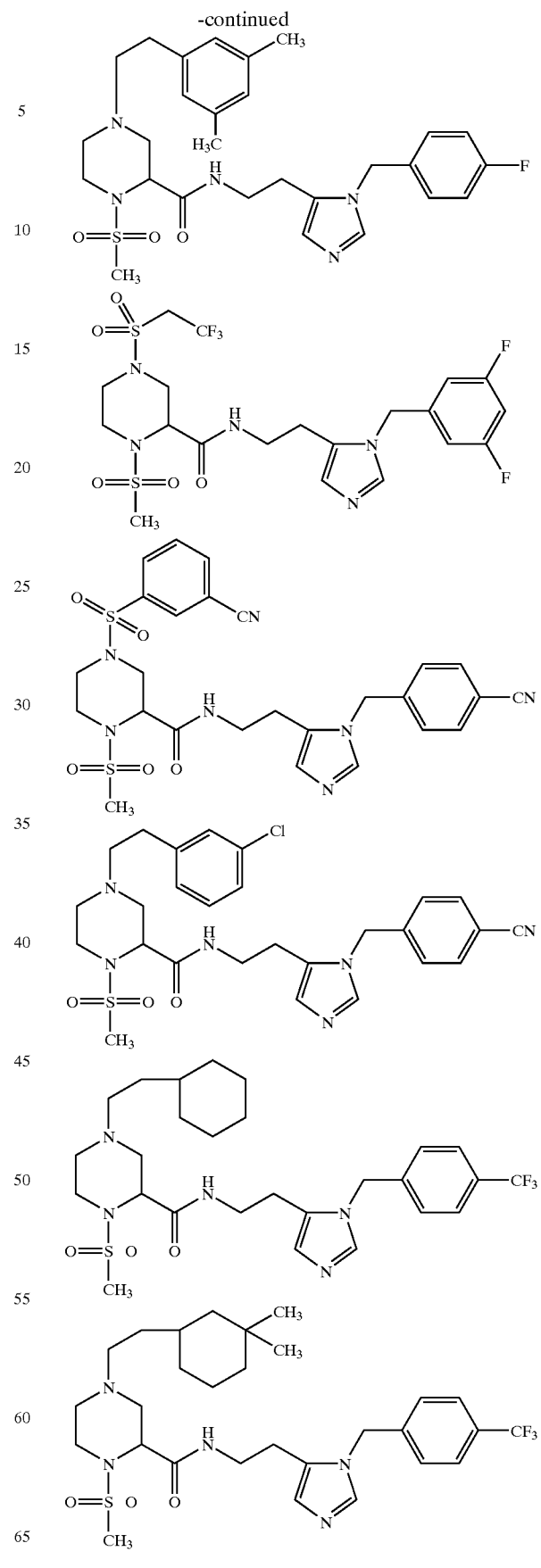

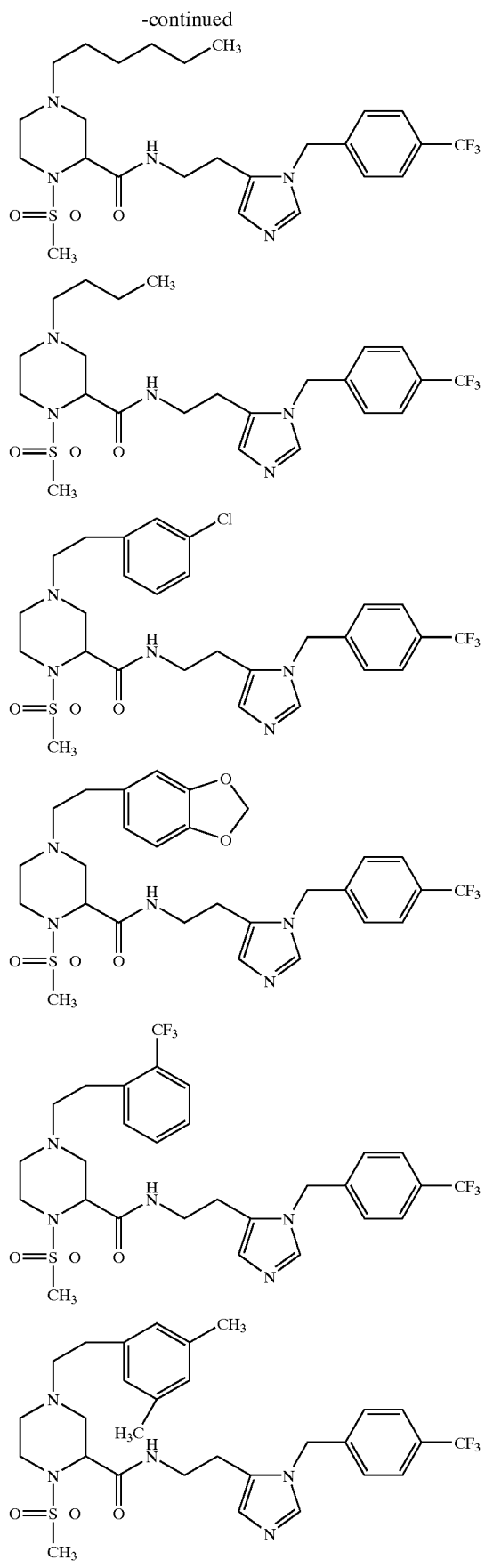
the compound of wherein Z is selected from:
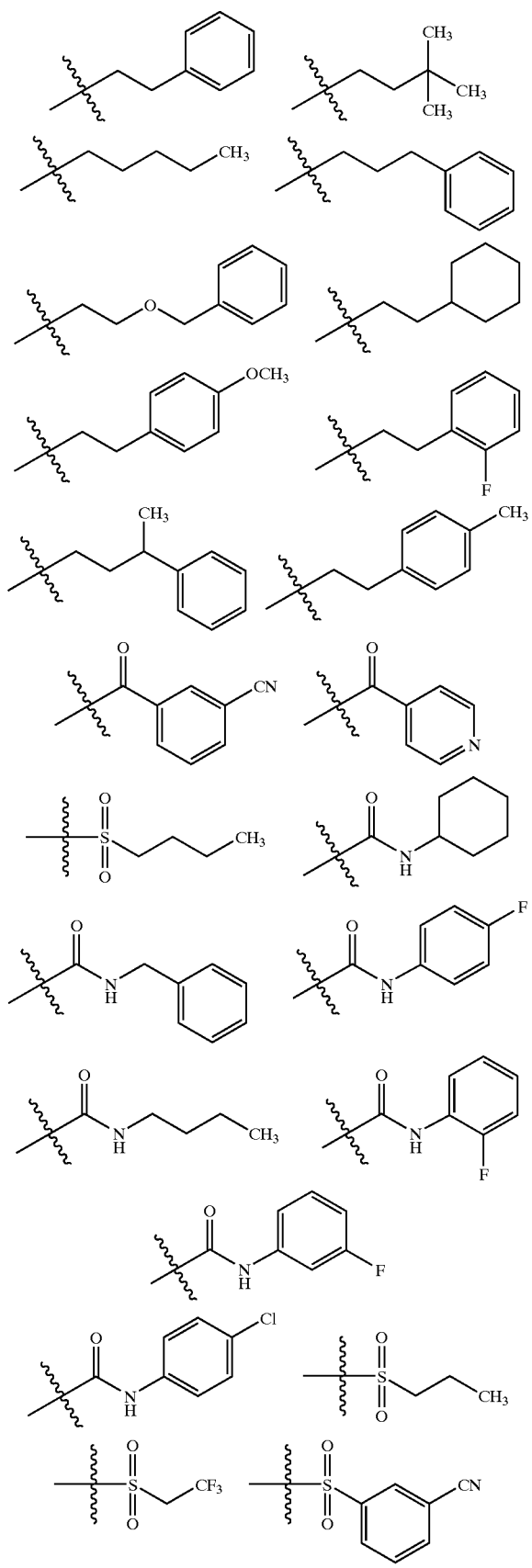
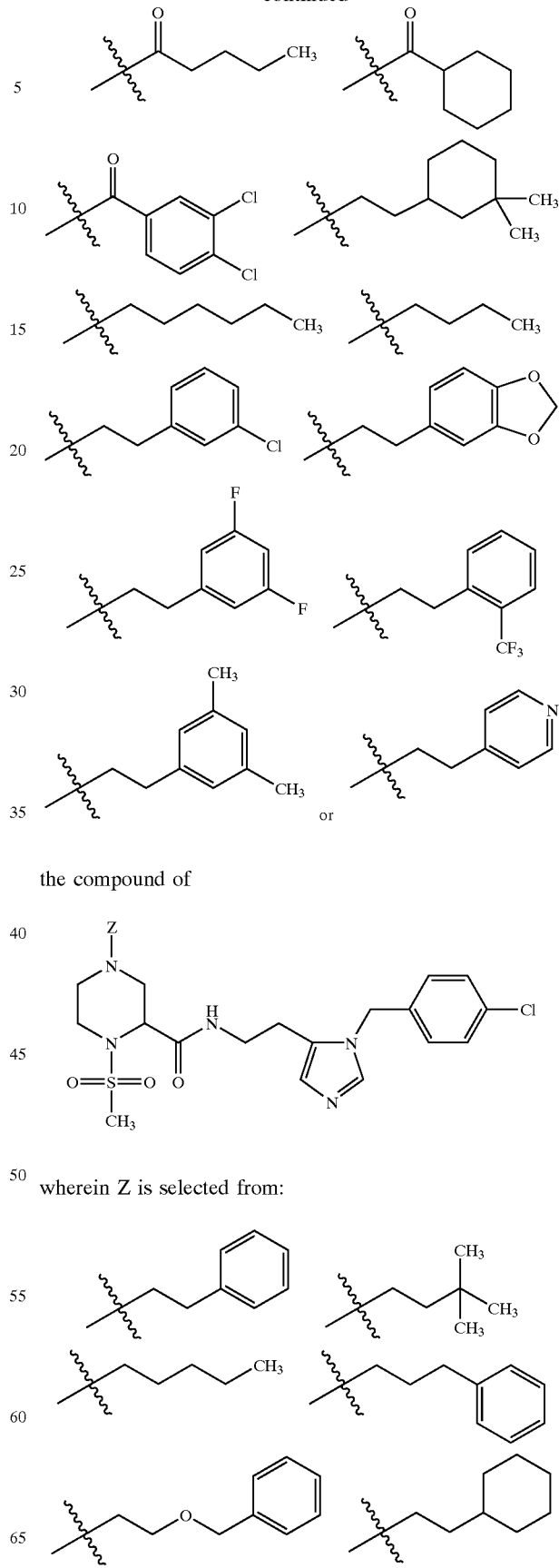
the compound of
wherein Z is selected from:

-continued
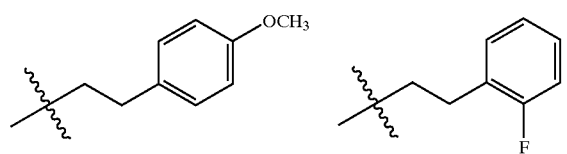
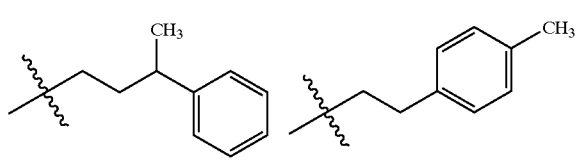
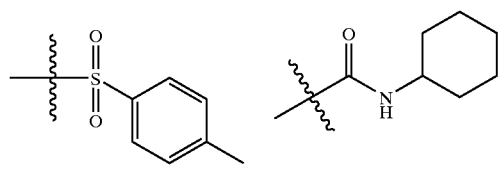
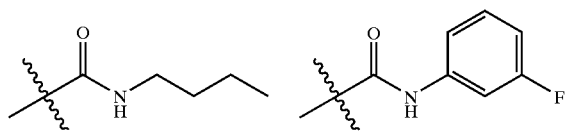
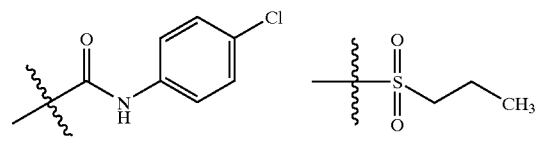
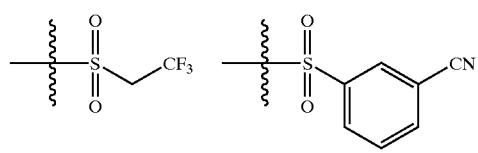
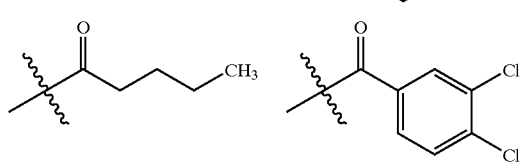
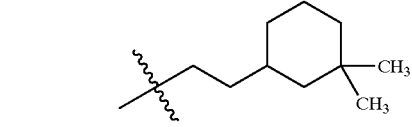
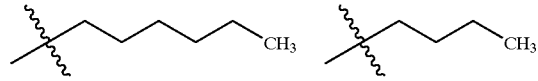
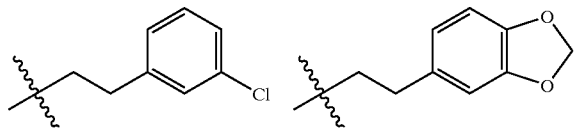
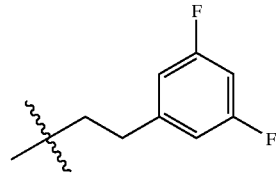
-continued
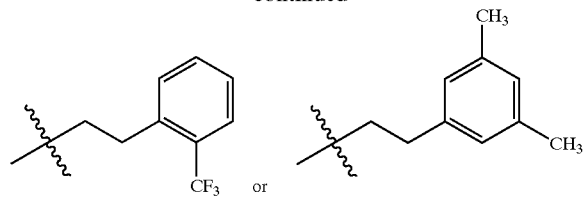 or
the compound of
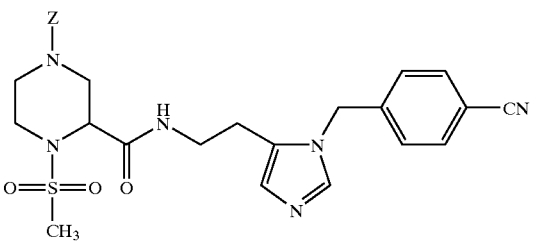
wherein Z is selected from:
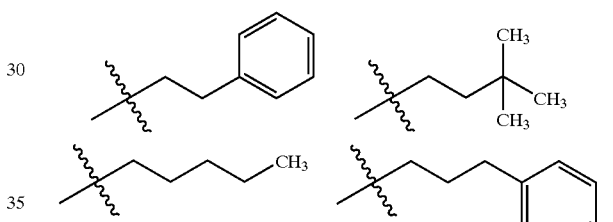
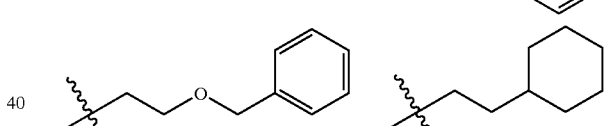
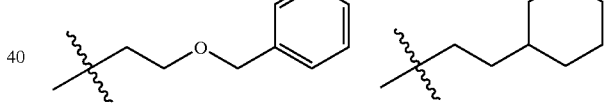
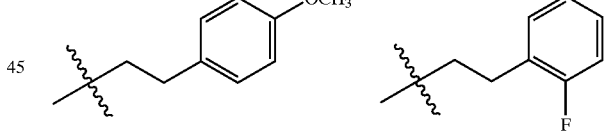
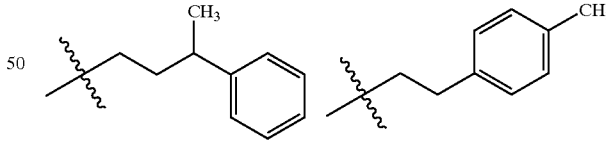
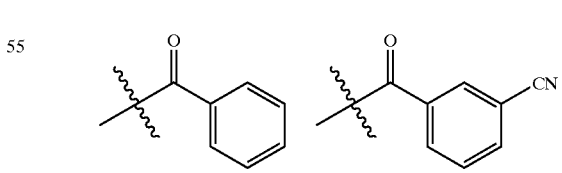
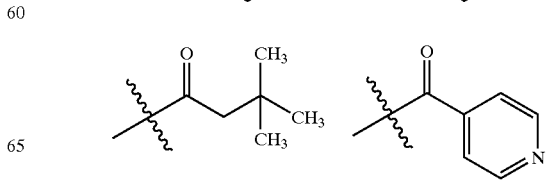

-continued
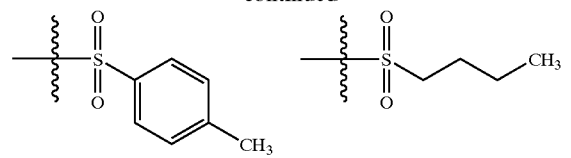
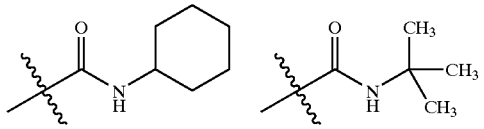
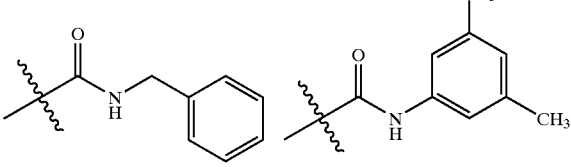
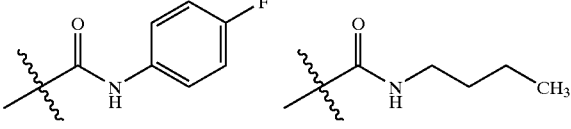
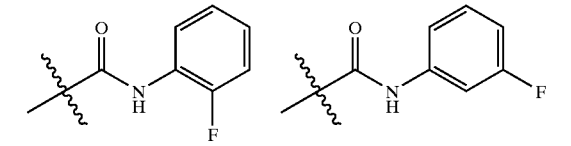
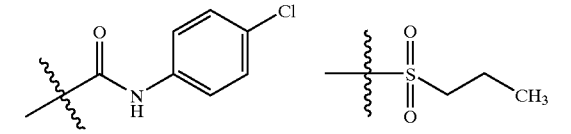
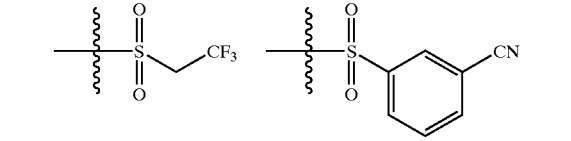
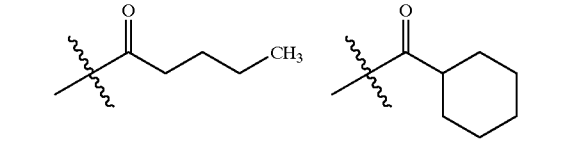
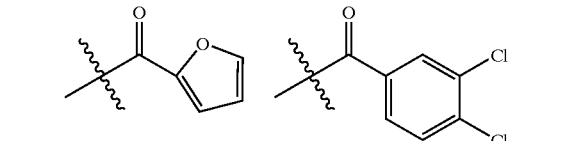
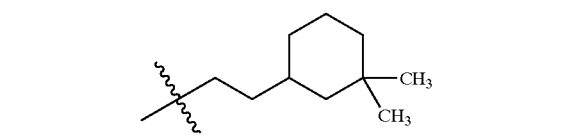
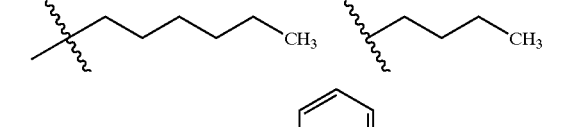
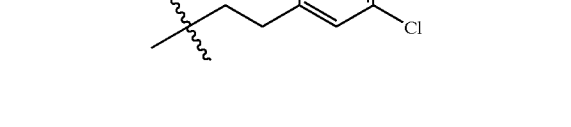
-continued
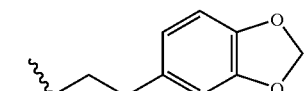
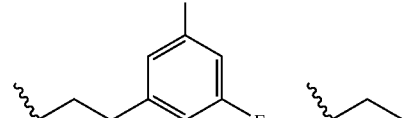
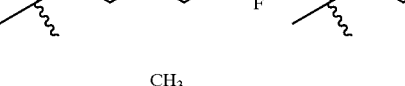
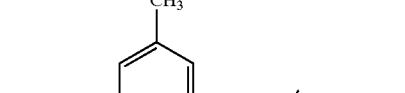
or
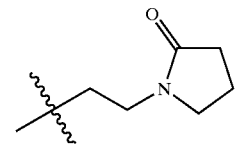
and

2. A compound selected from the group consisting of:
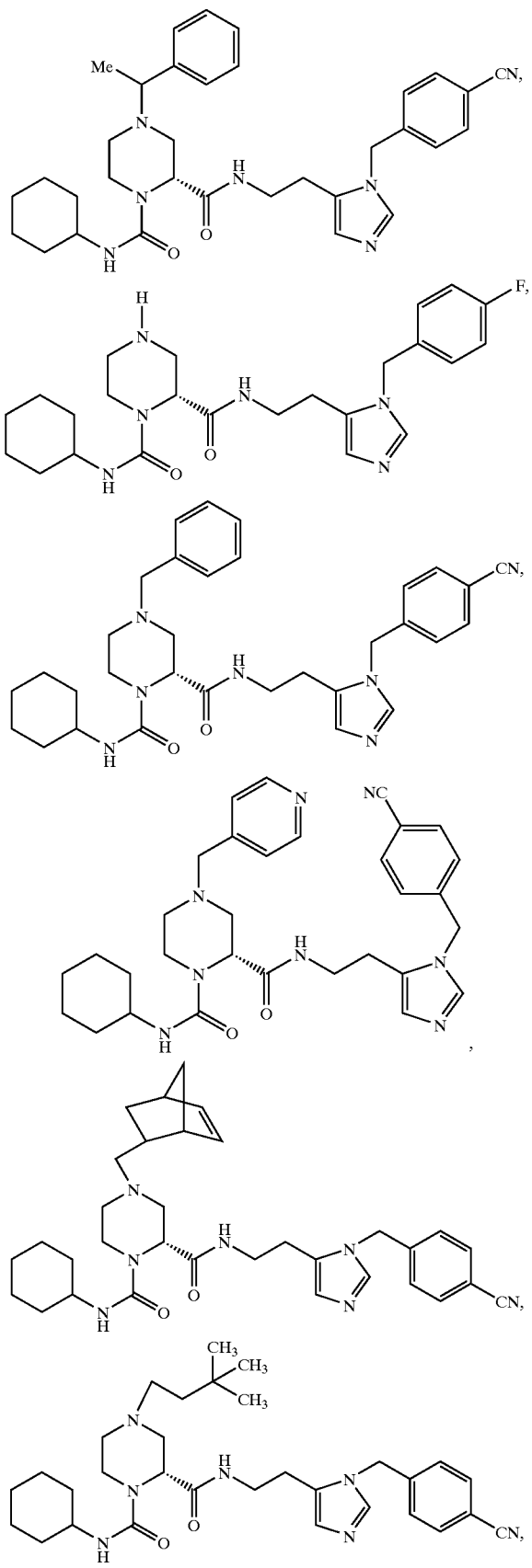
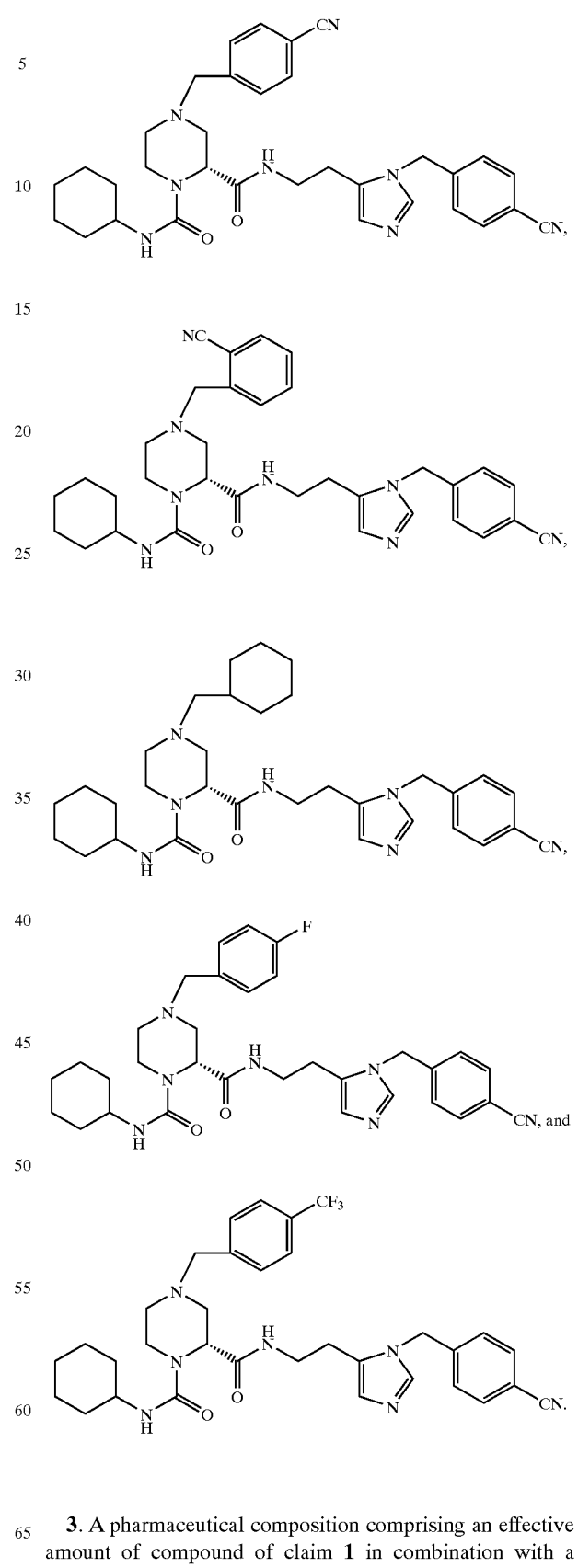
3. A pharmaceutical composition comprising an effective amount of compound of claim 1 in combination with a pharmaceutically acceptable carrier.

4. A pharmaceutical composition comprising an effective amount of compound of claim 2 in combination with a pharmaceutically acceptable carrier.

5. A method of inhibiting farnesyl protein transferase in a patient in need thereof comprising administering to said patient an effective amount of a compound of claim 1.

6. A method of inhibiting farnesyl protein transferase in a patient in need thereof comprising administering to said patient an effective amount of a compound of claim 2.

* * * * *